(12) United States Patent
Lee et al.

(10) Patent No.: US 10,716,523 B2
(45) Date of Patent: Jul. 21, 2020

(54) X-RAY IMAGING APPARATUS AND METHOD FOR CONTROLLING THE SAME

(71) Applicant: SAMSUNG ELECTRONICS CO., LTD., Suwon-si (KR)

(72) Inventors: Ho Jun Lee, Suwon-si (KR); Ju Hwan Kim, Suwon-si (KR); Se Hui Kim, Anyang-si (KR); Seung-Hoon Kim, Suwon-si (KR); Si Won Park, Suwon-si (KR); Phill Gu Jung, Suwon-si (KR); Duhgoon Lee, Yongin-si (KR); Myung Jin Chung, Seoul (KR); Do Hyeong Hyeong Hwang, Seoul (KR); Sung Jin Park, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 16/140,055

(22) Filed: Sep. 24, 2018

(65) Prior Publication Data
US 2019/0029621 A1    Jan. 31, 2019

Related U.S. Application Data

(63) Continuation of application No. 15/247,253, filed on Aug. 25, 2016, now Pat. No. 10,098,598, which is a
(Continued)

(30) Foreign Application Priority Data

Aug. 25, 2015  (KR) .................. 10-2015-0119878
Aug. 26, 2015  (KR) .................. 10-2015-0120581
Aug. 25, 2016  (KR) .................. 10-2016-0108198

(51) Int. Cl.
*A61B 6/00* (2006.01)
*A61B 6/06* (2006.01)

(52) U.S. Cl.
CPC ............ *A61B 6/465* (2013.01); *A61B 6/4452* (2013.01); *A61B 6/469* (2013.01); *A61B 6/5241* (2013.01);
(Continued)

(58) Field of Classification Search
CPC ......... A61B 6/06; A61B 6/4233; A61B 6/463; A61B 6/465; A61B 6/467; A61B 6/469; A61B 6/5241; A61B 6/542
See application file for complete search history.

(56) References Cited

U.S. PATENT DOCUMENTS

| 5,841,436 A | 11/1998 | Nakamura |
| 6,895,076 B2 | 5/2005 | Halsmer et al. |

(Continued)

FOREIGN PATENT DOCUMENTS

| DE | 10 2006 001 850 A1 | 8/2007 |
| EP | 1484016 | 12/2004 |

(Continued)

OTHER PUBLICATIONS

Chinese Office Action dated Jun. 3, 2016.
(Continued)

*Primary Examiner* — Chih-Cheng Kao
(74) *Attorney, Agent, or Firm* — Sughrue Mion, PLLC

(57) ABSTRACT

An X-ray imaging apparatus includes an imaging device that captures a camera image of a target, a controller that stitches a plurality of X-ray images of a plurality of divided regions to generate one X-ray image of the target, and a display that displays a settings window providing a graphical user interface for receiving a setting of an X-ray irradiation condition for the divided regions, and displays the camera image in which positions of the divided regions are displayed.

13 Claims, 41 Drawing Sheets

Related U.S. Application Data continuation-in-part of application No. 14/831,175, filed on Aug. 20, 2015, now Pat. No. 9,532,763, which is a continuation-in-part of application No. 13/917,121, filed on Jun. 13, 2013, now Pat. No. 9,149,247, said application No. 15/247,253 is a continuation-in-part of application No. 14/838,870, filed on Aug. 28, 2015, now Pat. No. 9,814,435.

(52) U.S. Cl.
CPC ............... *A61B 6/545* (2013.01); *A61B 6/06* (2013.01); *A61B 6/4464* (2013.01); *A61B 6/463* (2013.01); *A61B 6/467* (2013.01); *A61B 6/504* (2013.01); *A61B 6/54* (2013.01)

(56) References Cited

U.S. PATENT DOCUMENTS

| | | |
|---|---|---|
| 8,396,184 B2 | 3/2013 | Shinno |
| 9,149,247 B2 | 10/2015 | Lee |
| 9,532,763 B2 | 1/2017 | Lee et al. |
| 10,098,598 B2* | 10/2018 | Lee .................. A61B 6/465 |
| 2004/0247081 A1 | 12/2004 | Halsmer et al. |
| 2005/0169425 A1 | 8/2005 | Takasawa |
| 2005/0169427 A1 | 8/2005 | Halsmer |
| 2007/0012880 A1 | 1/2007 | Haider et al. |
| 2008/0019480 A1 | 1/2008 | Cheng et al. |
| 2008/0037708 A1 | 2/2008 | Kuzmanovic |
| 2009/0060125 A1 | 3/2009 | Tsuyuki et al. |
| 2009/0103679 A1 | 4/2009 | Jabri et al. |
| 2011/0249799 A1 | 10/2011 | Lalena et al. |
| 2011/0291800 A1 | 12/2011 | Butzine et al. |
| 2012/0128125 A1 | 5/2012 | Jabri et al. |
| 2012/0183126 A1* | 7/2012 | Cho .................. A61B 6/06 378/150 |
| 2012/0275645 A1* | 11/2012 | Koenig .................. A61B 5/06 382/103 |
| 2013/0022172 A1* | 1/2013 | Lee .................. A61B 6/462 378/63 |
| 2013/0077745 A1 | 3/2013 | Wang et al. |
| 2013/0142306 A1 | 6/2013 | Okuno |
| 2013/0336445 A1 | 12/2013 | Sehnert |
| 2013/0343523 A1 | 12/2013 | Lee |
| 2014/0037057 A1 | 2/2014 | Kim |
| 2014/0056408 A1 | 2/2014 | Tajima |
| 2014/0072198 A1* | 3/2014 | Moon .................. A61B 6/461 382/131 |

FOREIGN PATENT DOCUMENTS

| | | |
|---|---|---|
| EP | 2250965 | 11/2010 |
| EP | 2389864 | 11/2011 |
| EP | 2548509 A1 | 1/2013 |
| EP | 2676609 A1 | 12/2013 |
| JP | 9-313475 A | 12/1997 |
| JP | 10201750 A | 8/1998 |
| JP | 2005296064 A | 10/2005 |
| JP | 2005304698 A | 11/2005 |
| JP | 2006280626 A | 10/2006 |
| JP | 2006-343193 A | 12/2006 |
| JP | 2009-078126 | 4/2009 |
| JP | 2009-254787 | 11/2009 |
| JP | 2011-125486 A | 6/2011 |
| JP | 2012-002696 A | 1/2012 |
| JP | 2012-147978 A | 8/2012 |
| JP | 2013-039197 A | 2/2013 |
| KR | 10-2013-0010425 A | 1/2013 |
| KR | 10-2013-0059489 A | 6/2013 |
| KR | 1020130059488 A | 6/2013 |
| KR | 10-2013-0142850 A | 12/2013 |
| KR | 10-2014-0033474 A | 3/2014 |
| KR | 10-2014-0127543 A | 11/2014 |
| WO | 2006/038165 A1 | 4/2006 |
| WO | 2013/154167 A1 | 10/2013 |

OTHER PUBLICATIONS

European Summons to Oral Proceedings dated May 31, 2016 from European Patent Application No. 13172965.9.
Korean Office Action dated Oct. 25, 2013 from Korean Patent Application No.10-2012-0066427.
European Extended Search Report dated Sep. 17, 2013 from European Patent Application No. 13172965.9.
U.S. Office Action dated Feb. 6, 2015 from U.S. Appl. No. 13/917,121.
U.S. Notice of Allowance dated May 29, 2015 from U.S. Appl. No. 13/917,121.
Communication dated Jan. 30, 2017, issued by the European Patent Office in counterpart European Application No. 16185734.7.
Communication dated Jul. 11, 2018 by the Korean Intellectual Property Office in counterpart Korean Application No. 10-2016-0108198.
Communication dated Dec. 7, 2015, issued by the International Searching Authority in counterpart International Application No. PCT/KR2015/009049 (PCT/ISA/220, PCT/ISA/210, PCT/ISA/237).
Notice of Allowance dated Aug. 17, 2016 issued by the United States Patent and Trademark Office in counterpart U.S. Appl. No. 14/831,175.
Office Action dated Oct. 2, 2015 issued by the United States Patent and Trademark Office in counterpart U.S. Appl. No. 14/831,175.
Communication dated Oct. 21, 2015 issued by the United States Patent and Trademark Office in counterpart U.S. Appl. No. 14/831,175.
Office Action dated May 6, 2016 issued by the United States Patent and Trademark Office in counterpart U.S. Appl. No. 14/831,175.
Communication dated Jun. 21, 2016 issued by the United States Patent and Trademark Office in counterpart U.S. Appl. No. 14/838,870.
Communication dated Jan. 2, 2018 by the Korean Intellectual Property Office in counterpart Korean Patent Application No. 10-2016-0108198.
Communication (Non-Final OA) dated Sep. 5, 2018 issued by the USPTO in counterpart U.S. Appl. No. 15/354,207.
Communication dated Oct. 1, 2018 issued by the Korean Intellectual Property Office in counterpart Korean Application No. 10-2016-0108198.
Communication dated Dec. 17, 2018, issued by the Chinese Patent Office in counterpart Chinese Application No. 201310247385.7.
Communication dated Feb. 7, 2019, issued by the European Patent Office in counterpart European Application No. 13172965.9.
Notice of Allowance dated Feb. 25, 2019, issued by the United States Patent and Trademark Office in U.S. Appl. No. 15/354,207.
Communication dated Mar. 22, 2019, issued by the European Patent Office in counterpart European Application No. 16 185 734.7.

* cited by examiner

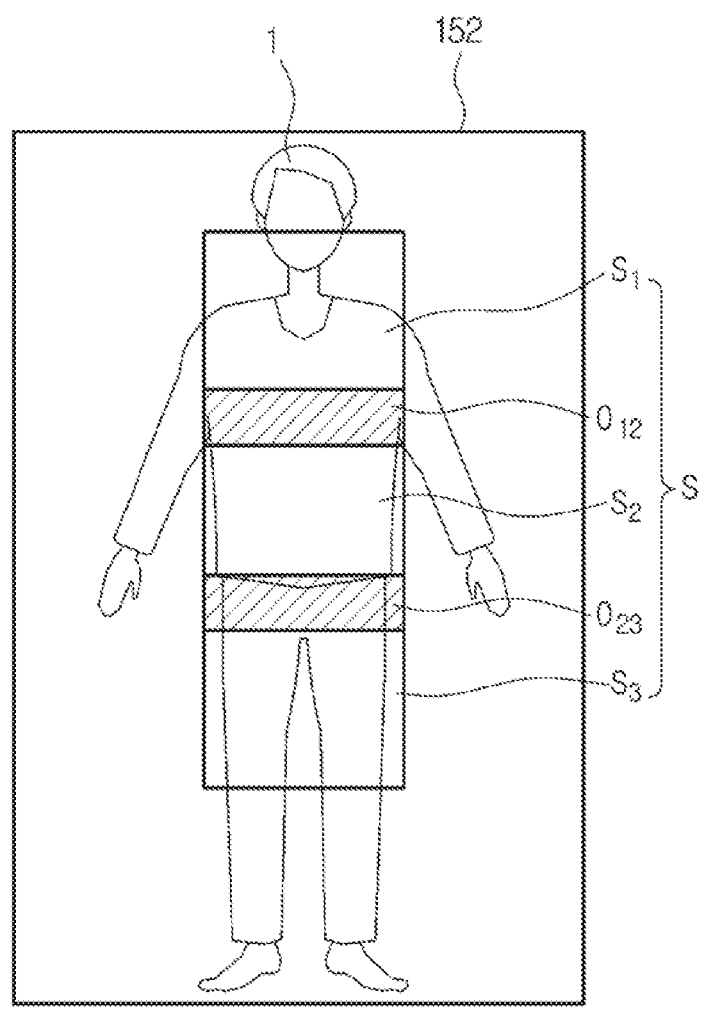

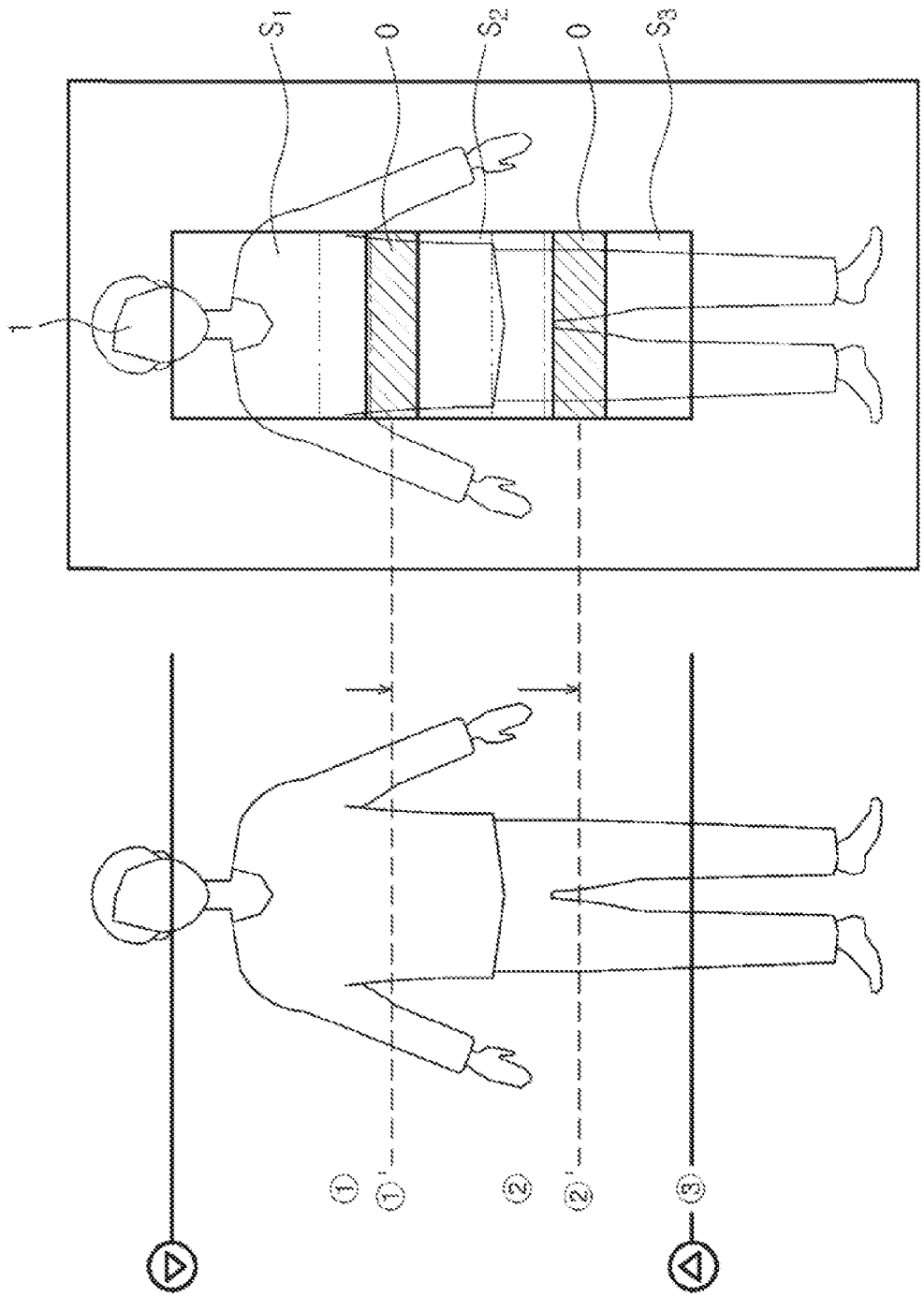

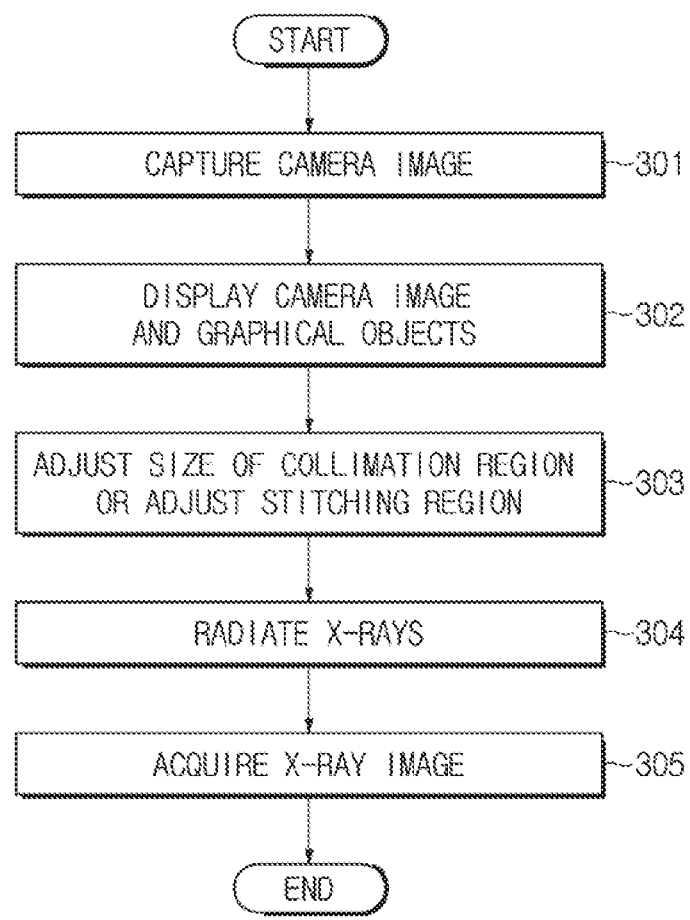

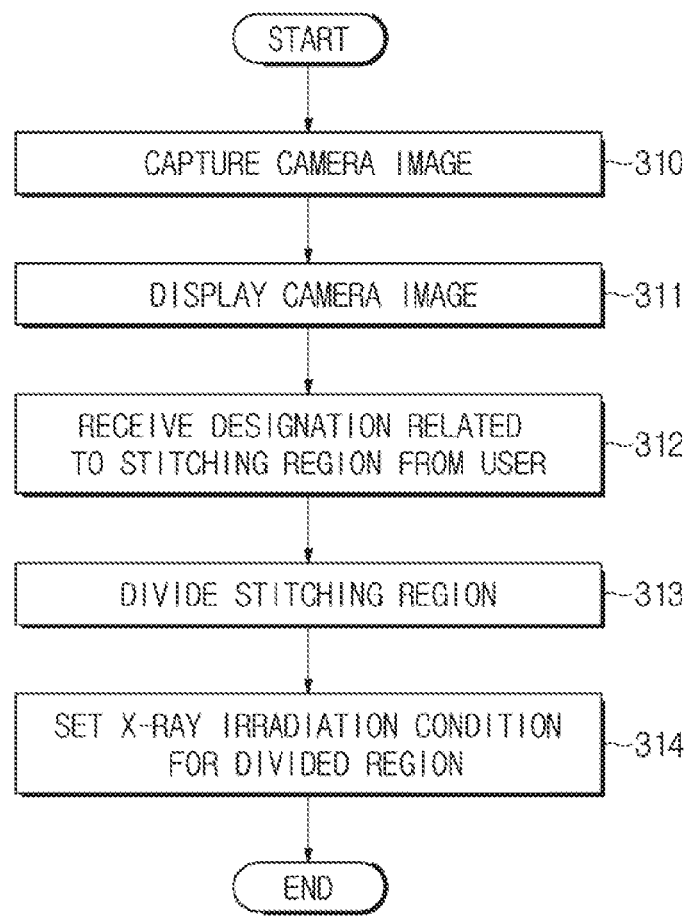

X-RAY IMAGING APPARATUS AND METHOD FOR CONTROLLING THE SAME

CROSS-REFERENCE TO RELATED PATENT APPLICATIONS

This application is a Continuation of U.S. application Ser. No. 15/247,253 filed Aug. 25, 2016, which claims priority from Korean Patent Application Nos. 10-2015-0119878, 10-2015-0120581, and 10-2016-0108198 filed Aug. 25, 2015, Aug. 26, 2015, and Aug. 25, 2016, respectively, in the Korean Intellectual Property Office. The U.S. application Ser. No. 15/247,253 is a CIP of U.S. application Ser. No. 14/838,870 filed Aug. 28, 2015, now U.S. Pat. No. 9,814,435 issued Nov. 14, 2017, which claims priority from Korean Patent Application Nos. 10-2015-0113857 filed Aug. 12, 2015 and 10-2014-0113349 filed Aug. 28, 2014, and a CIP of U.S. application Ser. No. 14/831,175 filed Aug. 20, 2015, now U.S. Pat. No. 9,532,763 issued Jan. 3, 2017, which is a Continuation of U.S. application Ser. No. 13/917,121 filed Jun. 13, 2013, now U.S. Pat. No. 9,149,247 issued Oct. 6, 2015, which claims priority from Korean Patent Application No. 10-2012-0066427, filed Jun. 20, 2012. The disclosures of all of the above-noted applications are incorporated herein by reference in their entireties.

BACKGROUND

1. Field

Methods and apparatuses consistent with exemplary embodiments relate to an X-ray imaging apparatus in which a portion of an object to be imaged is divided into regions, the regions are imaged, and then the imaged regions are stitched, and a method for controlling the same.

2. Description of the Related Art

An X-ray imaging apparatus irradiates an object with X-rays and analyzes X-rays that have been transmitted through the object to recognize an inner structure of the object. Since X-ray transmittance varies according to a tissue forming an object, an inner structure of the object may be imaged using an attenuation coefficient which is a numerical value of X-ray transmittance.

A part which is desired to be imaged may not be entirely captured by a single imaging in some cases due to various reasons including a case in which the impinging X-ray irradiation beam is smaller than a portion to be imaged and a case in which a detector region is smaller than a portion to be imaged.

Accordingly, one X-ray image of the desired portion to be imaged may be obtained by capturing partial X-ray images and combining the partial X-ray images.

SUMMARY

One or more exemplary embodiments provide an X-ray imaging apparatus that displays a plurality of divided regions, with which stitching imaging will be performed on a camera image, and has the divided regions displayed on the camera image interoperate with an X-ray irradiation condition setting screen for each of the divided regions to allow a user to intuitively and easily recognize the divided region for which an X-ray irradiation condition is being set, and a method for controlling the same.

Additional aspects of the disclosure will be set forth in part in the description which follows and, in part, will be obvious from the description or may be learned by practice of the disclosure.

According to an aspect of an exemplary embodiment, an X-ray imaging apparatus includes an imaging device that captures a camera image, a controller that stitches a plurality of X-ray images of a plurality of divided regions to generate one X-ray image, and a display that displays a setting window providing a graphical user interface for receiving a setting of an X-ray irradiation condition for each of the plurality of divided regions and the camera image in which positions of the plurality of divided regions are displayed.

The display may display a plurality of divided windows showing the positions of the plurality of divided regions by overlaying the plurality of divided windows on the camera image.

The display may have the setting window and the camera image on which the plurality of divided windows are overlaid interoperate and displayed.

When one of the plurality of divided regions is selected, the display may activate the graphical user interface for receiving a setting of an X-ray irradiation condition of the selected divided region to display the graphical user interface on the setting window and may display a position of the selected divided region on the camera image.

The display may display a plurality of identification tags respectively corresponding to the plurality of divided regions on the setting window and, when one of the plurality of identification tags is selected, may activate a graphical user interface for receiving a setting of an X-ray irradiation condition of a divided region corresponding to the selected identification tag.

The display may display a position of the divided region corresponding to the selected identification tag on the camera image.

When one divided window among the plurality of divided windows displayed in the camera image is selected, the display may activate a graphical user interface for receiving a setting of an X-ray irradiation condition of a divided region corresponding to the selected divided window.

The display may display a graphical object for receiving the setting of the X-ray irradiation condition by overlaying the graphical object on the camera image.

The display may display the graphical user interface on the setting window by synchronizing the graphical user interface with a command input through the graphical object displayed in the camera image.

The display may display the graphical object for each of the plurality of divided regions.

The display may display identification tags respectively matching the plurality of identification tags displayed on the setting window on the plurality of divided windows.

The display may display at least one of the maximum height from ground and the minimum height from ground of the plurality of divided regions on the camera image.

The display may display a size of a collimation region applied to at least one of the plurality of divided regions on a corresponding divided window.

The display may display a top line showing the top of a stitching region including the plurality of divided regions and a bottom line showing the bottom of the stitching region on the camera image.

The display may display the top line and the bottom line at a position corresponding to a selected protocol.

The display may display the bottom line at a lower end portion of the camera image.

According to an aspect of an exemplary embodiment, an X-ray imaging apparatus includes an X-ray source that radiates X-rays, a collimator that performs collimation of the radiated X-rays, an imaging device that captures a camera image, and a display that displays the camera image and overlays and displays at least one of a size displaying graphical object showing a size of a collimation region, a length displaying graphical object showing a length of an object, and a distance displaying graphical object showing a distance between the X-ray source and the object or a distance between the X-ray source and an X-ray detector on the camera image.

The display may display an irradiation window corresponding to the collimation region by overlaying the irradiation window on the camera image.

The display may display a size displaying graphical object showing a width of the collimation region at an upper portion of the irradiation window and may display a size displaying graphical object showing a height of the collimation region at a side portion of the irradiation window.

The X-ray imaging apparatus may further include a controller that, when a size of the irradiation window is adjusted, controls the collimator to allow the adjusted size of the irradiation window to correspond to the size of the collimation region.

When an identical X-ray imaging is performed again, the display may display together an irradiation window that has been applied to previous X-ray imaging and an irradiation window to be applied to current X-ray imaging.

The length displaying graphical object may be displayed in a form of a tool that measures a length using a plurality of scales.

The length displaying graphical object may show an absolute length of an object shown in the camera image.

The display may display a top line for designating an upper boundary of a region in which X-ray imaging will be performed and a bottom line for designating a lower boundary thereof on the camera image and, when an identical X-ray imaging is performed again, may display a top line and a bottom line that has been applied to previous X-ray imaging and a top line and a bottom line to be applied to current X-ray imaging together.

According to an aspect of an exemplary embodiment, a method for controlling an X-ray imaging apparatus includes capturing a camera image, receiving a selection related to a stitching region including a plurality of divided regions by the camera image, and displaying a setting window providing a graphical user interface for receiving a setting of an X-ray irradiation condition for each of the plurality of divided regions and the camera image in which positions of the plurality of divided regions are displayed.

The displaying may include displaying a plurality of divided windows showing positions of the plurality of divided regions by overlaying the plurality of divided windows on the camera image.

The displaying may further include displaying a plurality of identification tags respectively corresponding to the plurality of divided regions in the setting window and, when at least one of the plurality of identification tags is selected, activating a user interface of a divided region corresponding to the selected identification tag.

The displaying may further include displaying a position of the divided region corresponding to the selected identification tag on the camera image.

The displaying may further include, when at least one divided window among the plurality of divided windows displayed in the camera image is selected, activating a graphical user interface for receiving a setting of an X-ray irradiation condition of a divided region corresponding to the selected divided window.

The displaying may further include displaying a graphical object for receiving the setting of the X-ray irradiation condition by overlaying the graphical object on the camera image.

The displaying may further include displaying the graphical user interface in the setting window by synchronizing the graphical user interface with a command input through a graphical object displayed in the camera image.

The displaying may further include displaying at least one of the maximum height from ground and the minimum height from ground of the plurality of divided regions in the camera image.

According to an aspect of an exemplary embodiment, a method for controlling an X-ray imaging apparatus includes capturing a camera image, displaying the camera image, and overlaying and displaying at least one of a size displaying graphical object showing a size of a collimation region, a length displaying graphical object showing a length of an object, and a distance displaying graphical object showing a distance between an X-ray source and the object or a distance between the X-ray source and an X-ray detector on the camera image.

The displaying may further include displaying an irradiation window corresponding to the collimation region by overlaying the irradiation window on the camera image.

The displaying may further include displaying a size displaying graphical object showing a width of the collimation region at an upper portion of the irradiation window and displaying a size displaying graphical object showing a height of the collimation region at a side portion of the irradiation window.

The method may further include, when a size of the irradiation window is adjusted, controlling a collimator to allow the adjusted size of the irradiation window to correspond to the size of the collimation region.

The method may further include, when an identical X-ray imaging is performed again, displaying an irradiation window that has been applied to previous X-ray imaging and an irradiation window to be applied to current X-ray imaging together.

The length displaying graphical object may be displayed in a form of a tool that measures a length using a plurality of scales and show an absolute length of an object shown in the camera image.

The method may further include displaying a top line for designating an upper boundary of a region in which X-ray imaging will be performed and a bottom line for designating a lower boundary thereof on the camera image and, when an identical X-ray imaging is performed again, displaying a top line and a bottom line that has been applied to previous X-ray imaging and a top line and a bottom line to be applied to current X-ray imaging together.

BRIEF DESCRIPTION OF THE DRAWINGS

The above and/or other aspects will become more apparent by describing certain exemplary embodiments with reference to the accompanying drawings, in which:

FIG. 12C is a view illustrating overlapping regions between each of a plurality of divided regions;

FIGS. 12D and 12E are views illustrating an operation in which overlapping regions are automatically adjusted

FIG. 27 is a flowchart of a method for controlling an X-ray imaging apparatus according to an exemplary embodiment;

FIG. 28 is a flowchart of an example of performing the method for controlling an X-ray imaging apparatus according to an exemplary embodiment.

DETAILED DESCRIPTION

Figure 1:
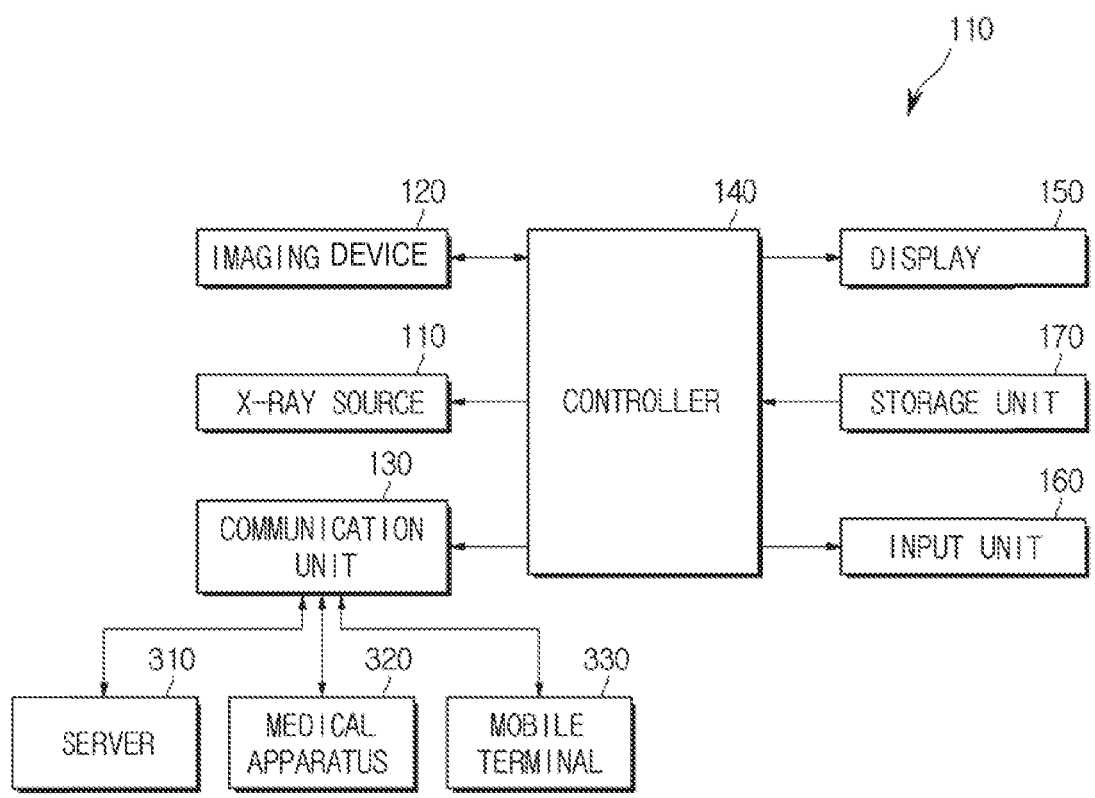
FIG. 1 is a control block diagram of an X-ray imaging apparatus according to an exemplary embodiment.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

Figure 2A:
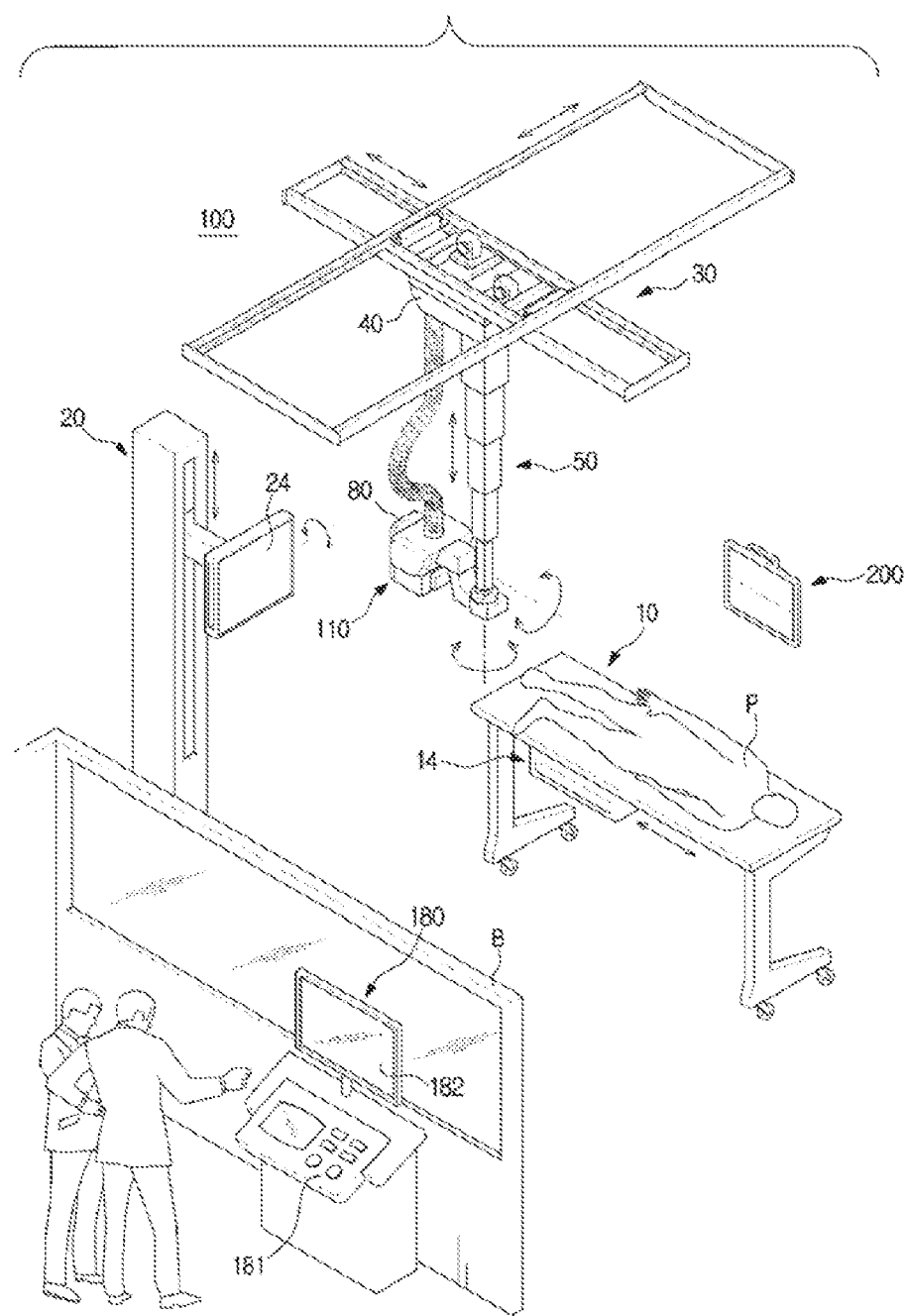
FIG. 2A is an exterior view illustrating a configuration of the X-ray imaging apparatus according to an exemplary embodiment.
Figure 2B:
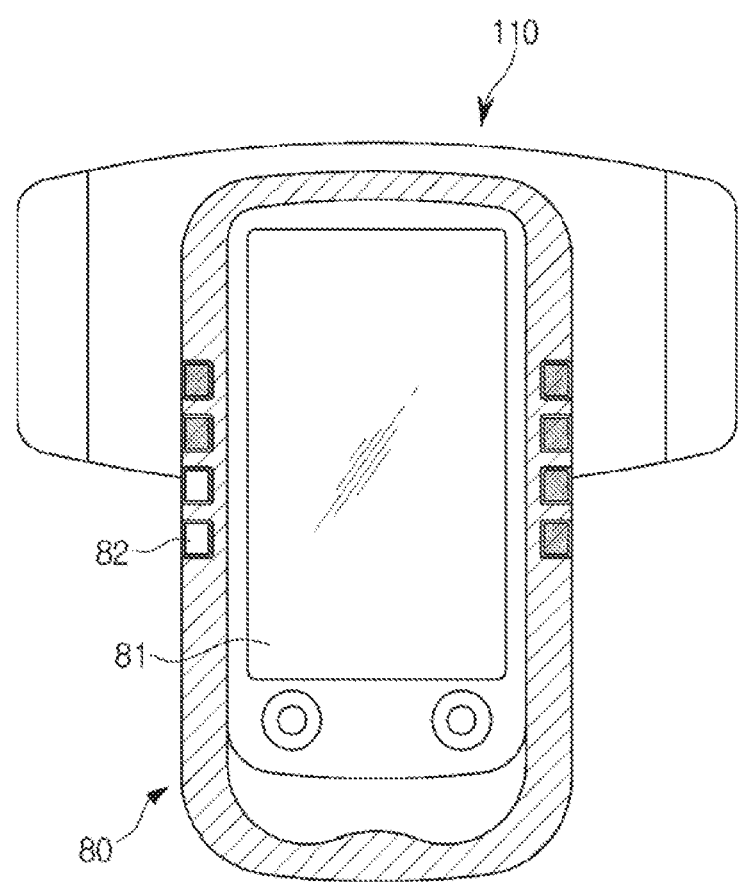
FIG. 2B is an exterior view illustrating a sub-display device mounted on an X-ray source according to an exemplary embodiment.

FIG. 1 is a control block diagram of an X-ray imaging apparatus according to an exemplary embodiment, FIG. 2A is an exterior view illustrating a configuration of the X-ray imaging apparatus according to an exemplary embodiment, and FIG. 2B is an exterior view illustrating a sub-display device mounted on an X-ray source. An exterior illustrated in FIG. 2A is an example of an X-ray imaging apparatus and relates to a ceiling type X-ray imaging apparatus in which an X-ray source is connected to a ceiling of an examination room.

Referring to FIG. 1, an X-ray imaging apparatus 100 according to an exemplary embodiment includes an X-ray source 110 that generates and radiates X-rays, an imaging device 120 that captures a camera image, a display 150 that displays the camera image captured by the imaging device 120, a screen through which an X-ray irradiation condition may be set, etc., an input unit 160 that receives control commands including a command for setting an X-ray irradiation condition from a user, a storage unit 170 that stores information related to an X-ray irradiation condition, and the like, and a controller 140 that controls an overall operation of the X-ray imaging apparatus 100.

For example, the X-ray imaging apparatus 100 may further include a communication unit 130 that communicates with an external device.

The controller 140 may control a time point at which X-rays are radiated from the X-ray source 110, an X-ray irradiation condition, etc. according to a command input by the user and may generate an X-ray image using data received from an X-ray detector 200.

For example, the controller 140 may also control a position or an orientation of mounting units 14 and 24 on which the X-ray detector 200 is mounted according to an imaging protocol and positions of an object 1.

The controller 140 may include a memory in which a program for performing the operations described above and operations to be described below is stored and a processor that executes the stored program. The controller 140 may include one processor or one microprocessor or a plurality of processors or microprocessors. In the latter case, the plurality of processors or microprocessors may be integrated in one chip or may be physically separated from each other.

When the controller 140 includes a plurality of processors and a plurality of memories, some of the memories and the processors may be provided at a work station 180 (see FIG. 2A) and the remaining memories and processors may be provided in other devices such as a sub-display device 80 (see FIG. 2A) or a moving carriage 40 (see FIG. 2A). For example, a processor provided in the work station 180 may perform controlling of image processing and the like for generating an X-ray image, and a processor provided in the sub-display device or the moving carriage may perform controlling related to a movement of the X-ray source 110 or the X-ray detector 200.

The X-ray imaging apparatus 100 may be connected to an external device (e.g., an external server 310, a medical apparatus 320, and/or a portable terminal 330 such as a smartphone, a tablet personal computer (PC), and/or a wearable device) via the communication unit 130 and transmit or receive data.

The communication unit 130 may include one or more elements that enable communicating with an external device. For example, the communication unit 130 may include at least one of a short-distance communication module, a wired communication module, and a wireless communication module. For example, the communication unit 130 may further include an inner communication module that enables communication between elements of the X-ray imaging apparatus 100.

For example, the communication unit 130 may receive a control signal from an external device and transmit the received control signal to the controller 140 to allow the controller 140 to control the X-ray imaging apparatus 100 according to the received control signal.

For example, the controller 140 may also control an external device according to the control signal from the controller 140 by transmitting the control signal to the external device via the communication unit 130. For example, the external device may process data of the external device according to the control signal from the controller 140 received via the communication unit 130. Since a program capable of controlling the X-ray imaging apparatus 100 may be installed in the external device, the program may include an instruction that executes some or all operations of the controller 140.

The program may be pre-installed in the portable terminal 330, and the program may also be downloaded and installed by a user of the portable terminal 330 from a server that provides applications. The server that provides applications may include a recording medium in which the corresponding program is stored.

Referring to FIG. 2A, a guide rail 30 may be installed on a ceiling of an examination room in which the X-ray imaging apparatus 100 is disposed, the X-ray source 110 may be connected to the moving carriage 40 moving along the guide rail 30 to move the X-ray source 110 to a position corresponding to the object 1, and the moving carriage 40 and the X-ray source 110 may be connected via a post frame 50 to adjust a height of the X-ray source 110 from ground.

Since the X-ray source 110 may be moved automatically or manually, the X-ray imaging apparatus 100 may further include a driving unit such as a motor that provides power to allow the X-ray source 110 to move when the X-ray source 110 automatically moves.

The work station 180 may be provided in a space separated, by a shielding curtain B, from a space in which the X-ray source 110 is disposed. The work station 180 may include an input unit 181 that receives a command from the user and a display 182 that displays information.

The input unit 181 may receive a command for controlling an imaging protocol, an X-ray irradiation condition, a time point at which X-rays are radiated, a position of the X-ray source 110, and the like. The input unit 181 may include a keyboard, a mouse, a touch screen, a voice recognizer, and the like.

The display 182 may display a screen for guiding an input by the user, an X-ray image, a screen showing a state of the X-ray imaging apparatus 100, etc.

Meanwhile, the display 150 and the input unit 160 described with reference to FIG. 1 may be respectively implemented with the input unit 181 and the display 182 provided in the work station 180, may also be respectively implemented with a sub-display 81 and a sub-input unit 82 provided in the sub-display device 80, and may also be implemented with a display and an input unit provided in a mobile device such as a tablet PC and a smartphone.

The X-ray detector 200 may be implemented with a fixed type X-ray detector fixed to a stand 20 or a table 10, may be detachably mounted on the mounting units 14 and/or 24, and may also be implemented with a portable X-ray detector which is usable at any position. The portable X-ray detector may be implemented as a wired type or a wireless type according to a way of transmitting data and a way of supplying power.

Since the X-ray detector 200 may also move automatically or manually, the X-ray imaging apparatus 100 may further include a driving unit such as a motor that provides power to allow the mounting units 14 and 24 to move when the X-ray detector 200 moves automatically.

The X-ray detector 200 may either be included or not included as an element of the X-ray imaging apparatus 100. In the latter case, the X-ray detector 200 may be registered in the X-ray imaging apparatus 100 by the user. For example, in both cases, the X-ray detector 200 may be connected to the controller 140 via the communication unit 130 to receive a control signal or transmit image data.

The sub-display device 80 that provides the user with information and receives a command from the user may be provided at one side of the X-ray source 110, and some or all of the functions performed by the input unit 181 and the display 182 of the work station 180 may be performed by the sub-display device 80.

When all or some of the elements of the controller 140 and the communication unit 130 are separately provided from the work station 180, the elements may be included in the sub-display device 80 provided at the X-ray source 110.

The user may input various types of information or commands related to X-ray imaging by manipulating the sub-input unit 82 illustrated in FIG. 2B or touching the sub-display 81 illustrated in FIG. 2B.

For example, the user may input a position to which the X-ray source 110 will be moved through the sub-input unit 82 or the sub-display 81.

Although FIG. 2A illustrates a fixed type X-ray imaging apparatus connected to a ceiling of an examination room, the X-ray imaging apparatus 100 may include X-ray imaging apparatuses with various structures such as a C-arm type X-ray imaging apparatus or a mobile X-ray imaging apparatus within the scope that is self-evident to those of ordinary skill in the art.

Meanwhile, the X-ray source 110 may include an X-ray tube that generates X-rays, a collimator that performs collimation of X-rays generated from an X-ray tube to adjust a region to be irradiated with the X-rays, and the imaging device 120 that captures a camera image. Since the X-ray source 110 includes an X-ray tube 111, the X-ray source 110 is also referred to as a tube head unit (THU). Hereinafter, this will be described in detail with reference to the drawings.

Figure 3A:
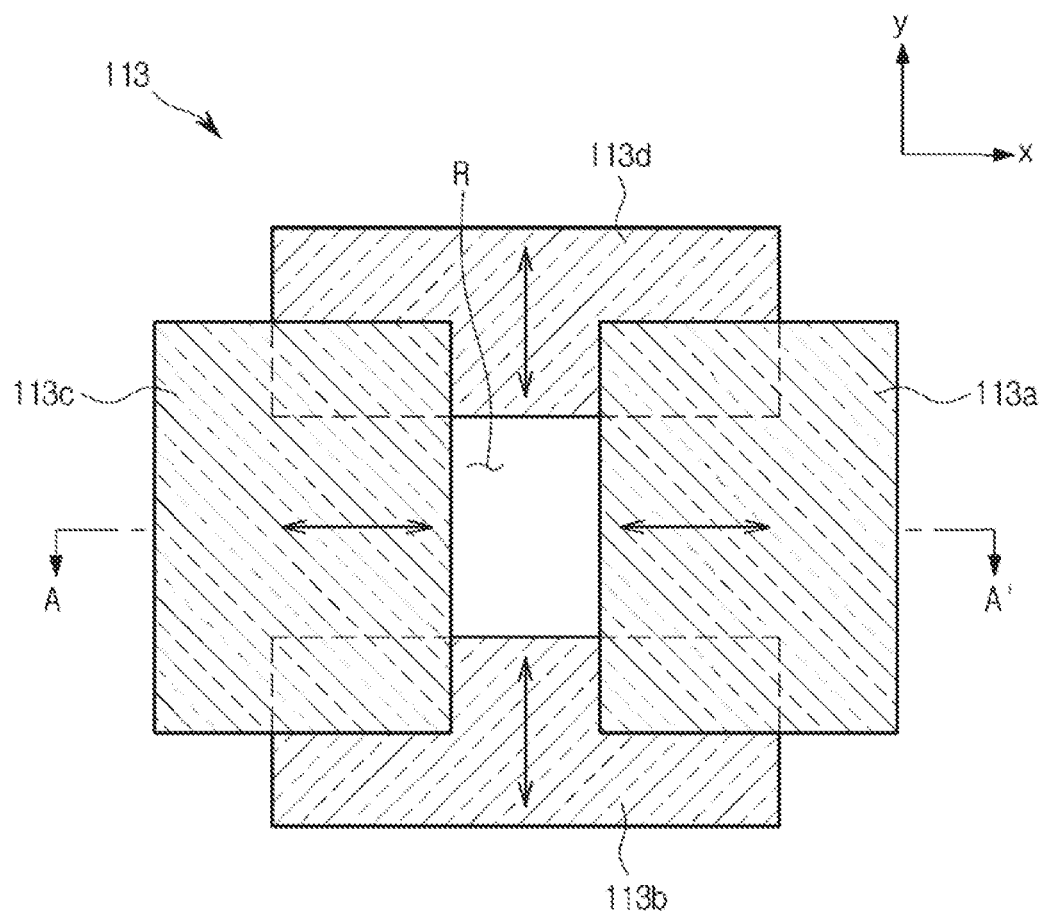
FIG. 3A is a view illustrating a configuration of a collimator included in an X-ray source according to an exemplary embodiment.
Figure 3B:
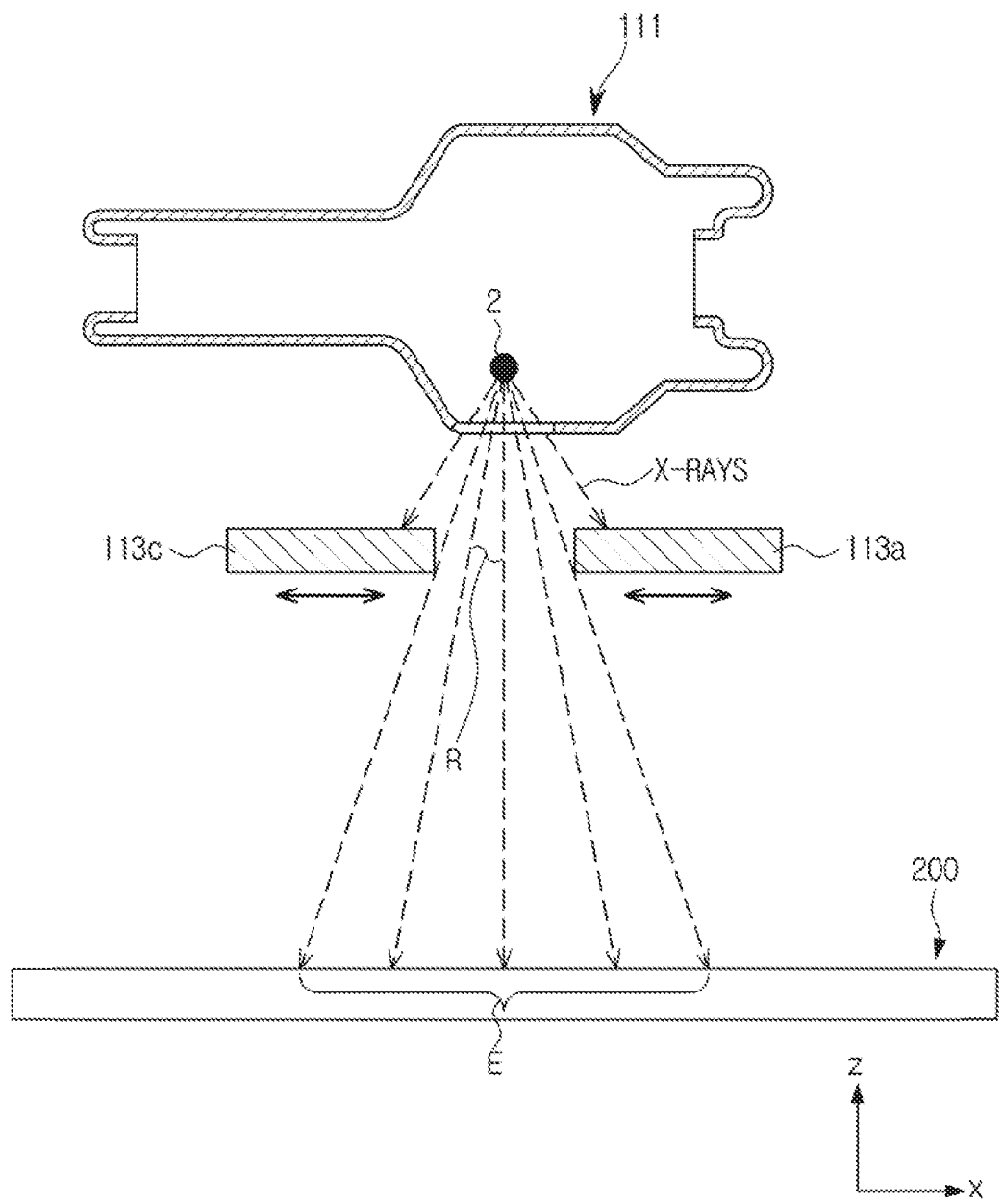
FIG. 3B is a lateral cross-sectional view of a blade taken along line A-A' in FIG. 3A.

FIG. 3A is a view illustrating a configuration of a collimator, and FIG. 3B is a lateral cross-sectional view of a blade taken along line A-A' in FIG. 3A.

Referring to FIG. 3A, a collimator 113 may include one or more movable blades 113a, 113b, 113c, and 113d, and the one or more blades may absorb X-rays by being formed of a material having a high bandgap. An irradiation range of X-rays may be adjusted as the one or more blades move, and the collimator 113 may further include a motor that provides power to each of the one or more blades.

The controller 140 calculates a movement amount of each of the one or more blades corresponding to a set X-ray irradiation region and transmits a control signal for moving the one or more blades by the calculated movement amount to the collimator 113.

For example, the collimator 113 may include four blades 113a, 113b, 113c, and 113d, each having a flat plate shape. The first blade 113a and the third blade 113c are movable in two directions along an x-axis, and the second blade 113b and the fourth blade 113d are movable in two directions along a y-axis.

For example, each of the four blades 113a, 113b, 113c, and 113d may move separately, or the first blade 113a and the third blade 113c may move together as a set, and the second blade 113b and the fourth blade 113d may move together as a set.

X-rays may be radiated through a slot R formed by the four blades, and collimation may be performed by passing X-rays through the slot R. Consequently, in an exemplary embodiment, the slot R is referred to as a collimation region, and an X-ray irradiation region signifies a region in which X-rays that have passed through the collimation region R are incident on the object 1 or the X-ray detector 200.

Referring to FIG. 3B, the collimator 113 is disposed in front of the X-ray tube 111. Here, a direction toward the front of the X-ray tube 111 signifies a direction in which X-rays are radiated. An X-ray irradiation region E of X-rays radiated from a focal point 2 of the X-ray tube 111 is limited by the collimator 113, and scattering of the X-rays is reduced.

Among the X-rays radiated from the X-ray tube 111, X-rays incident on the blades 113a, 113b, 113c, and 113d are absorbed into the blades, and X-rays that have passed through the collimation region R are incident on the X-ray detector 200. Here, a description will assume that an object does not exist.

When X-rays scatter in the form of cone beams, the X-ray irradiation region E is larger than the collimation region R. A desired range of the X-ray irradiation region E may be irradiated with X-rays by the controller 140 by adjusting the collimation region R based on a relation between the two regions.

Although the collimator 113 has been described as having four blades in a quadrilateral shape in the example above, this is merely an example that is applicable to the X-ray imaging apparatus 100, and the number or shape of blades included in the collimator 113 is not limited thereto.

Figure 4:
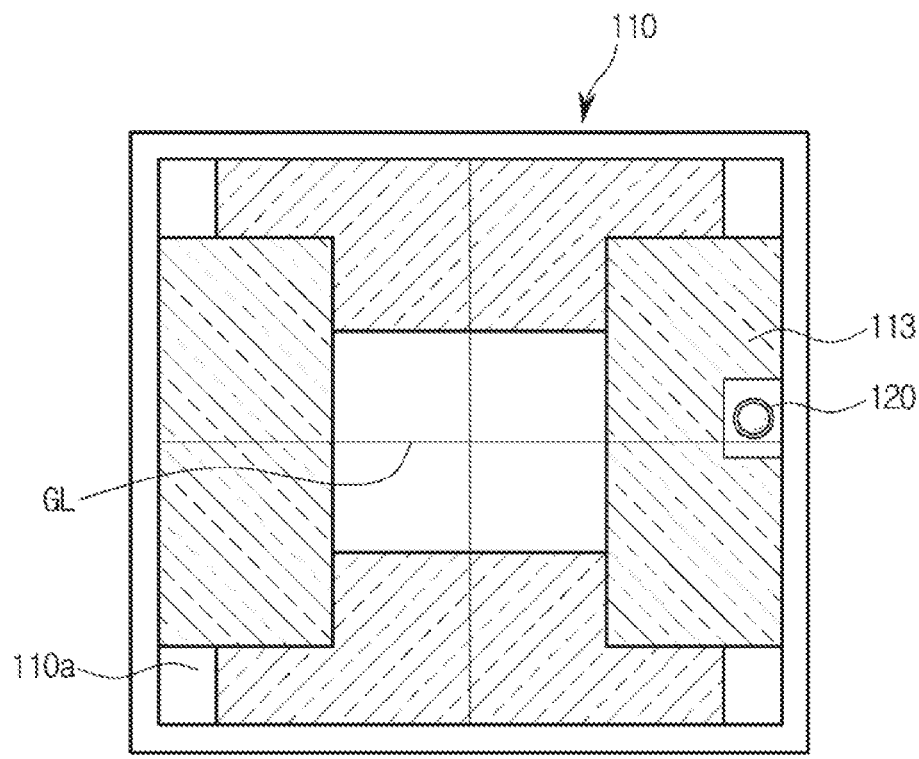
FIG. 4 shows an X-ray source viewed from the front.

FIG. 4 shows an X-ray source viewed from the front.

Referring to FIG. 4, the collimator 113 may be disposed in front of the X-ray source 110, and the imaging device 120 may be embedded in a region adjacent to the collimator 113.

The imaging device 120 may capture a video by being implemented as a camera such as a charge-coupled device (CCD) camera and a complementary metal oxide silicon (CMOS) camera. Alternatively, the imaging device 120 may also capture still images at short intervals.

While the X-ray source 110 captures an X-ray image, the imaging device 120 captures a real image. In an exemplary embodiment to be described below, an image captured by the X-ray source 110 will be referred to as an X-ray image, and an image captured by the imaging device 120 will be referred to as a camera image. The camera image may either include or not include an object. That is, the camera image may be captured while the object 1 is disposed in front of the X-ray detector 200, and the camera image may also be captured while the object 1 does not exist.

The imaging device 120 may be disposed at a position at which a portion of an object to be imaged by X-rays may be captured. For example, the imaging device 120 may be mounted on the X-ray source 110 in a direction that is the same as a direction in which X-rays are radiated from the X-ray source 110. When the imaging device 120 is mounted on the X-ray source 110, the user may more easily set settings related to an X-ray image while looking at a camera image since an offset between a region shown in the X-ray image and a region shown in the camera image is reduced. A position on which the imaging device 120 is mounted may be suitably determined within a range that minimizes the offset between the region shown in the X-ray image and the region shown in the camera image and that does not affect X-ray imaging.

Since a housing 110a may be formed in front of the collimator 113, the housing 110a may be formed with a material such as a transparent resin or glass to minimize its influence on X-rays radiated from the X-ray tube 111.

For example, a guideline GL in a cross shape may be displayed on the housing 110a. When the X-ray irradiation region E is irradiated with visible rays by a collimator lamp embedded in the X-ray source 110, a shadow of the guideline GL may be displayed at the center of the X-ray irradiation region E, and the user may intuitively recognize the position of the X-ray irradiation region E by looking at the shadow of the guideline GL.

The imaging device 120 may be mounted on an inner portion of the housing 110a as illustrated in FIG. 4. Alternatively, the imaging device 120 may also be mounted on an outer portion of the housing 110a. Here, the imaging device 120 may be mounted on a bezel provided at a circumference of the housing 110a. However, since an exemplary embodiment of the X-ray imaging apparatus 100 is not limited thereto, the imaging device 120 may be mounted on any position so long as an image of an object can be captured at the position.

For example, the imaging device 120 may also be implemented with a stereo camera. In this case, cameras may be disposed at both left and right sides in front of the X-ray source 110. When the imaging device 120 is implemented as a stereo camera, information on a depth of the camera image may be acquired, and, using the depth information, accuracy in image recognition and reliability of various types of information calculated based on the camera image may be improved.

Figure 5A:
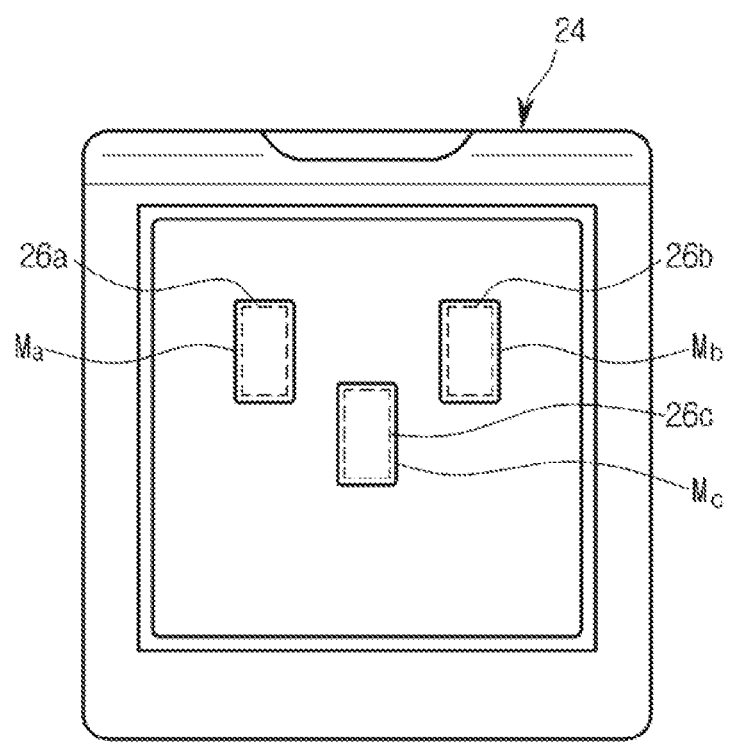
FIGS. 5A and 5B are views each illustrating an example of an automatic exposure control (AEC) sensor that may be used in the X-ray imaging apparatus according to an exemplary embodiment.
Figure 5B:
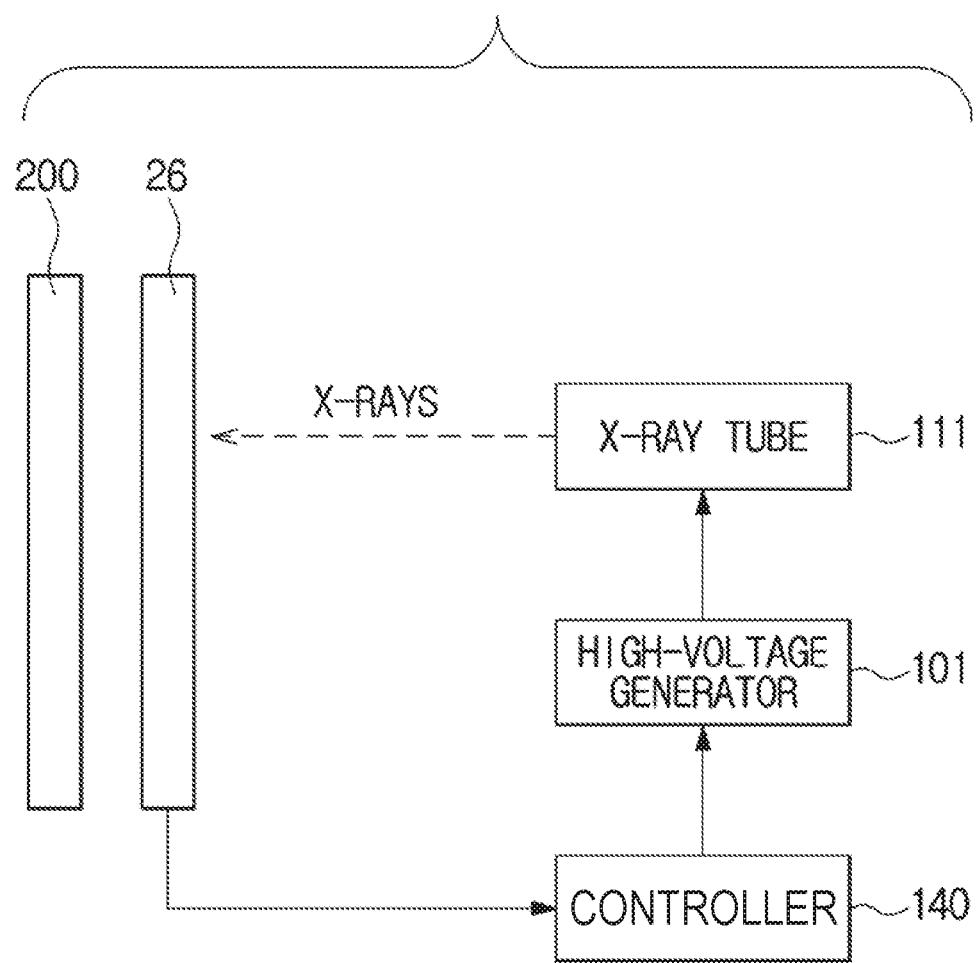

FIGS. 5A and 5B are views each illustrating an example of an automatic exposure control (AEC) sensor that may be used in the X-ray imaging apparatus according to an exemplary embodiment.

To prevent an object from being excessively irradiated with X-rays, the X-ray imaging apparatus 100 may perform AEC. For this, an AEC sensor module 26 that detects a dose of X-rays may be provided in the mounting unit 24 as illustrated in FIG. 5A. Although the AEC sensor module 26 is described using the mounting unit 24 of the stand 20 in this example, the AEC sensor module 26 may also be provided at the mounting unit 14 of the table 10.

FIG. 5A shows the mounting unit 24 viewed from the front. The AEC sensor module 26 may be provided inside the mounting unit 24 and may include a plurality of AEC sensors 26a, 26b, and 26c that independently detect a dose of X-rays. For example, each of the AEC sensors may be implemented as an ionization chamber.

The most accurate AEC is possible when an AEC sensor is disposed at the center of an X-ray imaging portion. Markers Ma, Mb, and Mc that respectively show positions of the plurality of AEC sensors 26a, 26b, and 26c may be provided at a surface of the mounting unit 24 to position the center of the X-ray imaging portion at a position corresponding to the AEC sensor or select an AEC sensor disposed at the center of the X-ray imaging portion.

Although a total of three AEC sensors, two at an upper side and one at a lower side, are illustrated as being provided in FIG. 5A, this is merely an example. Less than or more than three AEC sensors may also be provided, and the AEC sensors may also be arranged in a different way.

Referring to FIG. 5B, the AEC sensor module 26 may also be disposed in front of the X-ray detector 200. A direction toward the front of the X-ray detector 200 signifies a direction in which X-rays are incident. FIG. 5B shows the AEC sensor module 26 disposed in front of the X-ray detector 200 viewed from the side.

A current may be generated when X-rays are incident on an AEC sensor, and the AEC sensor may transmit a signal corresponding to the generated current to the controller 140. The signal transmitted to the controller 140 may be an amplified and digitized signal.

Based on the transmitted signal, the controller 140 determines whether a dose of X-rays currently incident exceeds a critical dose. When the dose of the X-rays exceeds the critical dose, a cut-off signal may be transmitted to a high-voltage generator 101 that supplies a high voltage to the X-ray tube 111 to stop generation of the X-rays.

Meanwhile, a grid that prevents X-rays from scattering may also be disposed in front of the AEC sensor module 26. Some of the X-rays radiated from the X-ray source 110 may deviate from their original path and scatter by colliding against dust particles in the air or substances forming an object before reaching the X-ray detector 200. When the scattered X-rays are incident on the X-ray detector 200, the scattered X-rays have a negative influence on the quality of an X-ray image such as degrading the contrast of an X-ray image.

The grid has a structure in which shielding substances such as lead (Pb) that absorb X-rays are arranged. Among radiated X-rays, X-rays advancing in their original direction, i.e., X-rays moving forward, pass through portions between the shielding substances and are incident on the X-ray detector 200, and scattered X-rays collide with the shielding substances and are absorbed into the shielding substances.

The shielding substances may be arranged in a linear structure and also in a cross-like structure. For example, the shielding substances may be tilted in a direction similar to that in which the X-rays are radiated and may be densely arranged or arranged in parallel.

Although not illustrated in the drawings, a driving unit that includes a motor which may mechanically move the grid may be disposed inside the mounting unit 24. Consequently, an angle or a central position of the grid may be adjusted by transmitting a control signal to the driving unit from the outside.

Meanwhile, although the AEC sensor module 26 has been described in the example as being provided at the mounting unit 24, the AEC sensor module 26 may also be integrally provided with the X-ray detector 200.

FIGS. 6 to 10 are views each illustrating an example of a screen displayed on a display.

Figure 6:
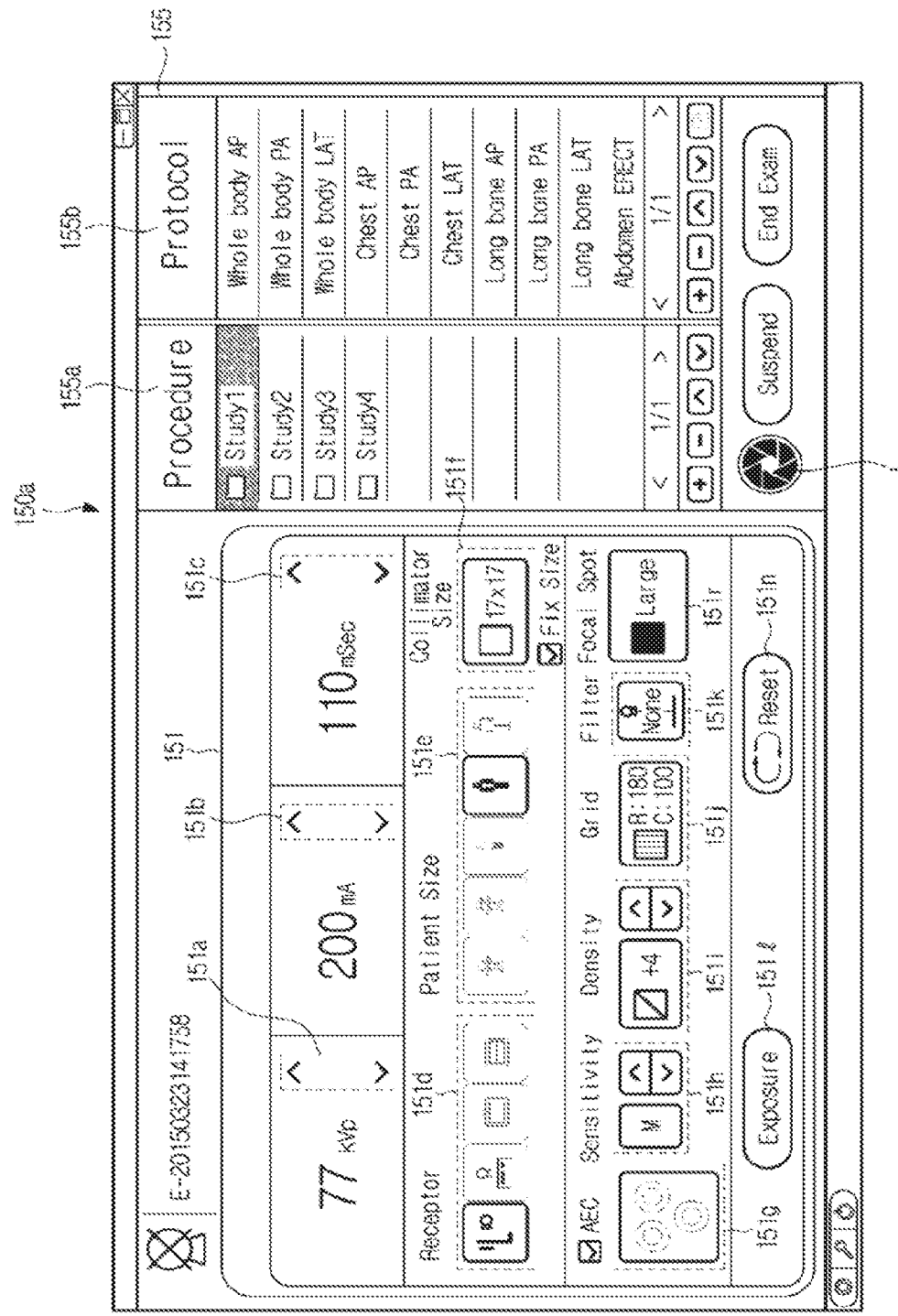
FIGS. 6, 7, 8, 9, and 10 are views each illustrating an example of a screen displayed on a display according to an exemplary embodiment.

Referring to FIG. 6, a setting window 151 for setting an X-ray irradiation condition and a work list 155 may be displayed on a screen 150a of the display 150.

The work list 155 may include a study list 155a from which a study may be selected and a protocol list 155b from which an imaging protocol may be selected. A study may refer to a set of X-ray images related to each other. When any one study is selected from the study list 155a, the protocol list 155b from which an imaging protocol to be applied to the selected study may be selected is displayed.

An X-ray imaging region may change for each imaging protocol, and a suitable X-ray irradiation condition may change for each X-ray imaging region. An imaging protocol may be determined according to a portion to be imaged by X-rays, a posture of an object, and the like. For example, imaging protocols may include whole body anterior-posterior (AP), whole body PA, and whole body lateral (LAT), may also include chest AP, chest PA, and chest LAT, and may also include long bone AP, long bone PA and long bone LAT for long bones such as a leg. For example, imaging protocols may also include abdomen erect imaging.

A graphical user interface (GUI) may be displayed so that the user can intuitively control the X-ray imaging apparatus 100. The GUI may include a plurality of graphical objects which may be used to set various X-ray irradiation conditions. In an exemplary embodiment, objects such as buttons and icons displayed on the display 150 to provide information or be used in receiving a control command from a user may all be referred to as graphical objects.

Since the graphical objects are used in receiving a command for setting an X-ray irradiation condition from the user, the graphical objects may be implemented with buttons respectively corresponding to the various X-ray irradiation conditions.

For example, the buttons may include a tube voltage setting button 151a for receiving a tube voltage setting, a tube current setting button 151b for receiving a tube current setting, and an exposure time setting button 151c for receiving an X-ray exposure time setting, and a currently set tube voltage, tube current, and exposure time may be respectively displayed at side surfaces of the buttons. The user may select each of the buttons to set an X-ray irradiation condition to have a desired value. The buttons may be selected by clicking or touching depending on a type of the input unit 160.

According to an exemplary embodiment, the tube voltage setting button 151a may separately include a button for increasing a tube voltage and a button for decreasing the tube voltage, the tube current setting button 151b may separately include a button for increasing a tube current and a button for decreasing the tube current, and the exposure time setting button 151c may separately include a button for increasing an exposure time and a button for decreasing the exposure time.

For example, a capture position setting button 151d for receiving a setting related to whether X-ray imaging will be performed at the stand 20 or at the table 10 or whether the portable X-ray detector will be used, an object size selection button 151e for receiving a selection related to a size of a patient, and a collimator setting button 151f for receiving a setting related to a size of the collimator may be further displayed on the setting window 151.

For example, an AEC selection button 151g for receiving a selection related to an AEC sensor, a sensitivity setting button 151h for receiving a setting related to sensitivity, a density setting button 151i for receiving a setting related to density, a grid selection button 151j for receiving a selection related to the grid, a filter selection button 151k for receiving a selection related to a filter, a focal point selection button 151r for receiving a selection related to a size of a focal point, etc. may be further displayed in the setting window 151.

The buttons may be implemented as shapes formed of pictures, letters, symbols, etc. The user may select any one shape by moving a cursor and clicking the corresponding shape or touching and manipulating the shape. Accordingly, a setting corresponding to the selected shape may be changed.

Meanwhile, when a selection related to a size of a patient is input, an X-ray irradiation condition mapped as a default for the corresponding size may be set. For this, the storage unit 170 may store a database in which an X-ray irradiation condition for each of a plurality of sizes of a patient is mapped.

When the user selects a size of a patient, X-ray irradiation conditions such as a tube voltage, a tube current, and an exposure time mapped as a default for the corresponding size are displayed in the setting window 151. The mapped X-ray irradiation conditions may be applied without change, or the user may select a button corresponding to each of the X-ray irradiation conditions and set each of the X-ray irradiation conditions again according to the method described above. Here, the user may set each of the X-ray irradiation conditions again with reference to default X-ray irradiation conditions displayed in the setting window 151.

For example, an X-ray imaging region may change for each imaging protocol, and a suitable X-ray irradiation condition may change for each X-ray imaging region. Consequently, an X-ray irradiation condition may be differently set according to an imaging protocol selected from the work list 155 and a size of an object selected from the setting window 151.

The types and arrangements of the graphical objects displayed in the setting window 151 described above are all illustrative. Some of the above may be omitted according to a designer's choice, a graphical object other than the above for changing a setting may be further provided, and the above may be provided in arrangements different from those in the example described above.

An "exposure" button 151l that receives a command related to starting X-ray imaging and a reset button 151n for initializing with preselected settings may be displayed at a lower end of the setting window 151. The user may select the "exposure" button 151l to perform X-ray imaging and may select the reset button 151n when attempting to initialize settings.

Meanwhile, to obtain information required for performing X-ray imaging, the imaging device 120 may capture a camera image while the X-ray source 110 is facing the X-ray detector 200. In this case, the X-ray detector 200 or the mounting units 14 and 24 on which the X-ray detector 200 is mounted may be covered by the object 1 and not be shown in the camera image. Conversely, when a camera image is captured while the object 1 is not disposed in front of the X-ray detector 200, the X-ray detector 200 or the mounting units 14 and 24 on which the X-ray detector 200 is mounted may be shown in the camera image. A captured camera image 152 may be displayed at one side of the setting window 151 as illustrated in FIG. 7.

Figure 7:
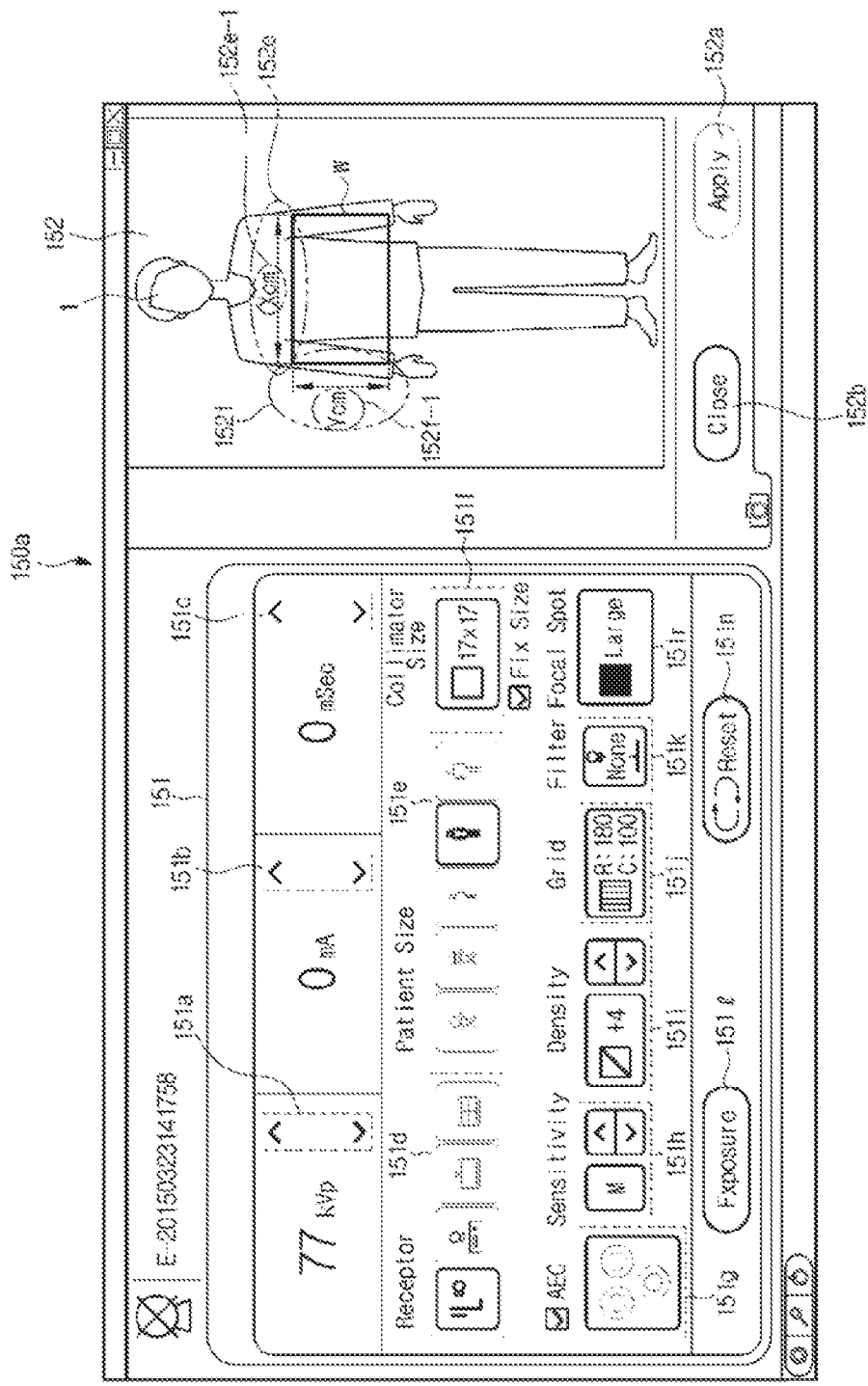

The work list 155 illustrated in FIG. 6 and the camera image 152 illustrated in FIG. 7 may be switched with each other. The work list 155 may be switched to the camera image 152 when a camera image button I is selected while the work list 155 is displayed, and the camera image 152 may be switched to the work list 155 when a close button 152b is selected while the camera image 152 is displayed. Alternatively, when the selected imaging protocol needs stitching imaging, the work list 155 may be switched to the camera image 152 automatically and then screens regarding stitching imaging described below may be displayed.

Figure 8:
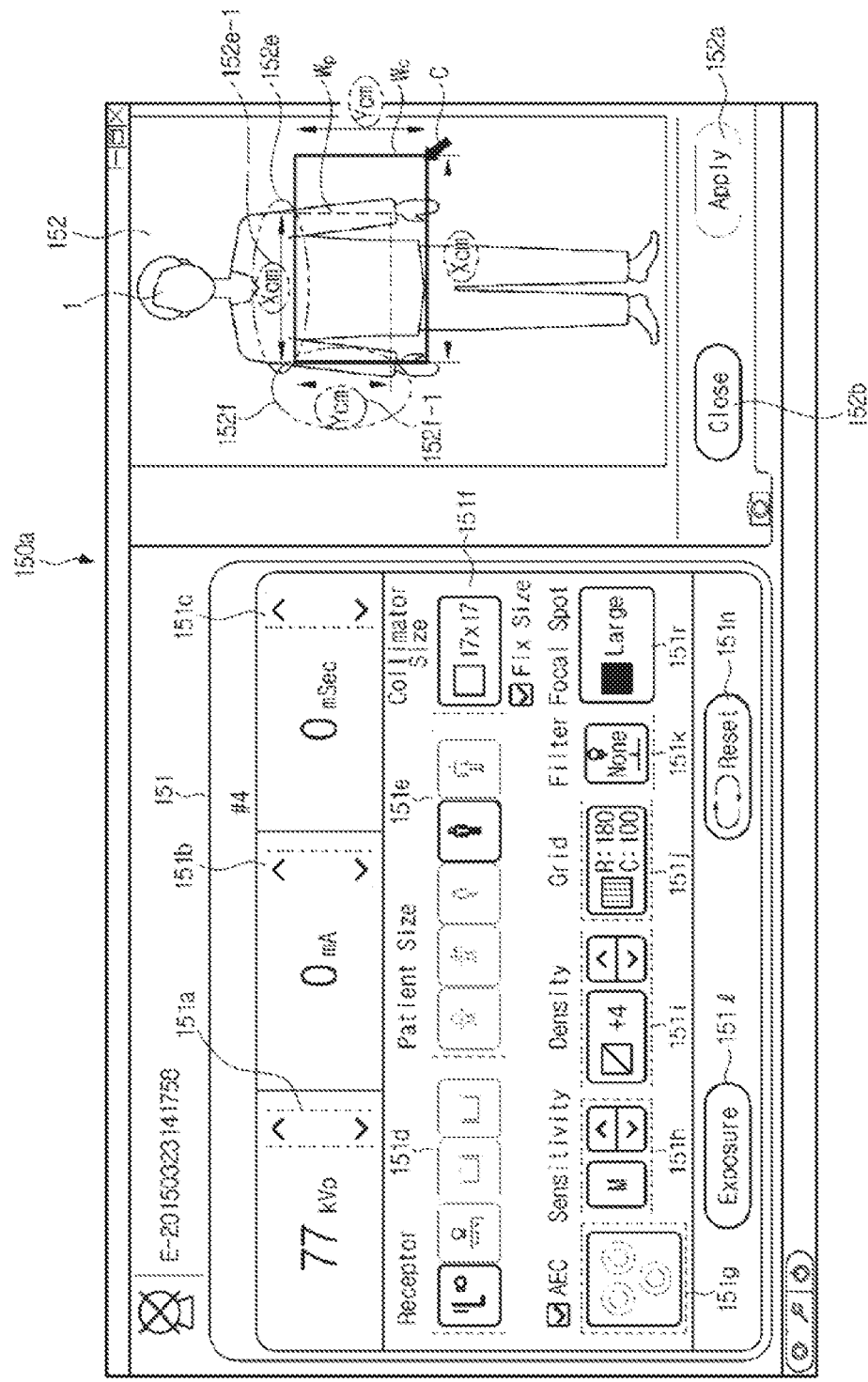
Figure 9:
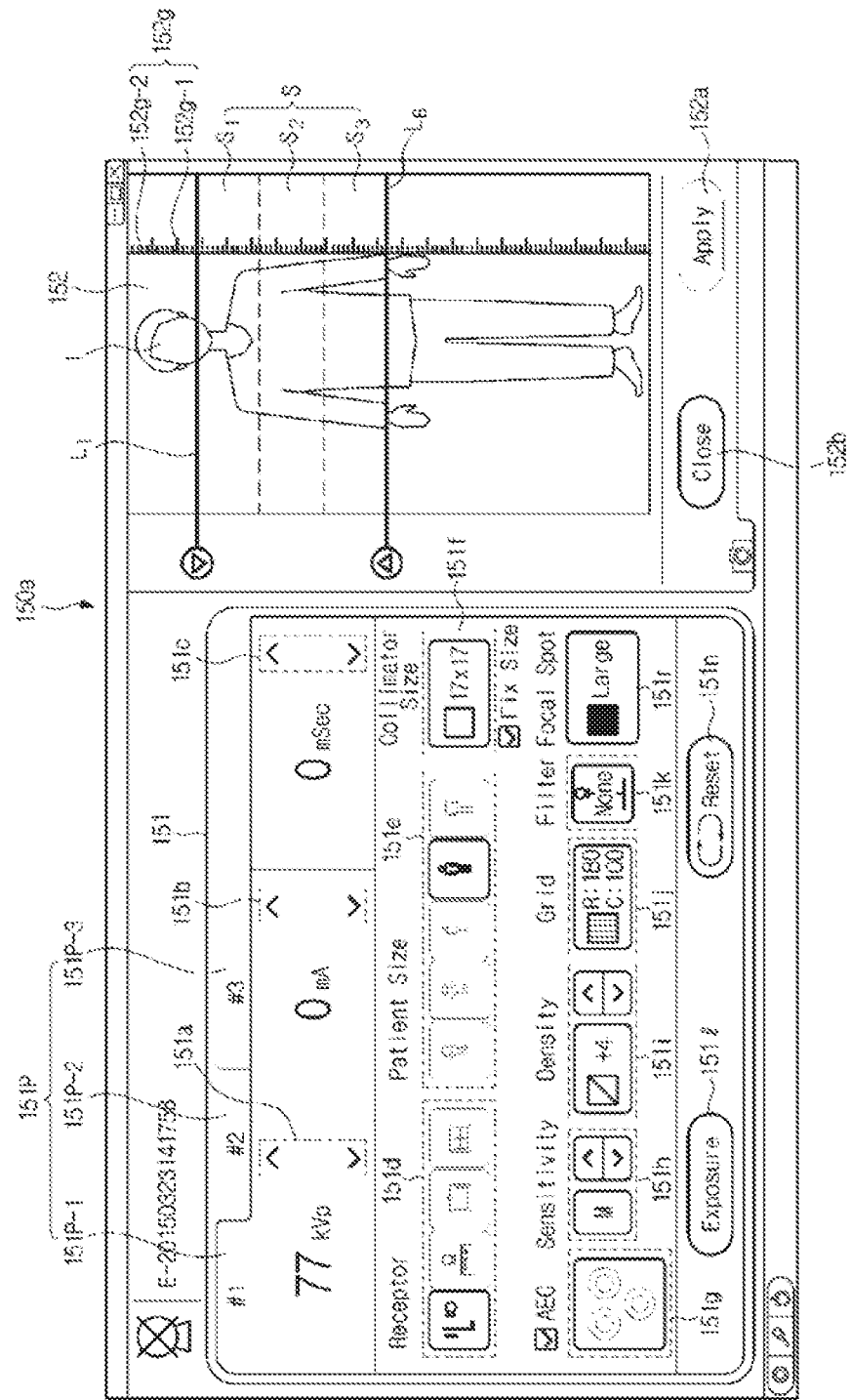

Referring to FIGS. 7 to 9, graphical objects showing various types of information may be displayed by being overlaid on the camera image 152. The graphical objects showing various types of information may include, for example, size displaying graphical objects 152e and 152f showing a size of the collimation region R, a length displaying graphical object 152g showing the length of the object 1, and a distance displaying graphical object 152h showing a distance between the X-ray source 110 and the X-ray detector 200 or a distance between the X-ray source 110 and the object 1.

The user may control various types of settings related to an operation of the X-ray imaging apparatus 100 with reference to the graphical objects displayed by on the camera image 152.

For example, as illustrated in FIG. 7, an irradiation window W showing a region on which X-rays that have passed through the collimation region will be incident, i.e., an X-ray irradiation region, may be displayed by being overlaid on the camera image 152, and the user may adjust the size of the irradiation window W by dragging at least one of a plurality of a boundary lines that form the irradiation window W or dragging at least one of a plurality of vertices forming the irradiation window W.

Here, the size of the irradiation window W corresponds to the size of the collimation region. However, since a size of an image shown on the display 150 is different from an actual size, it is difficult to accurately adjust the size of the irradiation window W to fit a capture region.

Consequently, the display 150 may display the size displaying graphical objects 152e and 152f illustrating information related to the size of the collimation region at a region adjacent to the irradiation window W.

For example, the size displaying graphical object 152e displayed at an upper portion of the irradiation window W may show the width of the collimation region with a numerical value 152e-1, and the size displaying graphical object 152f displayed at a side portion of the irradiation window W may show the height of the collimation region with a numerical value 152f-1.

Alternatively, the size of the X-ray irradiation region E may also be directly shown. In this case, the controller 140 may calculate the size of the X-ray irradiation region E based on information such as the distance between the X-ray source 110 and the X-ray detector 200, the size of the collimation region, and the distance between the X-ray tube 111 and the slot R of the collimator 113.

The user may refer to size information shown by the size displaying graphical object 152f for changing the size of the collimation region. To change the size of the collimation region, the boundary lines or vertices of the irradiation window W may be dragged as described above or a section in which the camera image 152 is displayed or a surrounding portion thereof may be touched or clicked to allow an input window (not shown) for changing the height or width of the collimation region to be displayed. When the input window is displayed, a numerical value of a desired height or width may be input to adjust the size of the collimation region.

For example, when a captured X-ray image does not include the whole portion desired to be imaged and thus imaging is performed again, the user may refer to the size information provided by the size displaying graphical object 152e to determine how much larger the imaging region has to be compared to the previous imaging.

For example, to guide the re-imaging, a previous irradiation window Wp corresponding to the size of the collimation region that has been applied to the previous imaging and a current irradiation window We to be applied to the re-imaging may be displayed together on the camera image 152 as illustrated in FIG. 8. The previous irradiation window Wp may remain displayed even when the user changes the size of the current irradiation window Wc for the re-imaging, and the user may refer to the displayed previous irradiation window Wp to determine an amount by which the size of the collimation region will be increased. Here, the previous irradiation window Wp and the current irradiation window Wc may be distinguished from each other by displaying the previous irradiation window Wp with a dotted line or displaying the previous irradiation window Wp to be blurrier than the current irradiation window Wc.

An "apply" button 152*a* for applying the adjusted size of the collimation region to X-ray imaging and a "close" button 152*b* to stop displaying the camera image 152 may be provided at the lower end of the camera image 152. For example, a cancel button (not illustrated) for cancelling various types of applied settings may also be provided at the lower end of the camera image 152. The user may select at least one of the "apply" button 152*a*, the "close" button 152*b*, and the cancel button, and a command corresponding to the user's selection may be input and transmitted to the controller 140.

When the "apply" button 152*a* is selected, a control command corresponding to the adjusted size of the collimation region is transmitted to the collimator 113, and the collimator 113 moves the blades 113*a*, 113*b*, 113*c*, and 113*d* according to the transmitted control command to adjust the size of the collimation region.

Meanwhile, when stitching imaging is performed, a top line $L_T$ and a bottom line $L_B$ may be displayed by being overlaid on the camera image 152, as illustrated in FIG. 9. The top line $L_T$ may show the top of the stitching region, and the bottom line $L_B$ may show the bottom of the stitching region. The stitching imaging may be performed in a region between the top line $L_T$ and the bottom line $L_B$.

The top line $L_T$ and the bottom line $L_B$ may be initially displayed at any position on the camera image 152 or, when an imaging protocol is selected, may be displayed at positions corresponding to the selected imaging protocol.

When the top line $L_T$ and the bottom line $L_B$ are displayed at any position on the camera image 152, the bottom line $L_B$ may be disposed at a lower end portion of the camera image 152. Since an object's toe is disposed at the lower end portion of the camera image 152 regardless of the size of the object, a work load of the user may be reduced when the bottom line $L_B$ is disposed at the lower end portion of the camera image 152 since the user does not have to manipulate the input unit to move the bottom line $L_B$.

When the top line $L_T$ and the bottom line $L_B$ are displayed at positions corresponding to an imaging protocol, the controller 140 may perform image processing such as applying an object recognition algorithm to the camera image 152 to recognize a portion corresponding to the imaging protocol.

The user may drag at least one of the top line $L_T$ and the bottom line $L_B$ to change a position thereof. For example, the user may drag and move at least one of the top line $L_T$ and the bottom line $L_B$ upward or downward.

For example, a length displaying graphical object 152*g* showing an absolute length of an object shown in the camera image may be displayed by being overlaid on the camera image 152.

Specifically, the length displaying graphical object 152*g* is provided to allow the user to easily recognize the length of the object 1 displayed on the camera image 152 or a length of each of the divided regions $S_1$, $S_2$, and $S_3$ within the camera image 152. Here, the divided regions $S_1$, $S_2$, and $S_3$ are regions divided from the entire or partial region S of the camera image 152, and the partial region of the camera image 152 may include the region between the top line $L_T$ and the bottom line $L_B$.

The length displaying graphical object 152*g* may be displayed in the form of a tool that measures a length using a plurality of scales, e.g., a ruler. The scales are indices for discretely showing a length and may include first scales 152*g*-1 which are relatively long and second scales 152*g*-2 which are relatively short.

The first scales 152*g*-1 are disposed in equal intervals, and likewise, the second scales 152*g*-2 are also disposed in equal intervals. A plurality of second scales 152*g*-2, e.g., four or nine second scales 152*g*-2, are disposed between each of the first scales 152*g*-1.

For example, at a region adjacent to a scale, a length shown by the corresponding scale may be displayed as a numerical value. The displayed numerical value may show the actual length, i.e., an absolute length, of the object. Here, the reference object is the object 1. A scale between a size in real space and a size in the camera image 152 may be reflected in the intervals between the scales.

The controller 150 may calculate the intervals between the scales included in the length displaying graphical object 152*g* and numerical values respectively shown by the scales based on a source-to-object distance (SOD) between the object 1 and the X-ray source 110 or a source-to-image distance (SID) between the X-ray detector 200 and the X-ray source 110. For example, when the SOD or SID changes due to a movement of the X-ray source 110, the controller 140 may calculate the change in real time and update the intervals between the scales and the numerical values respectively shown by the scales based on the change. The updated intervals between the scales and the numerical values respectively shown by the scales may be reflected in the length displaying graphical object 152*g* displayed by being overlaid on the camera image 152.

The user may easily estimate the length of the object 1 displayed on the camera image 152 with reference to the length displaying graphical object 152*g*. For example, the user may easily recognize an absolute height or relative height of the whole stitching region S or each of the divided regions $S_1$, $S_2$, and $S_3$ within the whole stitching region S with reference to the length displaying graphical object 152*g*.

For example, as in the example described above, when a captured X-ray image does not include the whole portion desired to be imaged and thus imaging is performed again, the user may refer to length information provided by the length displaying graphical object 152*g* to determine how much larger the imaging region has to be compared to the previous imaging For example, to guide the re-imaging, a previous top line $L_T$ and a previous bottom line $L_B$ that has been applied to the previous imaging and a current top line $L_T$ and a current bottom line $L_B$ to be applied to the re-imaging may be displayed by being overlaid on the camera image 152 together. The previous top line $L_T$ and the previous bottom line $L_B$ may remain to be displayed even when the user changes positions of the current top line $L_T$ and the current bottom line $L_B$ for the re-imaging, and the user may determine positions of the current top line $L_T$ and the current bottom line $L_B$ with reference to the displayed previous top line $L_T$ and previous bottom line $L_B$ and the length displaying graphical object 152*g*. Here, the previous top line $L_T$ and the previous bottom line $L_B$ may be distinguished from the current top line $L_T$ and the current bottom line $L_B$ by displaying the previous top line $L_T$ and the previous bottom line $L_B$ with dotted lines or displaying the previous top line $L_T$ and the previous bottom line $L_B$ to be blurrier than the current top line $L_T$ and the current bottom line $L_B$.

Figure 10:
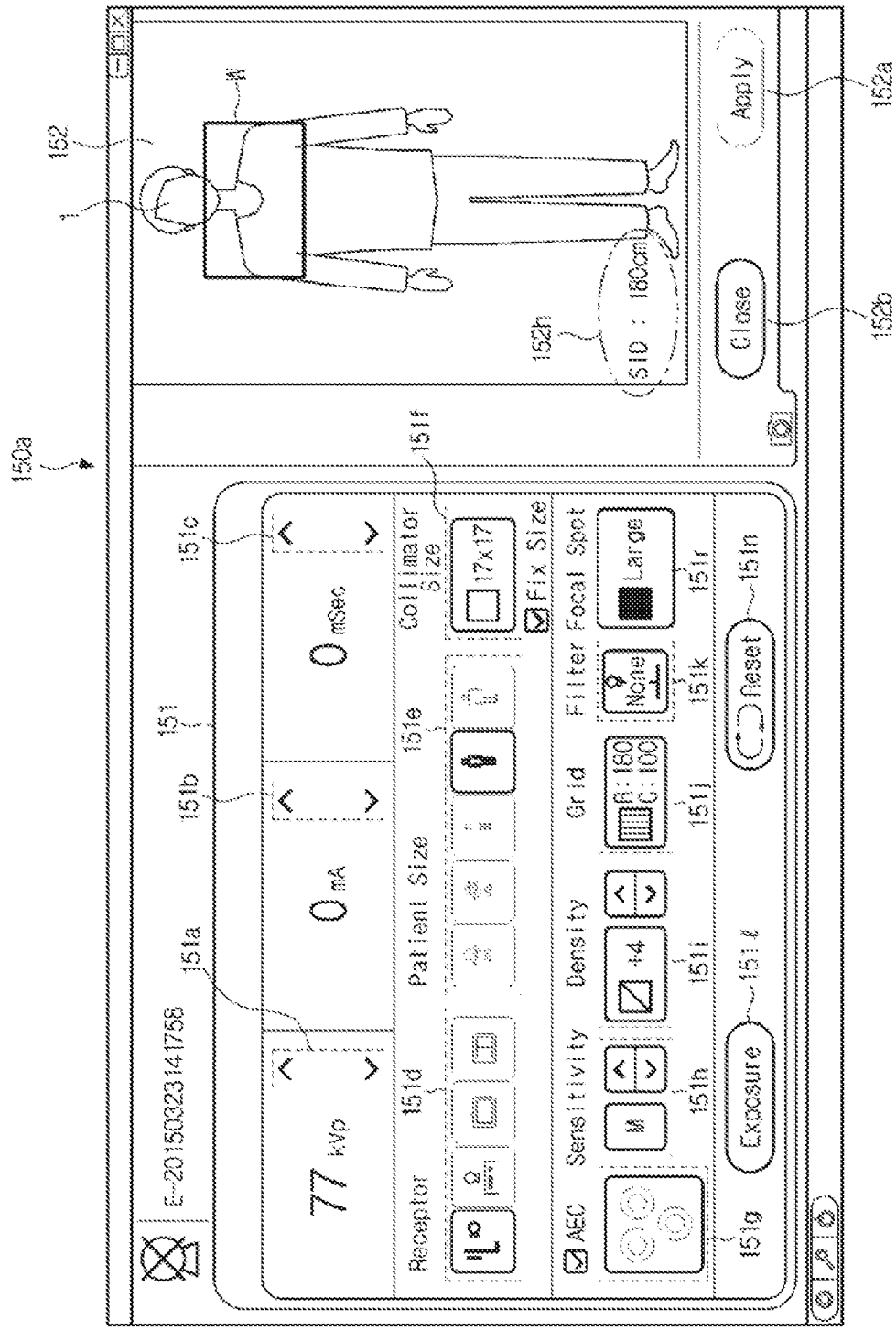

For example, a distance displaying graphical object 152h may be displayed by being overlaid on the camera image 152 as illustrated in FIG. 10.

The distance displaying graphical object 152h shows the SID or SOD.

The distance displaying graphical object 152h may be overlaid and displayed at one point of the camera image 152, e.g., at a lower left end of the camera image 152. The distance displaying graphical object 152h may show the SID or SOD using letters, symbols, or numbers.

When the user touches or clicks a region in which the distance displaying graphical object 152h is displayed or a surrounding portion thereof, an input window (not illustrated) for adjusting the SID or SOD may be displayed. The user may directly input values in the input window or input a value of a desired distance by clicking or touching. When the user inputs a predetermined value, the controller 140 may move at least one of the X-ray source 110 and the X-ray detector 200 according to the input value.

Hereinafter, several examples of a method for measuring a distance between the X-ray source 110 and the X-ray detector 200 will be described. Although only the method for measuring a distance between the X-ray source 110 and the X-ray detector 200 will be described below, a distance between the object 1 and the X-ray source 110 may also be measured using the same or a similar method.

Figure 11A:
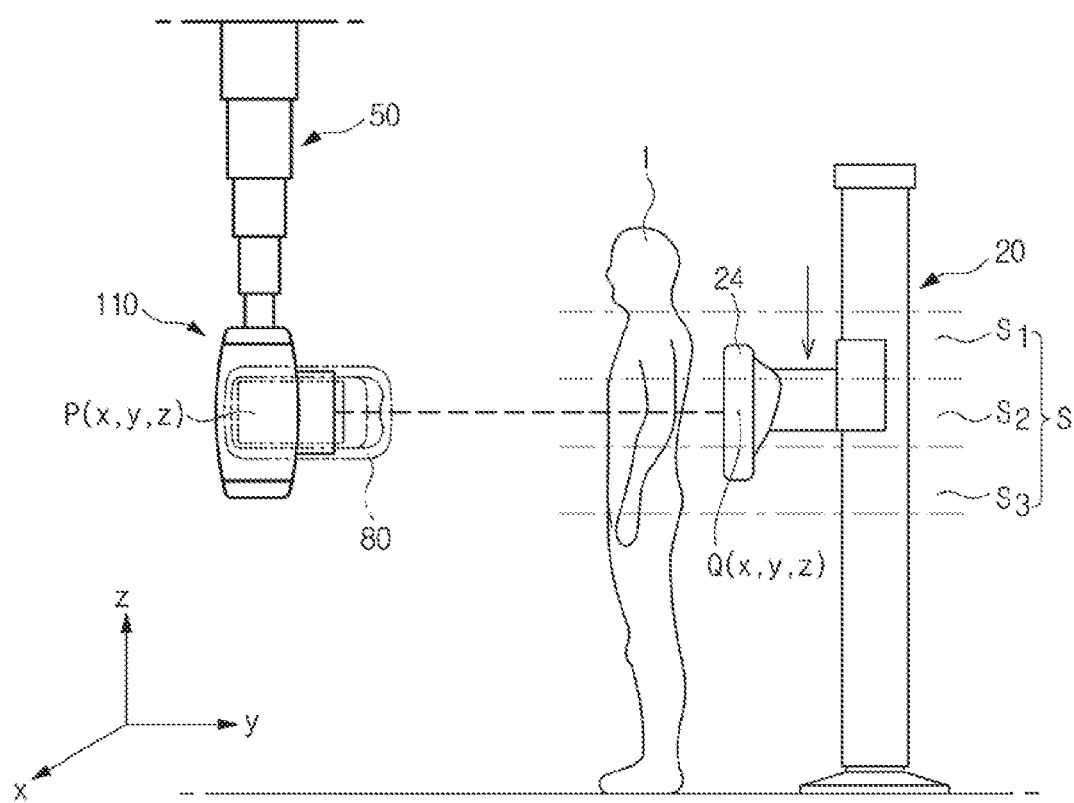
FIGS. 11A, 11B, and 11C are views for describing an example of a method for measuring a distance between an X-ray detector and an X-ray source according to an exemplary embodiment.
Figure 11B:
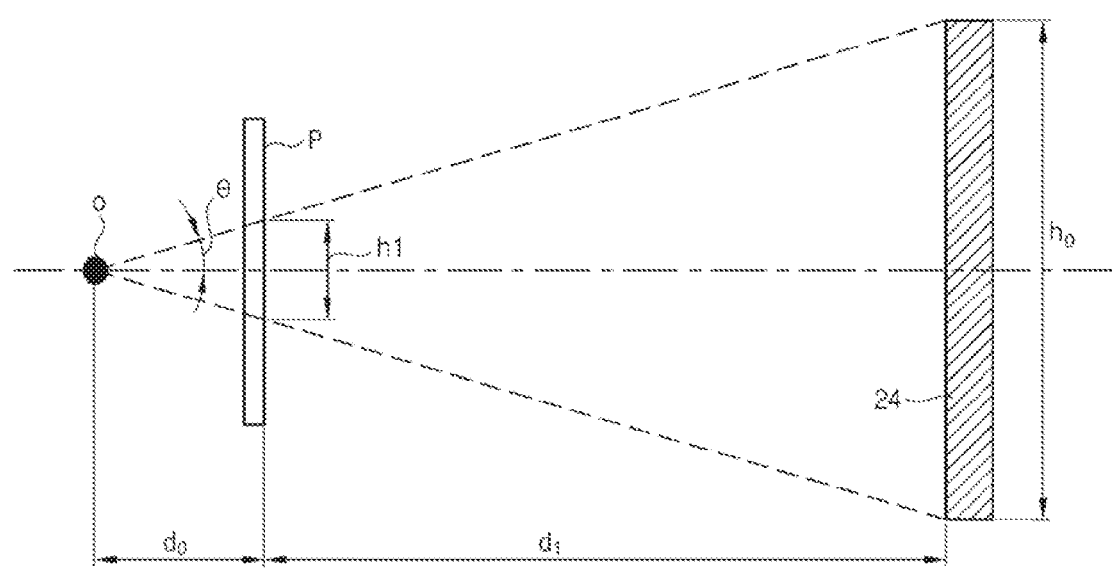
Figure 11C:
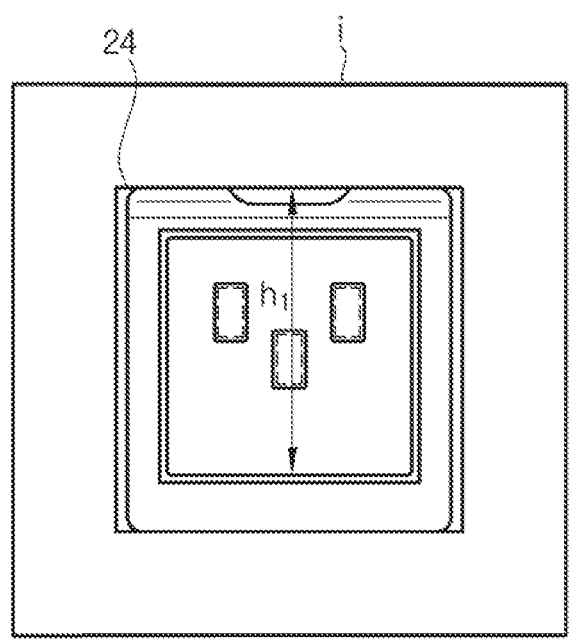

FIGS. 11A to 11C are views for describing an example of a method for measuring a distance between an X-ray detector and an X-ray source.

Referring to FIG. 11A, when moving the X-ray source 110 and the X-ray detector 200 is completed, the controller 140 may determine a position P of the X-ray source 110 and a position Q of the X-ray detector 200. In this case, the controller 140 may determine the position P of the X-ray source 110 or the position Q of the X-ray detector 200 using an encoder that measures a number of rotations of a motor used in a movement of the X-ray source 110 and a movement of the X-ray detector 200 or using a separate position detector, e.g., an infrared sensor.

The position P of the X-ray source 110 and the position Q of the X-ray detector 200 may be expressed using predetermined coordinates, and the controller 140 may compute a distance between the X-ray source 110 and the X-ray detector 200 using coordinates P(x,y,z) of the position P of the X-ray source 110 and coordinates Q(x,y,z) of the position Q of the X-ray detector 200.

In a detailed example, the controller 140 may compute a difference between the coordinates P(x,y,z) of the position P of the X-ray source 110 and the coordinates Q(x,y,z) of the position Q of the X-ray detector 200 and compute a square root of a sum of squares of the computed differences to acquire the distance between the X-ray source 110 and the X-ray detector 200.

In another example, according to FIG. 11B, visible rays reflected from a surface of the mounting unit 24 pass through a lens of the imaging device 120 and are incident on an image pickup surface P formed by an image pickup device. The lens may focus the visible rays passing therethrough to a predetermined focal point o. Light incident on the image pickup surface P is converted into an electrical signal by the image pickup device, and converted electrical signals may be combined to acquire an image i corresponding to the image pickup surface P. The mounting unit 24 may be shown in the acquired image i as illustrated in FIG. 11C.

In this case, the distance between the X-ray detector 200 and the X-ray source 100 may be acquired using a numerical value, e.g., a height h1 or width, related to the mounting unit 24 shown in the image i. Specifically, since a distance d0 between the image pickup surface P and the focal point o is a value given according to a hardware feature or a software feature of the imaging device 120, e.g., a camera device, and the height h1 of the mounting unit 24 in the image pickup surface P may also be acquired by being directly measured, an angle θ between a line connecting an upper end of the mounting unit 24 in the image pickup surface P to the focal point o and a line connecting the center of the mounting unit 24 in the image pickup surface P to the focal point o may be computed.

Meanwhile, since the actual height h0 of the mounting unit 24 is also a given value, a distance d0+d1 between the focal point o and the mounting unit 24 may be computed using a half h0/2 of the actual height h0 of the mounting unit 24 and the computed angle θ, and a distance d1 between the image pickup surface P and the mounting unit 24 may be computed and acquired using the computed distance d0+d1 between the focal point o and the mounting unit 24. The distance between the X-ray detector 200 and the X-ray source 110 is acquired since the distance d1 between the image pickup surface P and the mounting unit 24 is substantially or almost the same as the distance between the X-ray detector 200 and the X-ray source 110.

The above-described methods of acquiring the distance between the X-ray detector 200 and the X-ray source 110 are non-limiting examples only, and the distance between the X-ray detector 200 and the X-ray source 110 may be acquired using other appropriate methods.

Information on the distance between the X-ray detector 200 and the X-ray source 110 acquired as above may be provided to the user as described above.

Any one of the graphical objects 152e, 152f, 152g, and 152h described above may be exclusively displayed or all or several graphical objects 152e, 152f, 152g, and 152h may be displayed together on the screen 150a of the display 150. Types of the graphical objects being displayed, positions at which the graphical objects are displayed, and whether a graphical object is solely displayed, etc. may be determined in various ways according to predefined settings or manipulation by the user.

Meanwhile, when X-ray imaging portion of the object is larger than the X-ray irradiation region E or a detection region in which the X-ray detector 200 may detect X-rays, the X-ray imaging portion may be divided into a plurality of regions, X-ray imaging may be separately performed for each of the plurality of divided regions. Obtaining a single entire X-ray image by dividing the X-ray imaging portion into a plurality of regions, imaging each of the plurality of divided regions and stitching the X-ray images for each of the plurality of divided regions may be referred to by various terms such as panoramic imaging, stitching imaging, segmentation imaging, etc. For convenience of description, such imaging (panoramic imaging, stitching imaging, segmentation imaging, etc.) will be referred to as stitching imaging, in the exemplary embodiments. Also, each of the X-ray images for each of the divided regions will be referred to as divided X-ray image and each of the X-ray imaging for each of the divided regions will be referred to as divided imaging. Furthermore, one image generated by stitching together a plurality of divided X-ray images will be referred to as a stitched image.

Figure 12A:
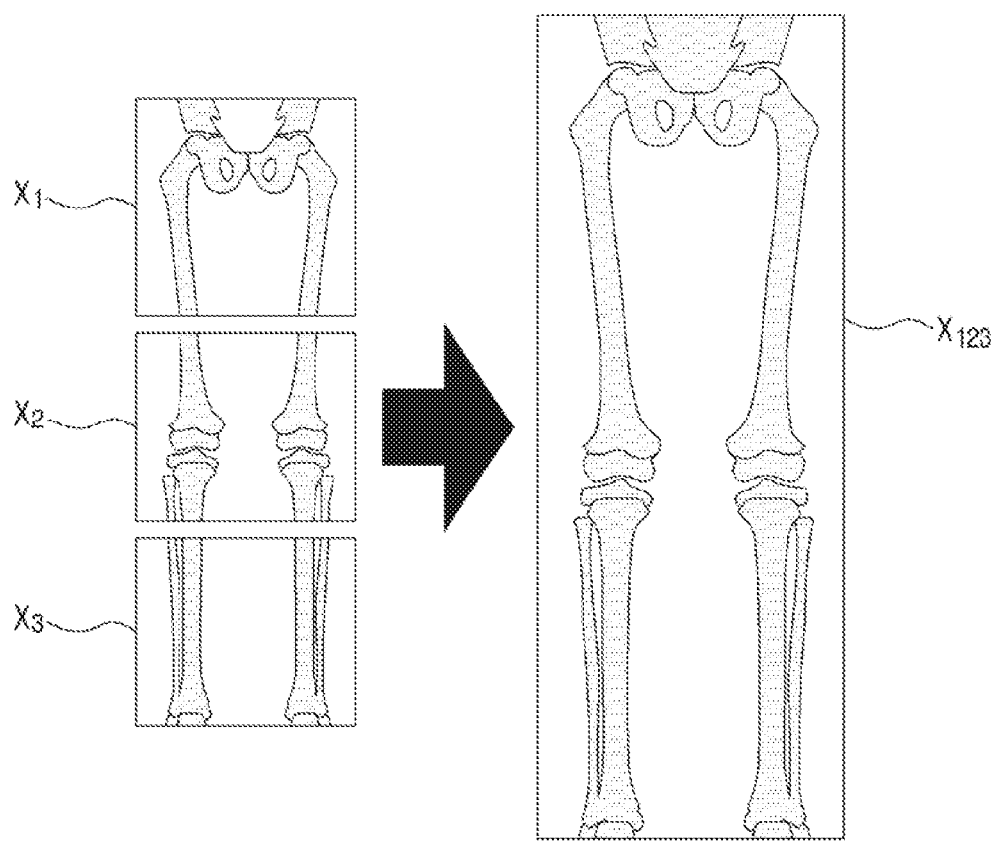
FIG. 12A is a view illustrating an example of a stitched-together image.
Figure 12B:
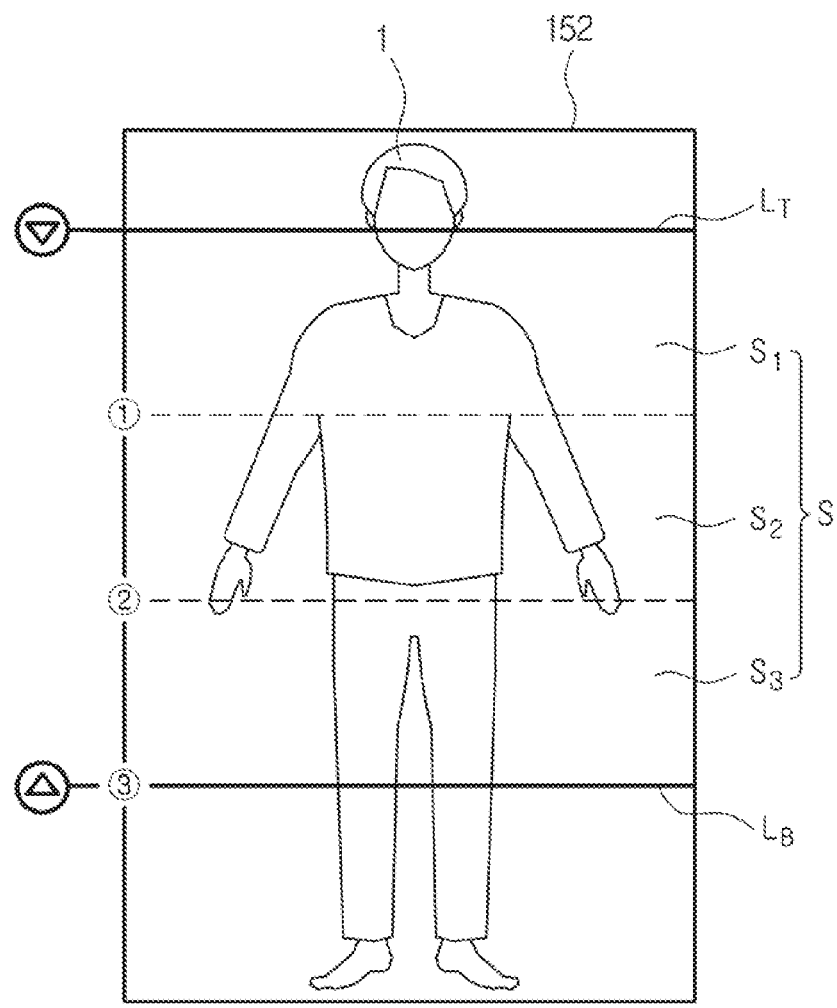
FIG. 12B is a view illustrating an example in which an imaging region is divided to perform stitching imaging.
Figure 12E:
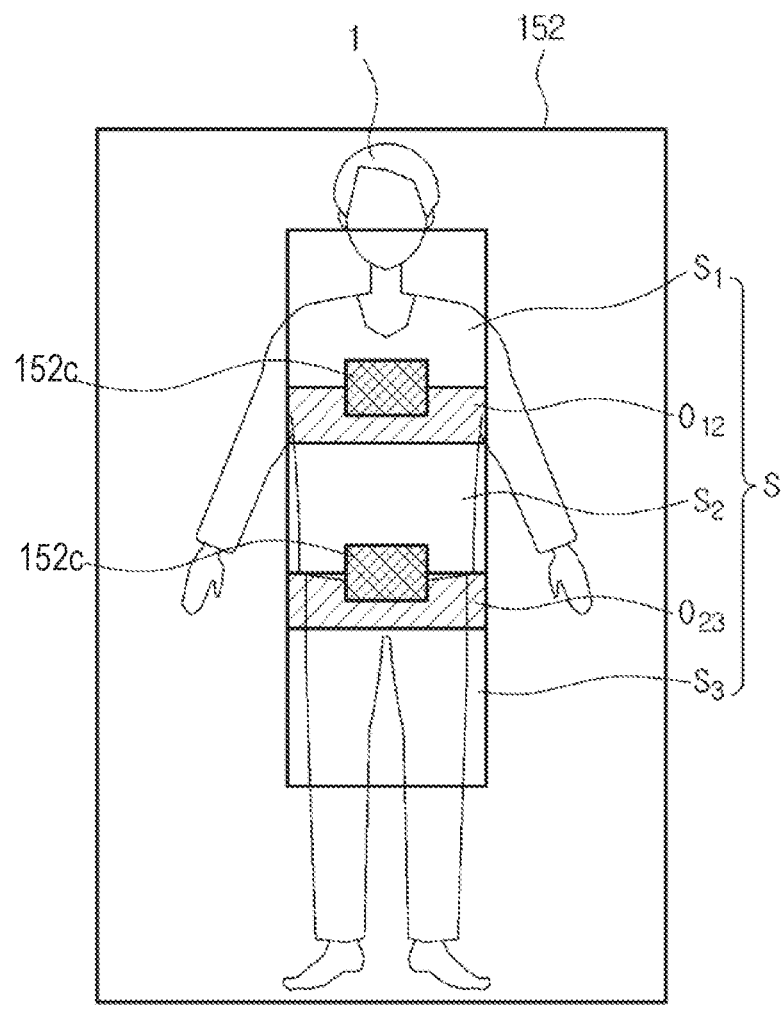

FIG. 12A is a view illustrating an example of a stitched-together image, FIG. 12B is a view illustrating an example in which an imaging region is divided to perform stitching imaging, and FIG. 12C is a view illustrating overlapping regions between each of a plurality of divided regions. FIGS. 12D and 12E are views illustrating an operation in which overlapping regions are automatically adjusted.

As illustrated in FIG. 12A, the X-ray imaging apparatus 100 may divide an X-ray imaging portion into a plurality of regions and may separately perform X-ray imaging for each of the plurality of divided regions.

The controller 140 may stitch X-ray images of divided regions, i.e., divided X-ray images $X_1$, $X_2$, and $X_3$, together to generate one stitched-together image $X_{123}$ showing a whole X-ray imaging portion. In an exemplary embodiment, an entire region in which stitching imaging is to be performed will be referred to as a stitching region.

As described above, when the selected imaging protocol corresponds to the stitching imaging, the work list 155 may be switched to the camera image 152 illustrated in FIG. 12B. Also, an imaging region corresponding to the selected imaging protocol may be automatically designated as the stitching region. The controller 140 may automatically divide the stitching region. For example, the controller 140 may divide the stitching region into uniform sizes, i.e., equal sizes, based on the smaller among height of the detection region and a maximum height of the X-ray irradiation region.

In a detailed example, when a value obtained by dividing a height of a stitching region S, i.e., a distance between a top line $L_T$ showing a point where the stitching region begins and a bottom line $L_B$ showing a point where the stitching region ends, by a height of the region to be detected by the X-ray detector 200 is an integer, the solution may become the number of divided regions, i.e., the number of divided X-ray images, used in stitching imaging. On the other hand, when the value is not an integer, the number of divided regions is larger than the solution by one, and a height of each of the divided regions is smaller than the height of the region to be detected by the X-ray detector 200.

For example, as illustrated in FIG. 12B, when the stitching region S is divided into three divided regions $S_1$, $S_2$, and $S_3$, three divided X-ray images may be respectively corresponding to the divided regions may be captured, and then the three divided X-ray images may be stitched together to generate one stitched-together X-ray image.

Boundary portions between each of the divided X-ray images may be matched to stitch the divided X-ray images together, and X-rays may be radiated so that predetermined regions between the divided X-ray images overlap each other for the matching. When designations of the divided regions are completed, the controller 140 may control the collimator 113 to radiate X-rays to the divided regions such that X-rays is radiated to a range expanded from a divided region toward adjacent divided regions by a predetermined size.

As an example illustrated in FIG. 12C, X-rays may be radiated so that a first-to-second overlapping region $O_{12}$ is disposed between the first divided region $S_1$ and the second divided region $S_2$, and a second-to-third overlapping region $O_{23}$ is disposed between the second divided region $S_2$ and the third divided region $S_3$.

Since the overlapping regions $O_{12}$ and $O_{23}$ are redundantly irradiated with X-rays, when a radiosensitive portion such as a genital organ or the heart is disposed in the overlapping regions, the controller 140 may move the overlapping regions to other portions to avoid redundantly irradiating the radiosensitive portion with X-rays or may output a warning to the user.

Whether a radiosensitive portion is disposed in the overlapping regions may also be determined by applying image processing such as an object recognition algorithm to the camera image 152. For example, a portion disposed at a central portion of a length from head to toe and from which thighs originate may be determined as a portion at which a genital organ is disposed, and a portion spaced apart 20 cm or less downward from armpit portions or shoulders may be determined as a portion at which the heart is disposed.

Information related to a radiosensitive portion, e.g., information on a position or form thereof, may be pre-stored in the storage unit 170 or may also be added or modified by the user.

When outputting a warning, the warning may be visually output through the display 150 or audibly output through a speaker provided in the X-ray imaging apparatus 100. When the warning is visually output, the overlapping regions may be directly displayed on the display 150 as illustrated in FIG. 12C, or text informing that the overlapping regions are disposed at a radiosensitive portion may be displayed on the display 150. Since the information simply needs to be conveyed, a method of outputting a warning is not limited.

The overlapping regions may be distorted in the stitched image and image quality of the overlapping regions in the stitched image may be degraded. Thus, the user may determine whether the overlapping portions are important portions in an X-ray image that need to be protected from degradation of image quality based on the provided information related to the overlapping regions.

With reference to FIG. 12C described above, a case in which the first-to-second overlapping region $O_{12}$ is disposed at a heart portion and the second-to-third overlapping region $O_{23}$ is disposed at a genital region portion is assumed.

As illustrated in FIG. 12D, the controller 140 may move a lower boundary of the first divided region $S_1$ downward so that the first-to-second overlapping region $O_{12}$ is disposed below the heart portion (①→①') and may move a lower boundary of the second divided region $S_2$ downward so that the second-to-third overlapping region $O_{23}$ is disposed below the genital organ portion (②→②').

Since a start point and an end point of the stitching region S are unchanged, the stitching region S does not change. Consequently, when a size of the first divided region $S_1$ exceeds a size of the region to be detected by the X-ray detector 200 or the maximum height of X-ray irradiation region due to the movement of the lower boundary of the first divided region $S_1$, or when a size of the second divided region $S_2$ exceeds the size of the region to be detected by the X-ray detector 200 or the maximum X-ray irradiation region due to the movement of the lower boundary of the second divided region $S_2$, the first divided region $S_1$ or the second divided region $S_2$ may be further divided or the entire stitching region S may be further divided into smaller regions, and then overlapping regions may be re-controlled.

Alternatively, when a fact that overlapping regions are disposed at radiosensitive portions is output visually or audibly as described above, the overlapping region may also be adjusted by the user. In this case, radiosensitive portions 152c may be displayed on the camera image 152 as illustrated in FIG. 12E to guide the user to reset the overlapping regions by avoiding the radiosensitive portions. For example, the user may move the overlapping regions displayed on the display 150 or move boundary lines of a plurality of divided regions to reset the overlapping regions.

Figure 13:
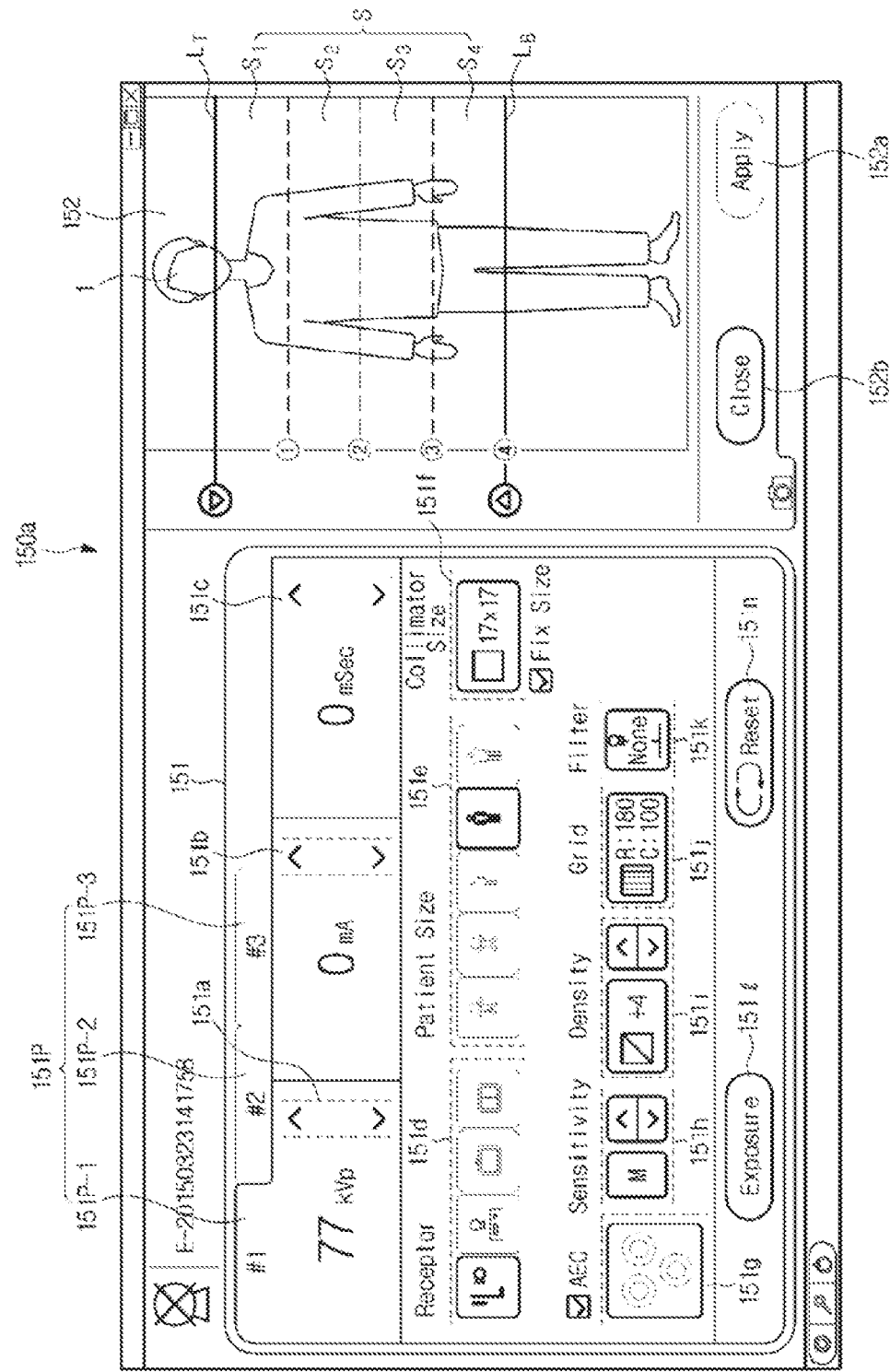
FIGS. 13 and 14 are views illustrating an example of a screen displayed for receiving a designation related to a region in which stitching imaging will be performed according to an exemplary embodiment.
Figure 14:
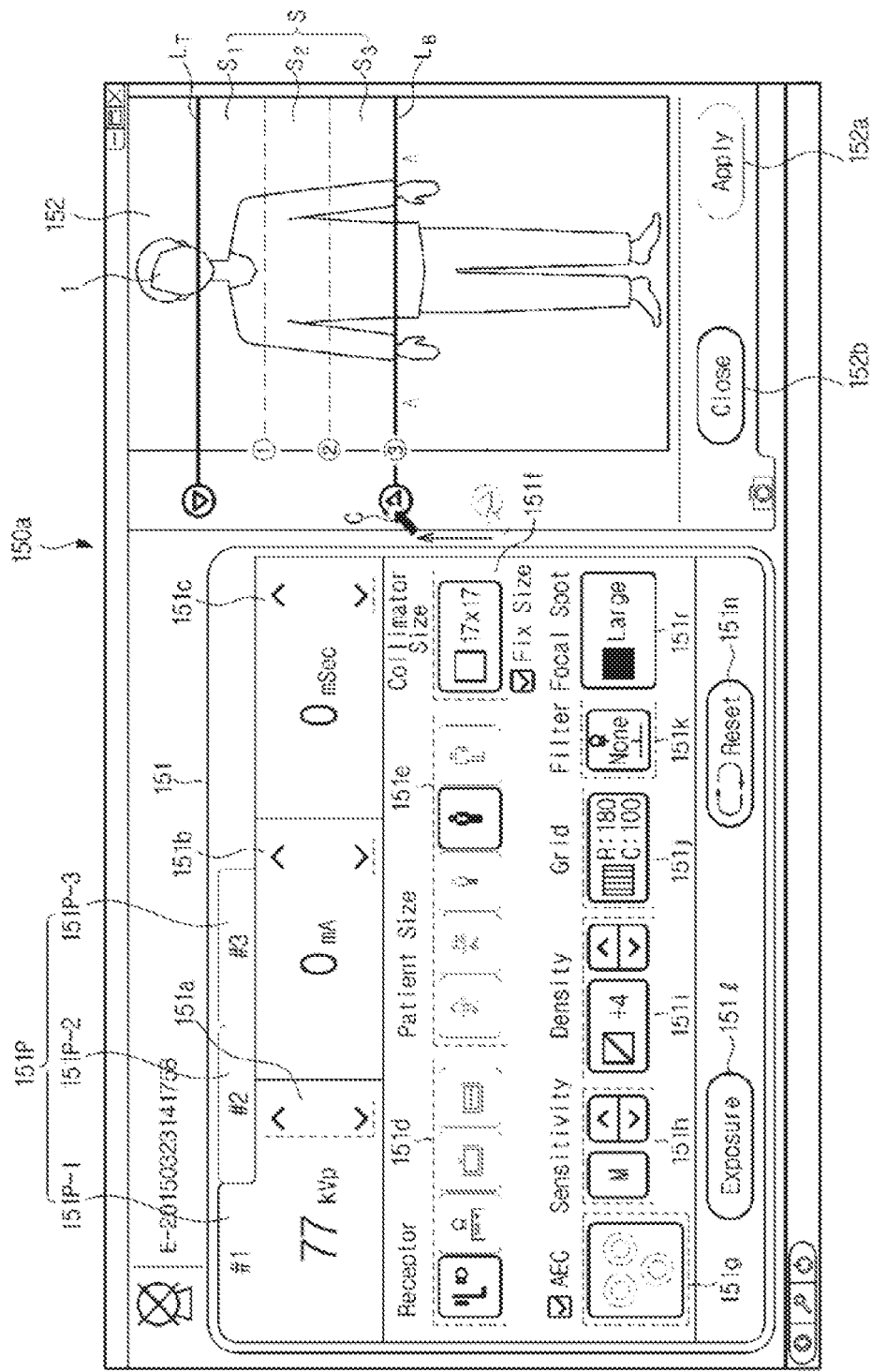
Figure 15:
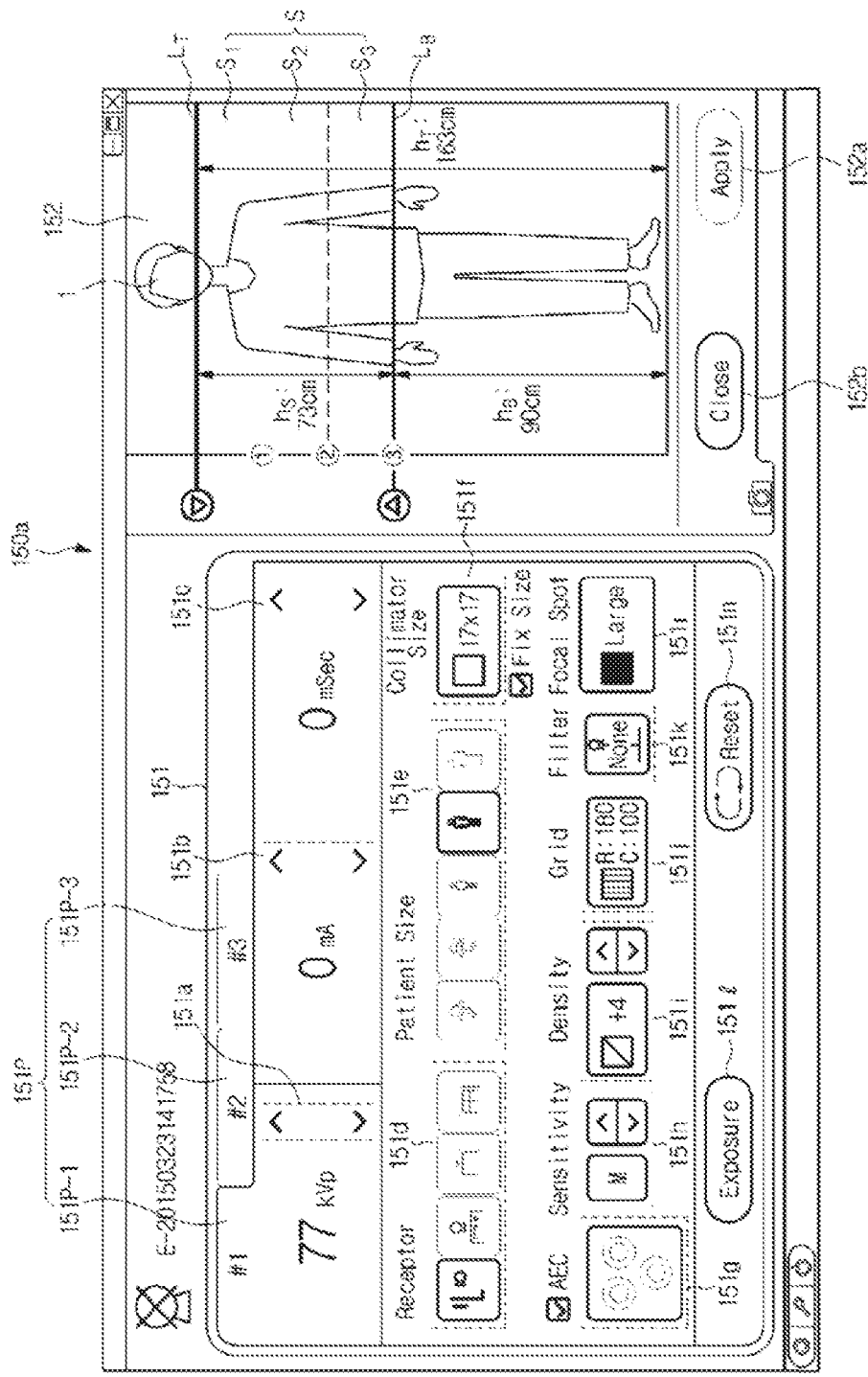
FIG. 15 is a view illustrating an example of a screen providing information on a height of a stitching region according to an exemplary embodiment.

FIGS. 13 and 14 are views illustrating an example of a screen displayed by the display of the X-ray imaging apparatus according to an exemplary embodiment, for receiving a designation related to a region in which stitching imaging will be performed, and FIG. 15 is a view illustrating an example of a screen providing information on the length of a stitching region.

According to an exemplary embodiment, the X-ray imaging apparatus 100 may automatically perform stitching imaging in a designated region when the user designates the stitching region through the input unit 160. Hereinafter, this will be described in detail.

To perform X-ray imaging, the imaging device 120 captures a camera image while the object is disposed in front of the X-ray detector. The captured camera image 152 may be displayed on the display 150 as illustrated in FIGS. 13 and 14. For example, the camera image 152 may be displayed in real time.

First, a process of designating a stitching region will be described.

The display 150 may display the top line $L_T$ designating a point where the stitching region begins and the bottom line $L_B$ designating a point where the stitching region ends on the camera image 152. As described above, the top line $L_T$ and the bottom line $L_B$ may be initially displayed at any position on the camera image 152 or may be displayed at positions corresponding to a selected imaging protocol.

Alternatively, only one of the top line $L_T$ and the bottom line $L_B$ may be displayed and the other one may be determined by designation of the number of divided imaging.

By viewing the camera image 152, the user may intuitively recognize the number of divided imaging operations necessary for acquiring a stitched image of the imaging region. In this aspect, the display 150 is configured to allow the user to intuitively and conveniently recognize the optimal number of divided imaging operations, thereby preventing excessive X-ray irradiation.

The user may manipulate the input unit 160 to adjust positions of the top line $L_T$ and the bottom line $L_B$. To guide the manipulation by the user, the display 150 may display the cursor C, and the cursor C may move on the screen displayed on the display 150 according to the manipulation of the input unit 160 by the user.

In a case in which the input unit 160 is a mouse, a trackball, or a keyboard, when the user manipulates the mouse, the trackball, or the keyboard, the cursor C moves according to a direction and a movement amount corresponding to the manipulation. In a case in which the input unit 160 is a touch pad, the cursor C moves according to a direction in which the user's finger moves and a movement amount of the user's finger.

For example, the user may drag the top line $L_T$ or the bottom line $L_B$ to move the top line $L_T$ or the bottom line $L_B$ to a desired position as illustrated in FIGS. 13 and 14. The top line $L_T$ and the bottom line $L_B$ may move in the vertical direction or in a longitudinal direction of the object. The stitching region S may be defined by the top line $L_T$ and the bottom line $L_B$. That is, a region between the top line $L_T$ and the bottom line $L_B$ may be the stitching region S.

When the stitching region S is designated, the controller 140 may automatically divide the stitching region S. The controller 140 may perform uniform division based on a region to be detected by the X-ray detector 200 and the stitching region S defined by the top line $L_T$ and the bottom line $L_B$.

The controller 140 may perform real-time uniform division every time the top line $L_T$ and the bottom line $L_B$ move, and show the result. For example, when the stitching region S is divided into four regions $S_1$, $S_2$, $S_3$, and S4 as illustrated in FIG. 13, the regions may be divided using guide lines such as a dotted line, and the lines dividing the regions may be numbered from 1 to 4 to provide information on the total number of divided regions and a number assigned to a corresponding divided region.

As shown in FIG. 12E, the first guideline ① may be a bottom limit for a maximum region for which an X-ray image is to be acquired by performing a single X-ray imaging. The second guideline ② may be a bottom limit for a maximum region for which an X-ray image is to be acquired by performing an X-ray imaging twice. The third guideline ③ may be a bottom limit for a maximum region for which an X-ray image is to be acquired by performing an X-ray imaging three times. The fourth guideline ④ may be a bottom limit for a maximum region for which an X-ray image is to be acquired by performing an X-ray imaging four times.

For example, when the user has dragged the bottom line $L_B$ toward the top line $L_T$ as illustrated in FIG. 14, the controller 140 may re-execute the real-time uniform division. When the stitching region S is reduced and divided into three regions $S_1$, $S_2$, and $S_3$, the guide lines dividing the regions may be numbered from 1 to 3 to inform that the stitching region is divided into a total of three regions.

Also, to emphasize that the number of divided imaging has changed, the display 150 may display the fourth guideline ④, so as to be distinguished from the remaining first through third guidelines ① through ③. For example, the fourth guideline ③ may be displayed as a dotted line, may be blurred or displayed in a different color. However, exemplary embodiments are not limited thereto, and the fourth guideline 12-4 may be displayed in different ways to be distinguished from the remaining first through third guidelines ① through ③.

When the designation of the stitching region is completed, the user may select apply button 152a and when the apply button 152a is selected, the display 150 may display divided window W1, W2, W3 on the camera image 152 described below.

For example, when the control command, which indicates the moving the top line $L_T$ or the bottom line $L_B$, is input again while the divided window is displayed, the present screen including the divided window may be switched to the previous screen including guide lines so that the stitching region or the divided regions are re-designated.

Meanwhile, as mentioned above, the controller 140 may perform uniform division based on the height $h_s$ of the stitching region S. Here, information related to the height $h_s$ of the stitching region S may be displayed on the display 150 to be provided to the user. For example, as illustrated in FIG. 15, the height $h_s$ of the stitching region S may be displayed as a number on the camera image 152. Here, a height $h_T$ of the top line $L_T$ from ground and a height $h_B$ of the bottom line $L_B$ from ground may also be displayed together with the height of the stitching region.

The controller 140 may calculate the heights $h_s$, $h_T$, and $h_B$ based on a distance between the imaging device 120 and the X-ray detector 200 or a distance between the imaging device 120 and the object 1.

For example, the controller 140 may pre-store relations between an imaging device coordinate system based on the imaging device 120, a global coordinate system of a space in which the X-ray imaging apparatus 100 is disposed, and a two-dimensional coordinate system of the camera image, and use conversions between the coordinate systems to calculate an actual height of the stitching region displayed on the camera image.

For example, the controller 140 may calculate the heights $h_S$, $h_T$, and $h_B$ changing according to a movement of the top line $L_T$ or the bottom line $L_B$ in real time and provide the calculated heights $h_S$, $h_T$, and $h_B$ to the user.

As described above, when information related to the size of the stitching region S is provided through the display 150, the user may intuitively recognize the size of the stitching region S and set the stitching region S or use the information as reference in setting an X-ray irradiation condition.

Although the controller 140 has been described in the exemplary embodiment above as dividing the stitching region S into equal sizes, an exemplary embodiment of the X-ray imaging apparatus 100 is not limited thereto. The sizes of the divided regions may also be adjusted to be different from each other, and the user may directly designate each of the divided regions. The user may designate the start point and end point of each divided region. If it is desired to split the whole stitching region S into three divided regions, a start point and an end point of a first divided region $S_1$, a start point and an end point of a second divided region $S_2$, and a start point and an end point of a third divided region $S_3$ may be designated.

If a designation of stitching imaging regions is performed by directly moving a large X-ray source, which may make it difficult for a user to precisely designate the stitching regions and may cause severe fatigue to the user.

According to the above embodiments, the X-ray imaging apparatus may precisely designate stitching regions and may reduce user fatigue.

For example, repetitive irradiation of an important body part with X-rays may be prevented by adjusting overlapping regions automatically or manually.

When setting the stitching region is completed, the user may select the "apply" button 152a to finish setting the stitching region and may set an X-ray irradiation condition for each of the divided regions.

For example, when the "apply" button 152a is selected, a plurality of divided windows W1, W2, and W3, e.g., GUIs, may be displayed, and each of the divided windows may be displayed by interoperating with the setting window 151 as will be described below.

In another example, each of the divided windows may interoperate with the setting window 151 and receive a setting of an X-ray irradiation condition before the "apply" button 152a is selected and even when the divided windows W1, W2, and W3 are not displayed.

FIGS. 16A to 19 are views illustrating a screen that allows a user to set an X-ray irradiation condition for each of a plurality of divided regions.

Although the same X-ray irradiation condition may be set for each of the plurality of divided regions, there are cases, including when features of an object shown in the divided regions are different from each other, when X-ray irradiation conditions need to be set differently.

Figure 16A:
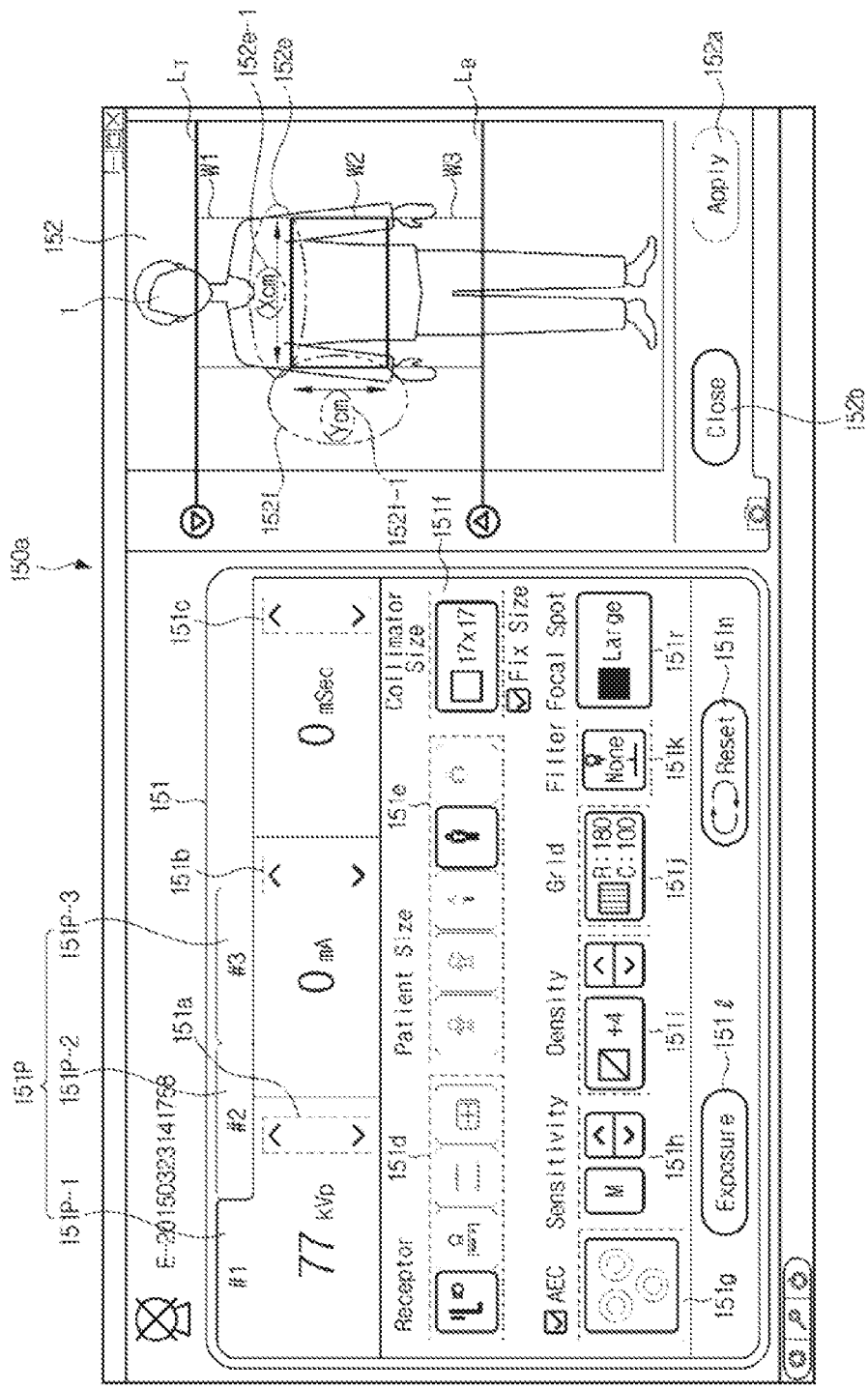
FIGS. 16A and 16B are views illustrating a screen that allows a user to set an X-ray irradiation condition according to an exemplary embodiment.

When designating the stitching region S is completed, the divided windows W1, W2, and W3 respectively corresponding to the divided regions may be displayed by being overlaid on the camera image 152 as illustrated in FIG. 16A. Each of the divided windows may include a plurality of boundary lines, and the plurality of boundary lines may have shapes corresponding to boundaries of the blades 113a, 113b, 113c, and 113d of the collimator 113. Consequently, the divided windows W1, W2, and W3 may have, for example, a square shape or a rectangular shape.

Figure 16B:
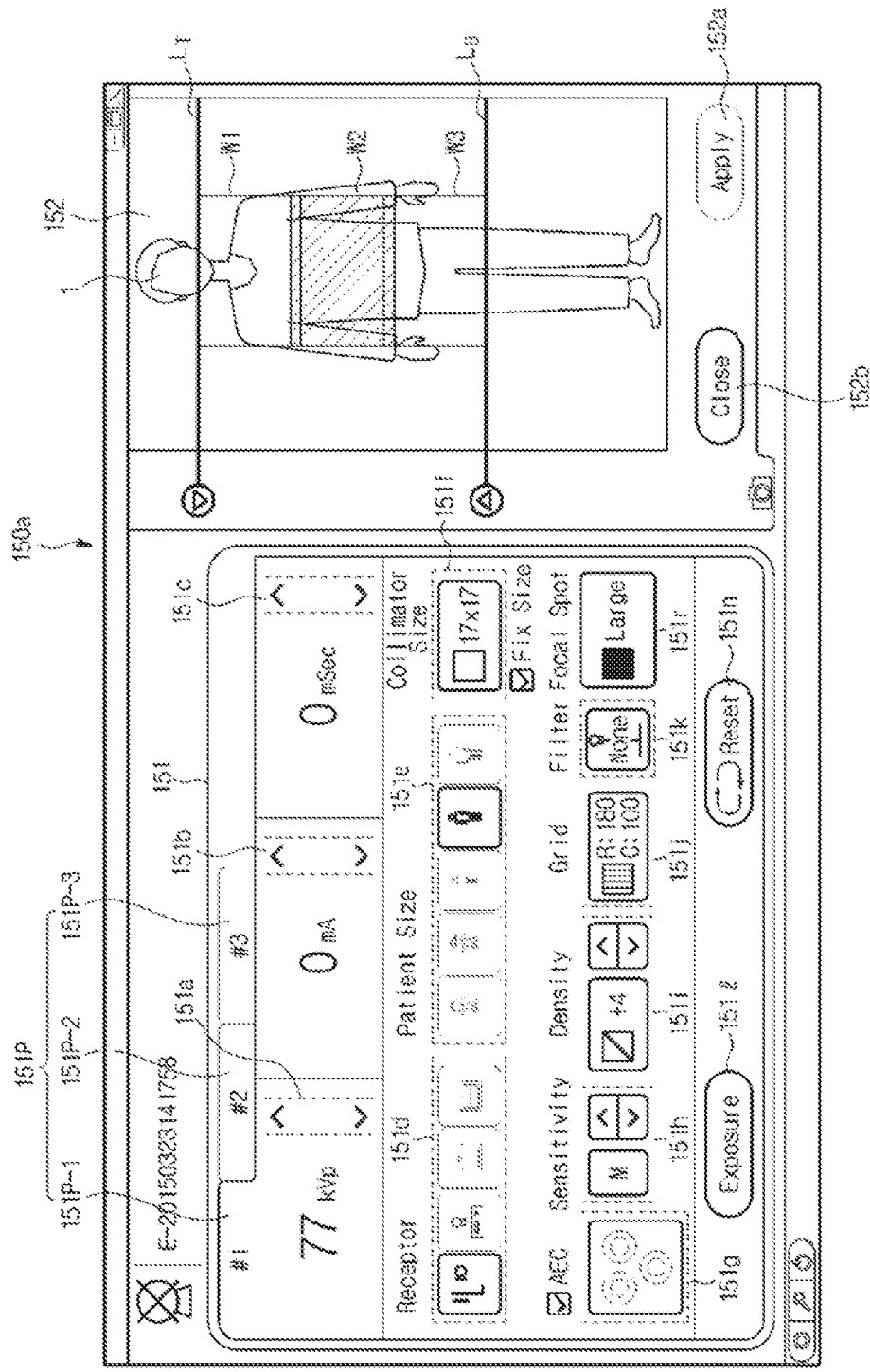

The first divided window W1 corresponds to the first divided region, the second divided window W2 corresponds to the second divided region, and the third divided window W3 corresponds to the third divided region Alternatively, as illustrated in FIG. 16B, the display 150 may display the divided windows W1, W2 and W3, adjacent ones of which partially overlap each other, over the camera image 152. The first and second divided windows W1 and W2 may overlap each other to represent overlapping region $O_{12}$ between the first divided region $S_1$ and the second divided region $S_2$, and the second and third divided windows W2 and W3 may overlap each other to represent overlapping region $O_{23}$ between the second divided region $S_2$ and the third divided region $S_3$.

The size of each of the divided windows corresponds to the size of each of the divided regions, and the width of each of the divided regions corresponds to width of the collimation region R or the X-ray irradiation region E. In this example, a case in which X-ray irradiation regions of the same width are applied to all of the divided regions will be described.

The height of each of the divided regions may be determined according to division of the region S by the controller 140 or the user, and the size of the collimation region may be automatically adjusted according to the height of each of the divided regions. Alternatively, as described above with reference to changing the irradiation window W, by clicking, touching, or clicking or touching then dragging at least one of upper boundary lines and lower boundary lines of the divided windows W1, W2, and W3, the user may change a position of a corresponding boundary line, and a divided region changes according to the changed position of the corresponding boundary line. The blades of the collimator 113 may move corresponding to the changed divided windows W1, W2, and W3.

Meanwhile, by changing a length of just one of the divided regions, heights of other divided regions which are not changed may increase or decrease when lengths of all of the divided regions are the same. When changes are made to only some of the plurality of divided regions by the user, the controller 140 may automatically change lengths of the remaining divided regions and control the collimator 113 according to the changed lengths.

As illustrated in FIG. 16A, information on the size of each of the divided windows W1, W2, and W3 may be displayed by being overlaid on the camera image 152. For this, the size displaying graphical objects 152e and 152f described above may be used, and the description of the irradiation window W may be identically applied to that of each of the divided windows W1, W2, and W3. However, a size of only the selected divided window W2 may be displayed as illustrated in FIG. 16, or sizes of all of the divided windows W1, W2, and W3 may also be displayed regardless of the selection.

Meanwhile, a GUI, through which an X-ray irradiation condition for each of the divided regions may be set, may be displayed on the setting window 151. For this, an identification tab 151p used in selecting the divided regions may be displayed at an upper end of the setting window 151, and the identification tab 151p may be provided for each of the divided regions. Identification tags #1, #2, and #3 respectively corresponding to the divided windows W1, W2, and W3 may be displayed on identification tabs 151p-1, 151p-2, and 151p-3, respectively.

When the user manipulates the input unit 160 and selects one of the identification tabs 151p-1, 151p-2, and 151p-3, a GUI through which an X-ray irradiation condition for a divided region corresponding to the selected identification tab may be set may be activated.

Figure 17:
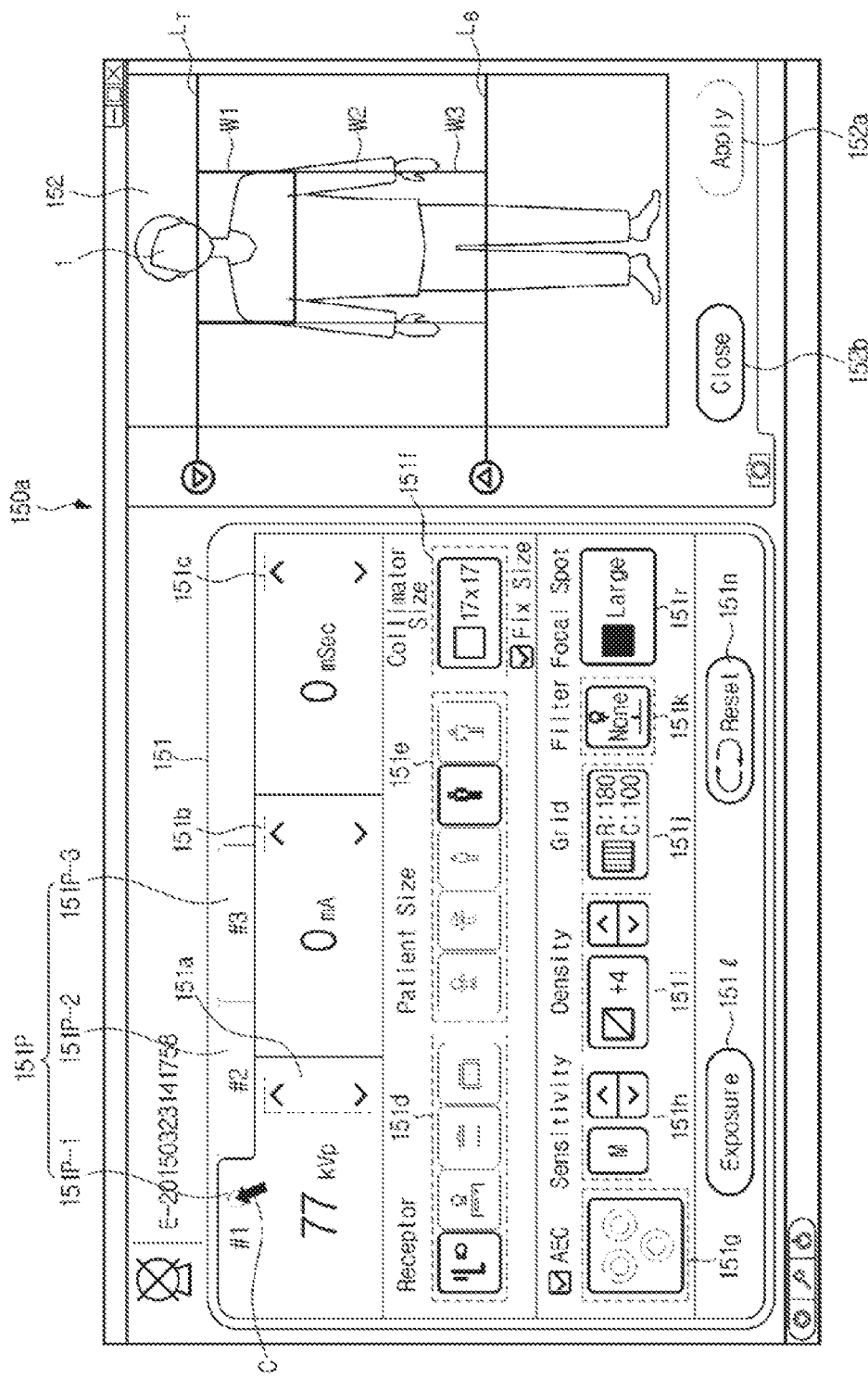
FIGS. 17, 18, and 19 are views illustrating a screen that allows a user to set an X-ray irradiation condition according to an exemplary embodiment.
Figure 18:
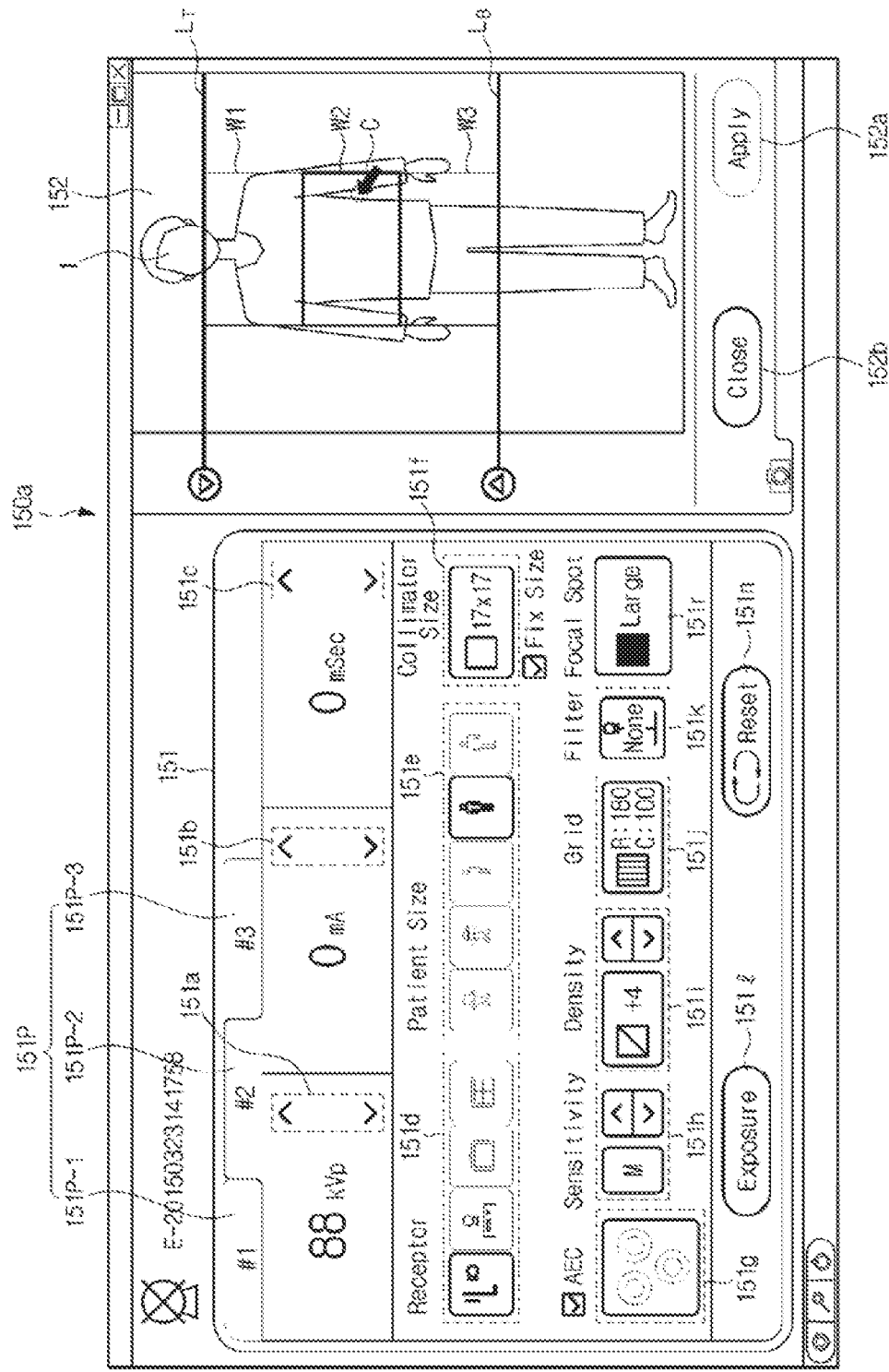

As in the example illustrated in FIG. 17, when the user moves the cursor C and selects the identification tab 151p-1 corresponding to the first divided region $S_1$, the camera image 152 may interoperate therewith, and the first divided window W1 displayed on the camera image 152 may be highlighted. That is, a selection of the divided region performed in the setting window 151 may also be reflected in the camera image 152. The purpose of the highlighting is to intuitively show the divided region currently selected by the user. For example, an edge of the first divided window W1 may be displayed in dark color. Alternatively, an edge of a selected divided window may also be highlighted by being displayed in different color or flickered, and a way of displaying a selected divided window is not limited.

Alternatively, the user may directly select a divided region whose X-ray irradiation condition will be set on the camera image 152. As in the example illustrated in FIG. 18, the user may move the cursor C and select the second divided window W2 displayed on the camera image 152. The setting window 151 may interoperate therewith, the identification tab 151p-2 corresponding to the second divided region S2 in the setting window 151 may be automatically selected, and a GUI through which an X-ray irradiation condition for the second divided region S2 may be set may be activated.

Figure 19:
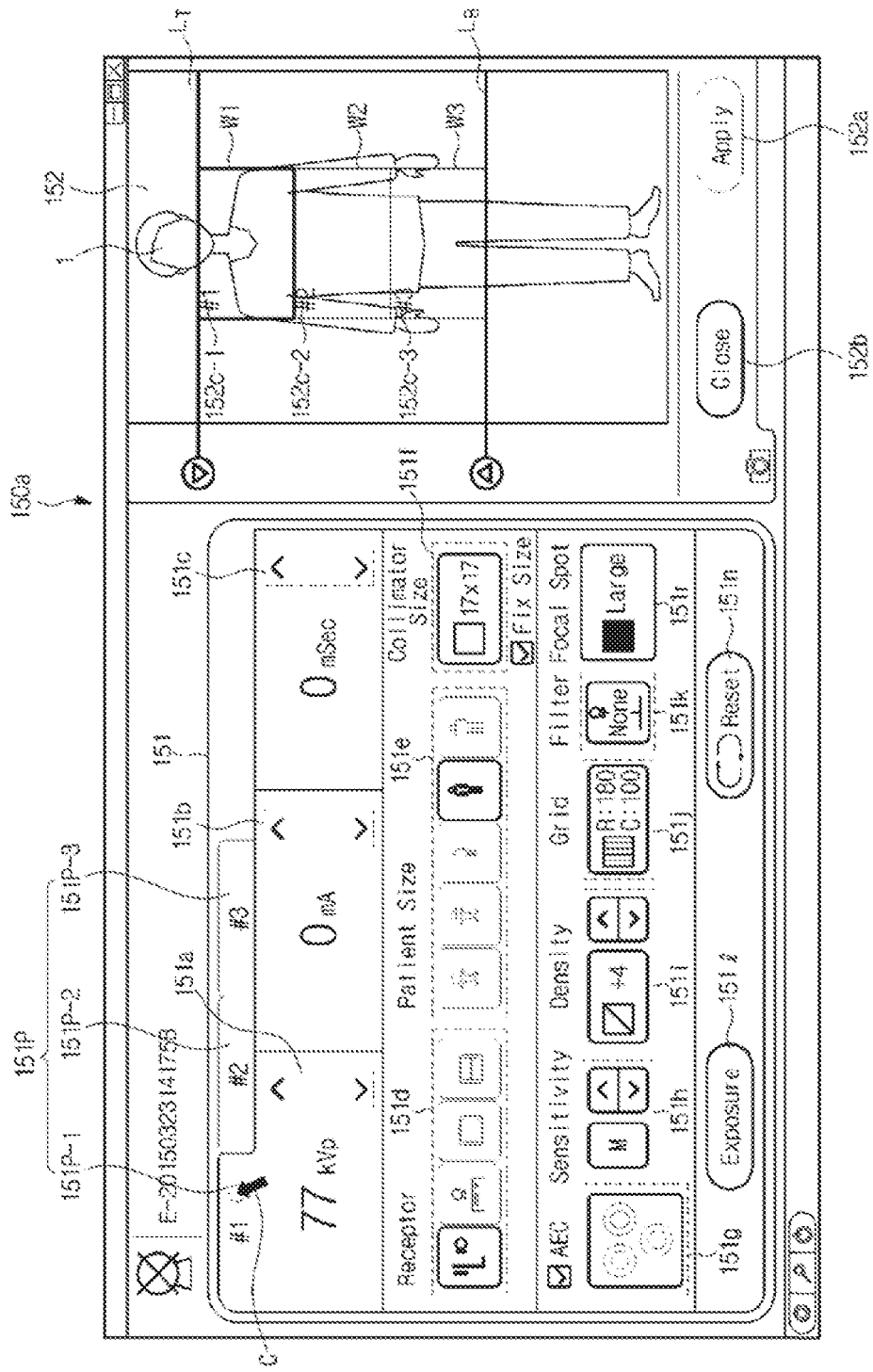

Meanwhile, as illustrated in FIG. 19, identification tags 152c-1, 152c-2, and 152c-3 respectively matching the identification tags #1, #2, and #3 displayed on the setting window 151 may be displayed also on the divided windows W1, W2, and W3 displayed on the camera image 152.

The user may look at the identification tags 152c-1, 152c-2, and 152c-3 respectively displayed on the divided windows W1, W2, and W3 and intuitively recognize a divided region whose X-ray irradiation condition may be set by the GUI activated in the setting window 151. Particularly, since upper and lower sides are not distinguished when X-ray imaging is performed on the table 10, it may be difficult to recognize matching relations between the divided windows W1, W2, and W3 displayed on the camera image 152 and the identification tags #1, #2, and #3 displayed on the setting window 151 in some cases. When the identification tags 152c-1, 152c-2, and 152c-3 respectively matching the identification tags #1, #2, and #3 displayed on the setting window 151 are displayed as in this example, the user may accurately set an X-ray irradiation condition without getting confused.

For example, when the first identification tag #1 is selected from the setting window 151 or the first divided window W1 is selected from the camera image 152 to set an X-ray irradiation condition for the first divided region $S_1$, the user may look at the first identification tag #1 displayed on the setting window 151 and the first identification tag 152c-1 displayed on the camera image 152 and easily check that the first divided region is a divided region currently targeted for setting an X-ray irradiation condition.

Although the case in which the identification tag displayed on the setting window 151 and the identification tag displayed on the camera image 152 are the same has been described in this example, an exemplary embodiment is not limited thereto. The identification tags different from each other may also be used so long as the user can recognize that the two identification tags match.

FIGS. 20 to 23 are views illustrating an example of a graphical user interface that allows making a selection of an X-ray irradiation condition to be directly performed on a camera image.

In the example described above, a case has been described as an example, in which inputs related to settings of tube voltage, tube current, X-ray exposure time, etc. are received by buttons displayed on the setting window 151.

Figure 20:
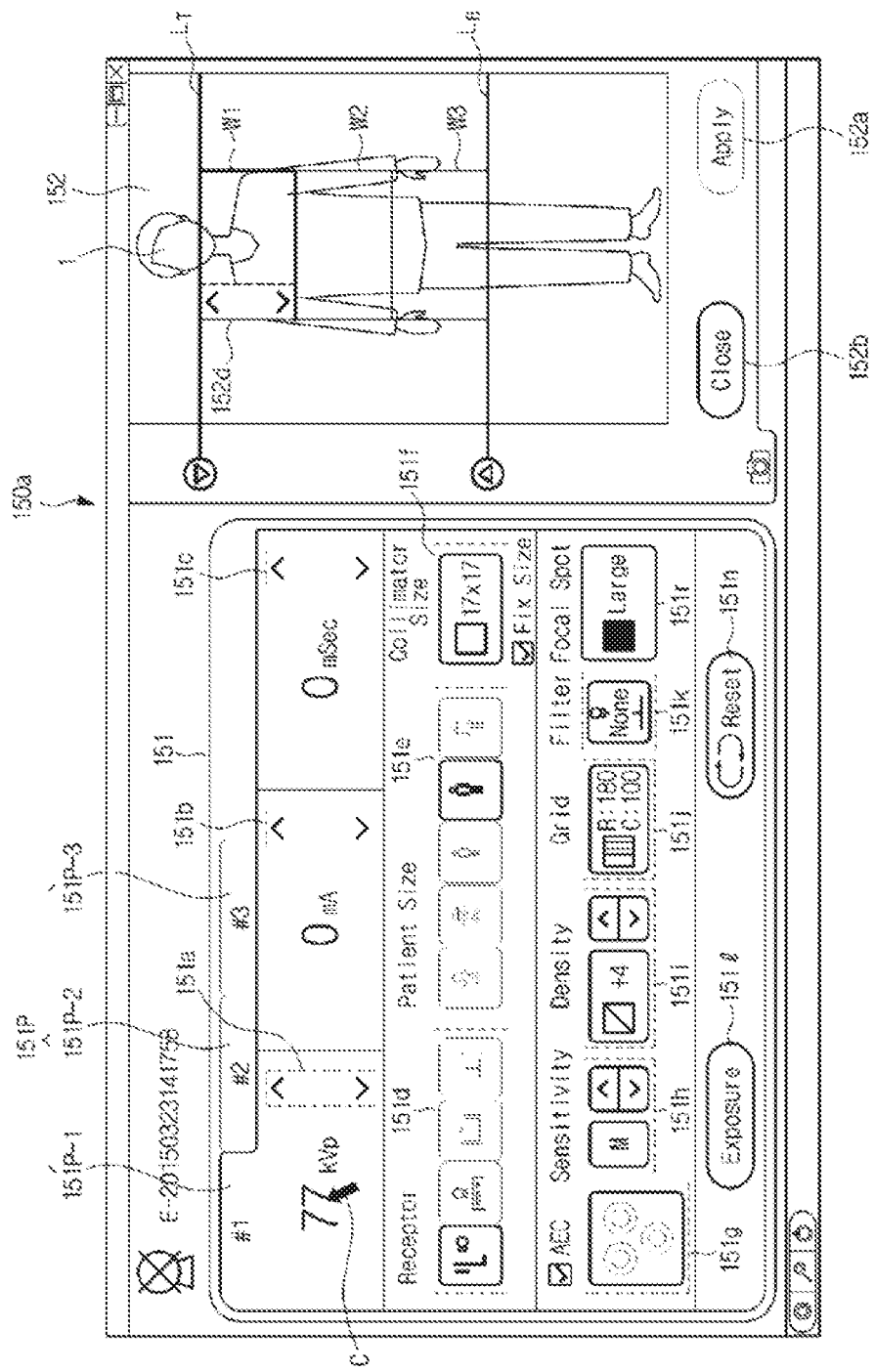
FIGS. 20, 21, 22, and 23 are views illustrating an example of a graphical user interface that allows making a selection of an X-ray irradiation condition according to an exemplary embodiment.

According to another example illustrated in FIG. 20, the display 150 may display a graphical object capable of receiving settings related to a tube voltage, a tube current, and an X-ray exposure time at a region adjacent to the divided window W1 on the camera image 152. In this example, a description will be given by assuming that the graphical object is a setting button.

One of the tube voltage, the tube current, and the X-ray exposure time may be selected as default, and an X-ray irradiation condition to be set may also be determined by the user selecting one of a region in which the tube voltage is displayed, a region in which the tube current is displayed, and a region in which the X-ray exposure time is displayed from the setting window 151. In the example shown in FIGS. 20 to 23, a case in which a tube voltage setting is received will be described.

Specifically, when a divided region targeted for setting a tube voltage is determined by selecting one of the plurality of tabs displayed on the setting window 151 or selecting one of a plurality of divided windows displayed on the camera image 152, the setting button 152d for receiving a setting related to the tube voltage of the corresponding divided region may be displayed at a region adjacent to the selected divided window W1. The setting button 152d may also be displayed within or outside the divided window W1.

Figure 21:
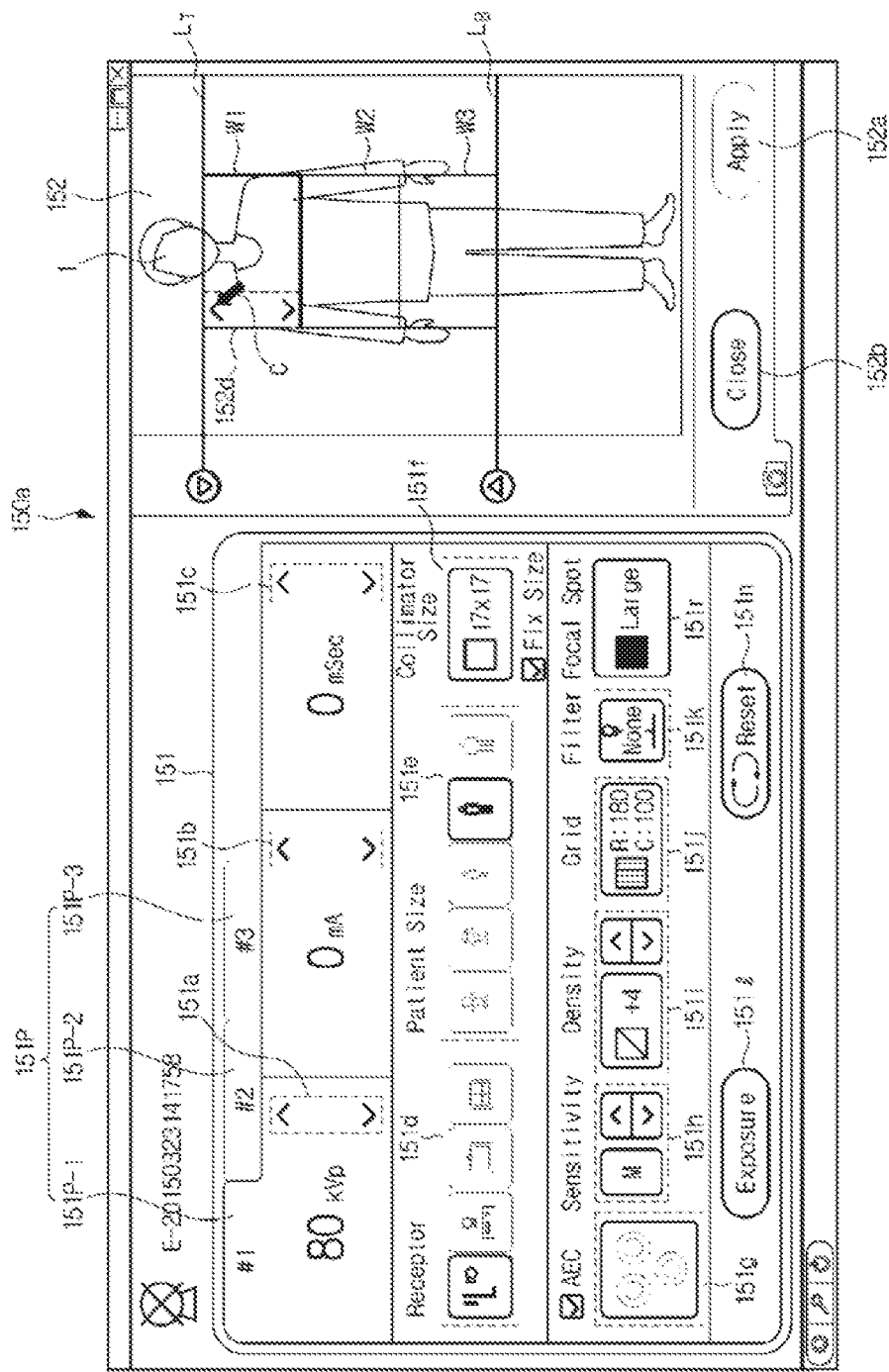

When the user manipulates the setting button 152d and inputs a command for increasing the tube voltage as illustrated in FIG. 21, the tube voltage may be set according to the input command, and a numerical value of the tube voltage displayed on the setting window 151 also increases corresponding to the input command.

Figure 22:
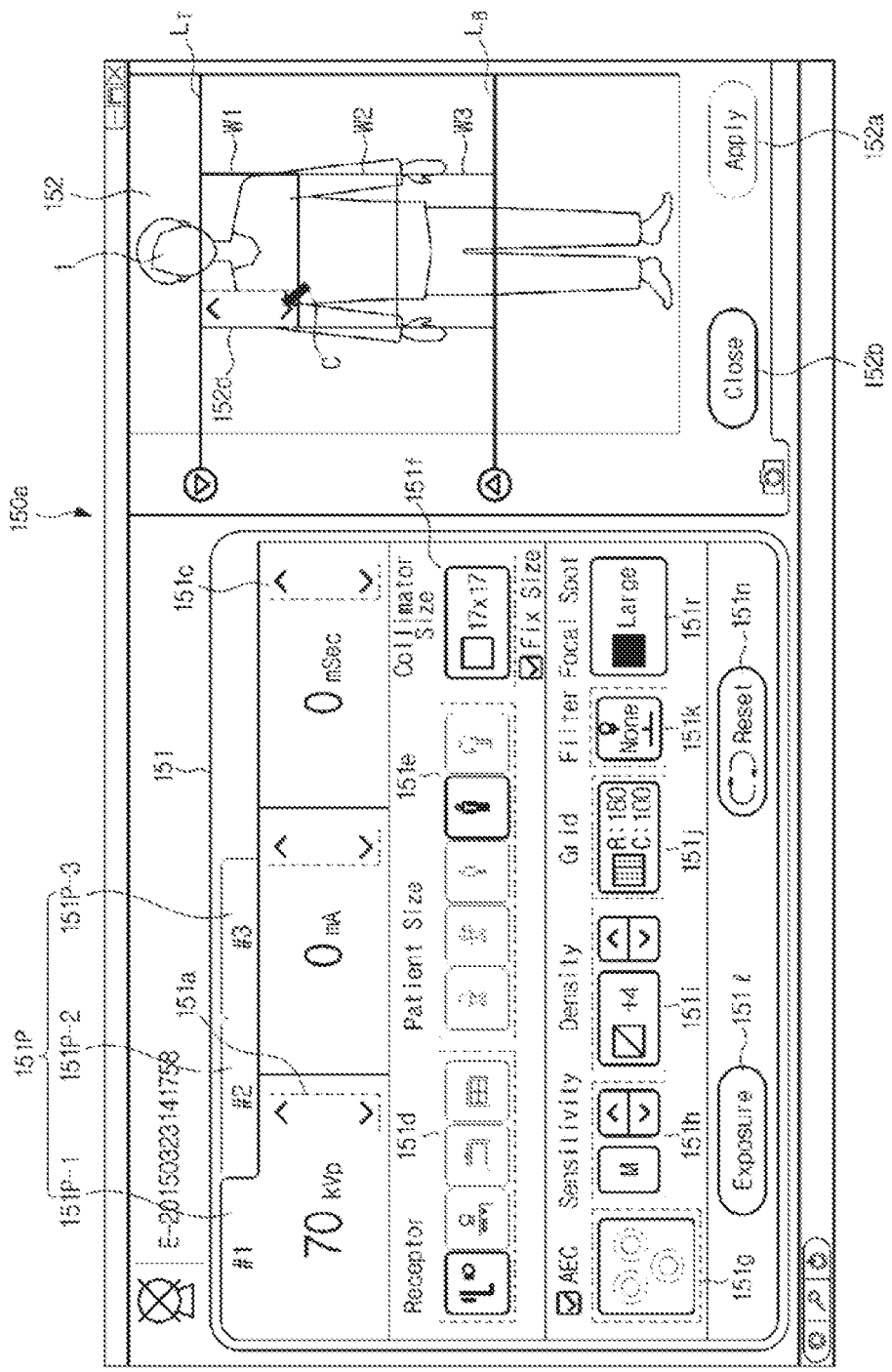

For example, as illustrated in FIG. 22, when the user manipulates the setting button 152d and inputs a command for decreasing the tube voltage as illustrated in FIG. 22, the tube voltage may be set according to the input command, and a numerical value of the tube voltage displayed on the setting window 151 also decreases corresponding to the input command. That is, manipulation of the setting button 152d and the screen displayed on the setting window 151 are synchronized with each other.

Figure 23:
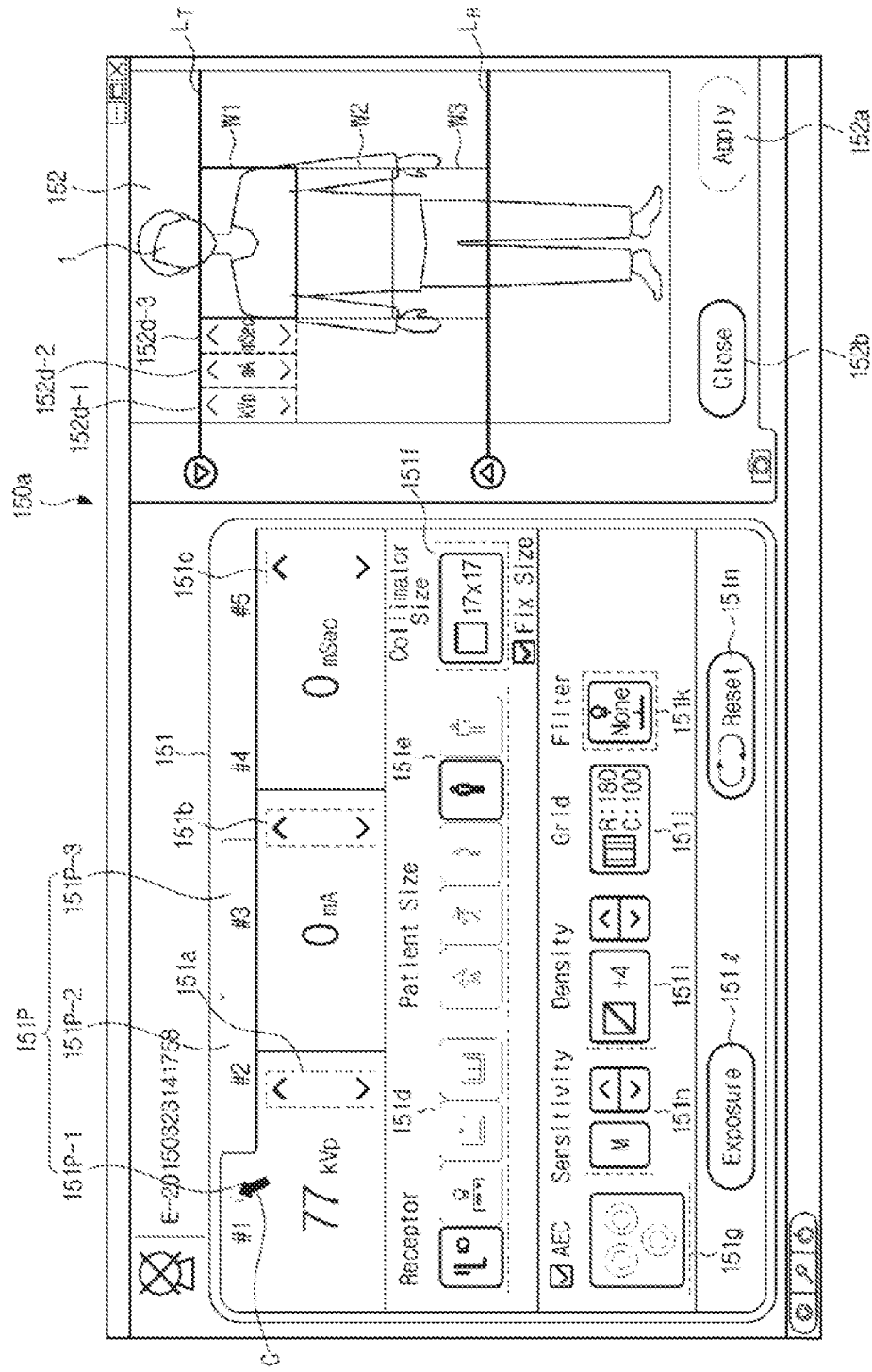

Meanwhile, as illustrated in FIG. 23, a tube voltage setting button 152d-1 for receiving a setting command related to a tube voltage, a tube current setting button 152d-2 for receiving a setting command related to a tube current, and an exposure time setting button 152d-3 for receiving a setting command related to an X-ray exposure time may also be separately displayed.

The user may manipulate each of the setting buttons 152d-1, 152d-2, and 152d-3 to input a setting command related to an X-ray irradiation condition that is desired to be set, and a numerical value displayed on the setting window 151 also changes according to the input command.

For example, when the user manipulates the tube voltage setting button 152d-1 and inputs a setting command related to a tube voltage, a numerical value of a tube voltage displayed on the setting window 151 is synchronized with the input command. When the user manipulates the tube current setting button 152d-2 and inputs a setting command related to a tube current, a numerical value of a tube current displayed on the setting window 151 is synchronized with the input command. When the user manipulates the exposure time setting button 152d-3 and inputs a setting command related to an X-ray exposure time, a numerical value of an X-ray exposure time displayed on the setting window 151 is synchronized with the input command.

In this way, the user may set an X-ray irradiation condition while checking a portion of an object to be imaged from an image and intuitively recognize an X-ray irradiation condition that is currently being set. For example, the user's workload may be reduced since moving the input unit 160 such as a mouse (when selecting by clicking) or moving the user's finger (when selecting by touch) decreases.

When setting an X-ray irradiation condition for all of the divided regions is completed, the user may select the "exposure" button 151*l* to perform X-ray imaging and may select the reset button 151*n* when attempting to initialize settings.

Figure 24:
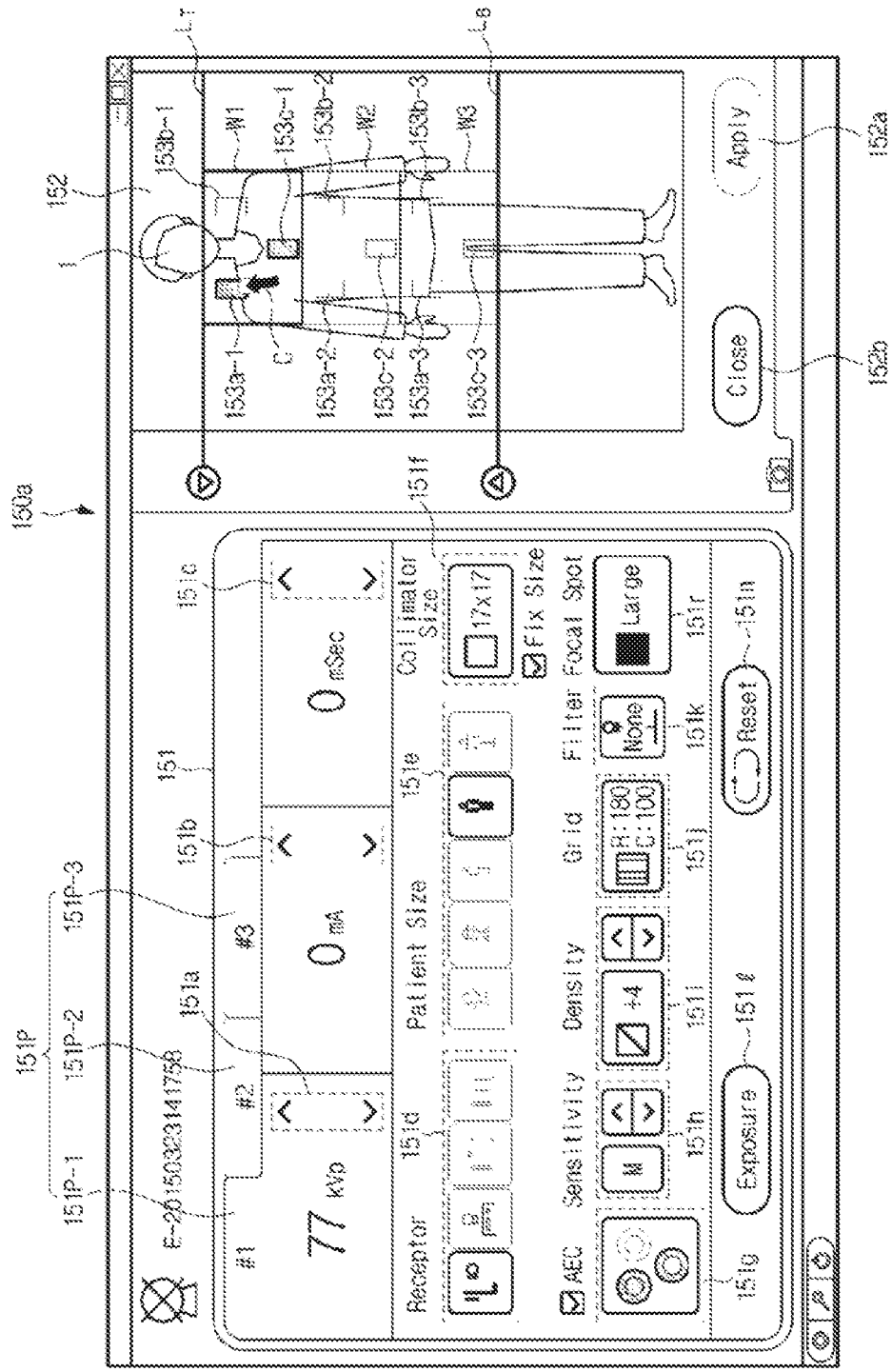
FIGS. 24 and 25 are views illustrating a screen that allows a user to select an AEC sensor in the X-ray imaging apparatus according to an exemplary embodiment.
Figure 25:
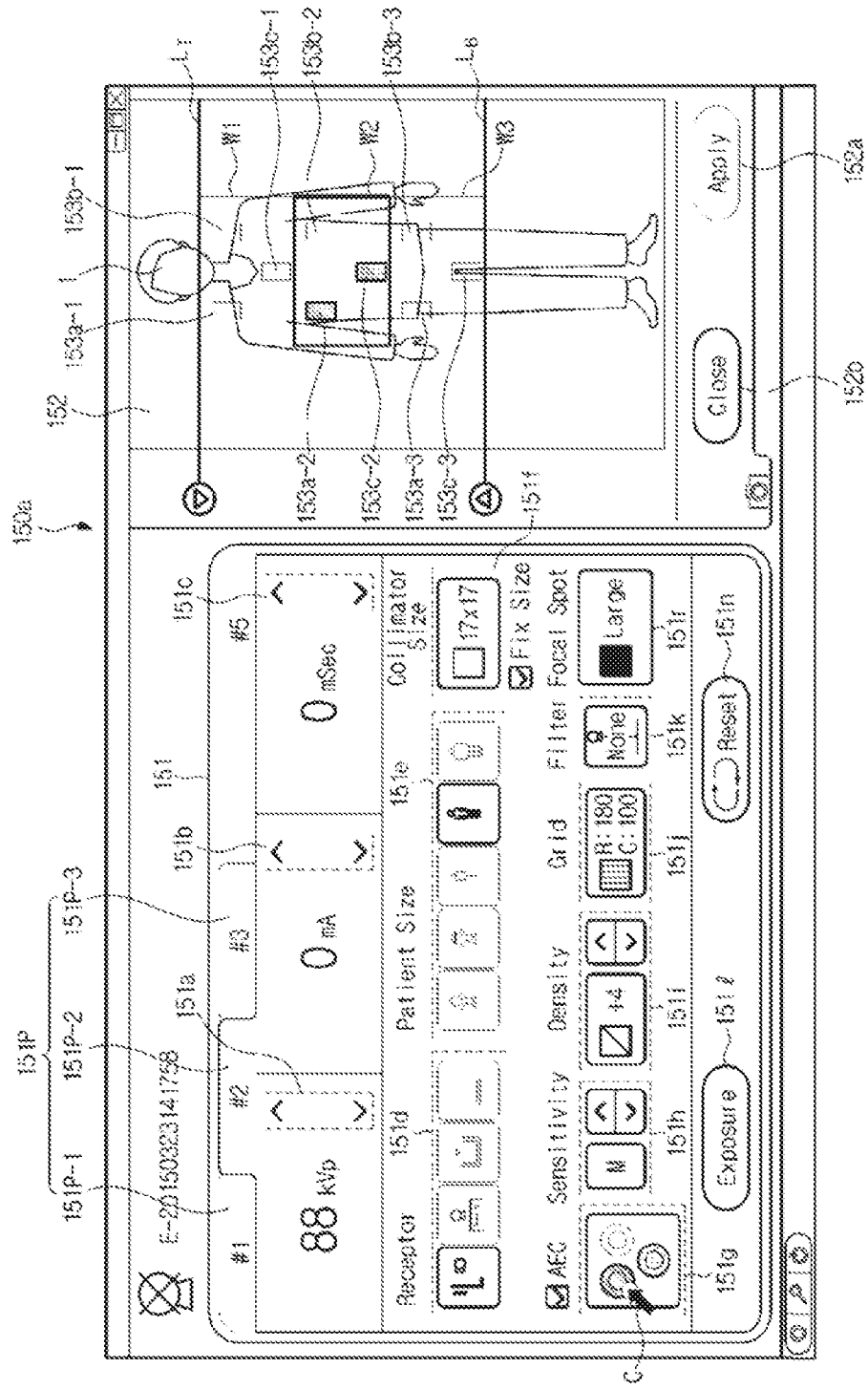

FIGS. 24 and 25 are views illustrating a screen that allows a user to select an AEC sensor in the X-ray imaging apparatus according to an exemplary embodiment.

As described above, the plurality of AEC sensors 26*a*, 26*b*, and 26*c* may be used for automatically controlling a dose of X-rays. All or some of the plurality of AEC sensors 26*a*, 26*b*, and 26*c* may be used according to a portion to be imaged by X-rays. Thus, a selection of an AEC sensor may also be performed for each of a plurality of divided regions.

A plurality of graphical objects respectively corresponding to the plurality of AEC sensors 26*a*, 26*b*, and 26*c* may be displayed within the divided windows W1, W2, and W3, and the plurality of graphical objects may be implemented as buttons for receiving a selection by the user.

The controller 140 may perform geometric registration of the camera image 152 by matching each point in the camera image 152 with a position in the actual space. For example, the controller 140 may use the relationships between camera coordinate system, global coordinate system and image coordinate system.

The controller 140 may acquire the positions of the AEC sensors 26*a*, 26*b*, and 26*c* that correspond to the position of the X-ray detector 200 and coordinate the AEC sensors 26*a*, 26*b*, and 26*c* with the camera image 152. The controller 140 may perform image processing whereby the AEC sensors 26*a*, 26*b*, and 26*c* are coordinated with the camera image 152 and the graphical objects that correspond to the AEC sensors are superimposed onto the camera image 152.

As illustrated in FIG. 24, a plurality of AEC sensor buttons 153*a*-1, 153*b*-1, and 153*c*-1, a plurality of AEC sensor buttons 153*a*-2, 153*b*-2, and 153*c*-2, and a plurality of AEC sensor buttons 153*a*-3, 153*b*-3, and 153*c*-3 respectively corresponding to the plurality of AEC sensors 26*a*, 26*b*, and 26*c* may be displayed. Each of the AEC sensor buttons may be displayed at a position corresponding to its AEC sensor.

The user may select an AEC sensor to be used for each of the plurality of divided regions. When a button corresponding to an AEC sensor to be used among the plurality of AEC sensor buttons 153*a*-1, 153*b*-1, and 153*c*-1 in the first divided window W1 is selected, the setting window 151 interoperates therewith, and the selection is reflected and displayed also on the AEC selection button 151*g* on the setting window 151.

Conversely, when a selection of an AEC sensor is input using the AEC selection button 151*g* on the setting window 151 as illustrated in FIG. 25, the camera image 152 interoperates therewith, and the selection is reflected and displayed also on the plurality of AEC sensor buttons 153*a*-2, 153*b*-2, and 153*c*-2.

When the selection of an AEC sensor is input, an AEC sensor button corresponding to the selected AEC sensor may be highlighted by a change in color thereof, darkening or lightening an edge thereof, flickering of the edge thereof, etc. to reflect that the corresponding AEC sensor has been selected. Alternatively, the selected AEC sensor and non-selected AEC sensor may be distinguished from each other by solid line and dotted line. Alternatively, on/off may be displayed as text on the AEC sensor buttons, and when an AEC sensor button with on is selected, the text may change from on to off. When an AEC sensor button with off is selected, the text may change from off to on.

For example, when a check box above the AEC selection button 151*g* is selected, the plurality of AEC sensors may be turned on or off.

The selected AEC sensor may be turned on when an X-ray imaging is performed, and the non-selected AEC sensor may be turned off when an X-ray imaging is performed. However, the reverse may be possible.

Alternatively, an AEC sensor may also be automatically selected by the controller 140 based on a size of each of the plurality of divided regions. For example, the controller 140 may exclude AEC sensors that are disposed outside the X-ray irradiation region from being selected.

For example, the controller 140 may detect a contour or edge of the object 1 in the camera image 152 via image processing such as contour detection or edge detection and turn off the AEC sensor outside the object 1.

If the AEC sensor outside the object 1 is not turned off, the AEC sensor may directly receive X-rays that have not passed through the object 1. This causes the amount of X-rays received by the AEC sensor to quickly exceed a predetermined amount. In this case, the quality of an X-ray image may be degraded due to the lack of X-ray dose irradiated on the object 1.

Thus, the controller 140 may prevent degradation in quality of an X-ray image by turning off an AEC sensor that is positioned outside the object 1.

Even when the controller 140 has selected an AEC sensor, the controller 140 may display which AEC sensor has been selected on the display 150. That is, the selection by the controller 140 may also be reflected in the plurality of AEC sensor buttons 153*a*-2, 153*b*-2, and 153*c*-2 and the AEC selection button 151*g* on the setting window 151.

As described above, when the AEC sensor button displayed on the camera image 152 and the AEC selection button 151*g* on the setting window 151 interoperate with each other, the user may more intuitively recognize a position of the AEC sensor selected by the user.

For example, since the X-ray detector 200 is blocked by the object 1 during X-ray imaging, the user is not able to directly recognize a position of the AEC sensors. According to the exemplary embodiment described above, the display 150 may display the AEC sensor buttons over the camera image 152, thereby enabling the user to intuitively and conveniently recognize a relationship between positions of an actual object and AEC sensors.

When setting an X-ray irradiation condition for each of the divided regions is completed and the exposure button 151*l* is selected, the X-ray imaging apparatus 100 may automatically control positions of the X-ray source 110 and the X-ray detector 200 and perform stitching imaging. Hereinafter, this will be described with reference to FIGS. 26A to 26C.

Figure 26A:
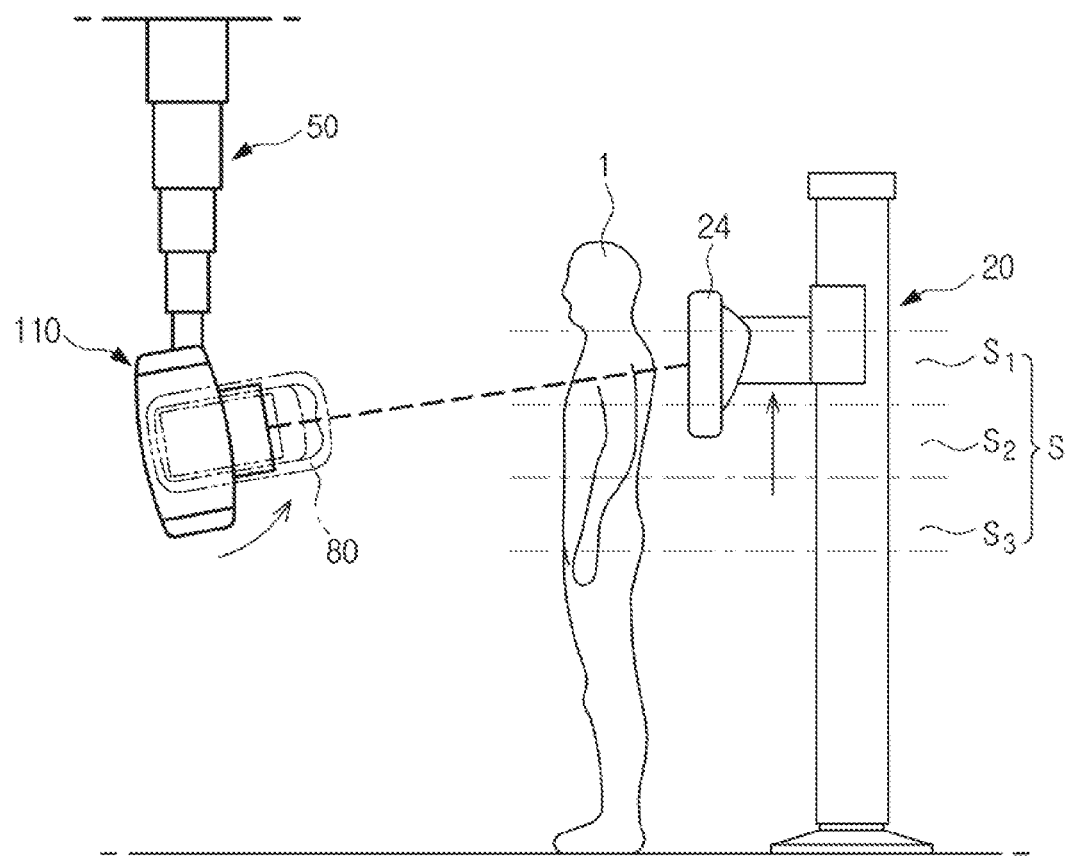
FIGS. 26A, 26B, and 26C are views related to stitching imaging according to an exemplary embodiment.
Figure 26B:
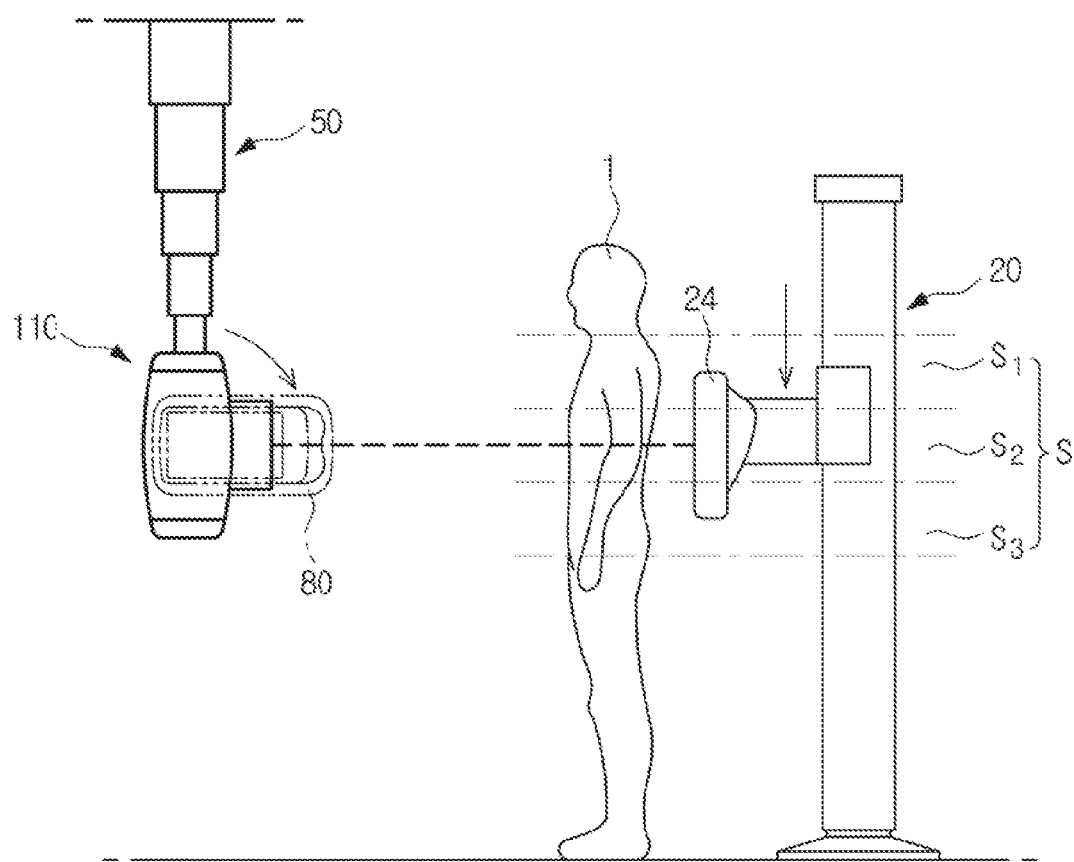
Figure 26C:
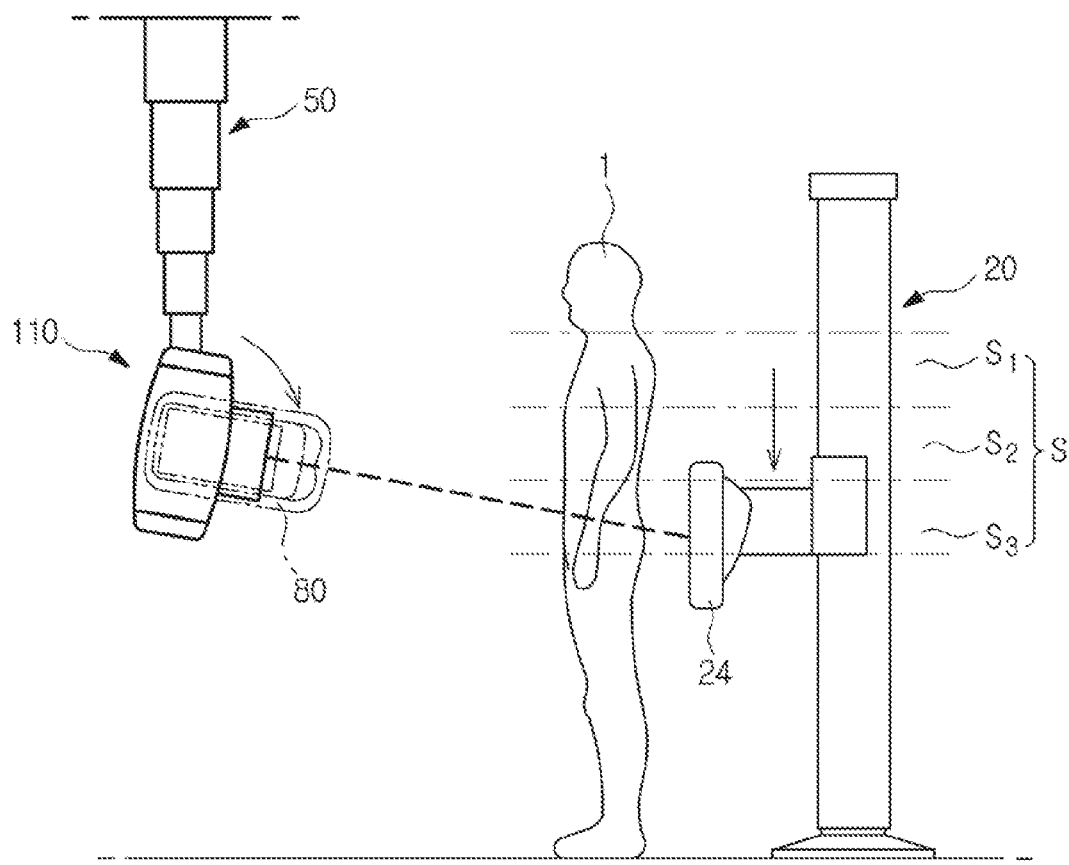

FIGS. 26A to 26C are views related to a case in which stitching imaging is performed by controlling a tilt angle of the X-ray source in the X-ray imaging apparatus according to an exemplary embodiment. In an exemplary embodiment, a case in which imaging is performed by mounting the X-ray detector 200 on the stand 20 is given as an example.

Before operating the X-ray imaging apparatus 100, calibration may be performed to calculate a location relationship between a camera image obtained through imaging device 120 and an X-ray image.

For example, when the stitching region S is divided into the three regions $S_1$, $S_2$, and $S_3$, the controller 140 calculates a first location or a first tilt angle at which the first divided region $S_1$ is irradiated with X-rays, a second location or a second tilt angle at which the second divided region $S_2$ is irradiated with X-rays, and a third location or a third tilt angle at which the third divided region $S_3$ is irradiated with X-rays, based on the previous calibration result.

Prior to performing stitching imaging, it may be assumed that the X-ray source 110 has been moved to a position corresponding to the X-ray detector 200. For example, when both the stand 20 and the table 10 are present in an examination room, and the user has selected the stand 20 using the capture position setting button 151d, the X-ray source 110 may be automatically moved to a position corresponding to the stand 20. The position of the X-ray source 110 corresponding to the stand 20 may be pre-stored.

Alternatively, the X-ray source 110 may also be manually moved by the user to the position corresponding to the stand 20.

For example, when the stitching region S is divided into three regions $S_1$, $S_2$, and $S_3$, the tilt angle of the X-ray source 110 may be adjusted to an angle corresponding to the first divided region $S_1$ as illustrated in FIG. 26A to capture a first divided X-ray image, the tilt angle of the X-ray source 110 may be adjusted to an angle corresponding to the second divided region $S_2$ as illustrated in FIG. 26B to capture a second divided X-ray image, and the tilt angle of the X-ray source 110 may be adjusted to an angle corresponding to the third divided region $S_3$ as illustrated in FIG. 26C to capture the third divided X-ray image. Here, the height of the X-ray source 110 from the ground may be fixed.

The controller 140 may transmit a control signal to a motor that adjusts the tilt angle of the X-ray source 110 to adjust the tilt angle of the X-ray source 110 to an angle corresponding to each of the divided regions.

For example, when X-ray irradiation conditions of the first divided region, the second divided region, and the third divided region are set to be different from each other, the X-ray source 110 or the X-ray detector 200 may be controlled to correspond to a set irradiation condition when each of the divided regions is being captured.

In another example, the height of the X-ray source 110 may also be adjusted to a height corresponding to the first divided region $S_1$ to capture the first divided X-ray image, adjusted to a height corresponding to the second divided region $S_2$ to capture the second divided X-ray image, and adjusted to a height corresponding to the third divided region $S_3$ to capture the third divided X-ray image. Here, the tilt angle of the X-ray source 110 may be fixed.

In yet another example, the height and the tilt angle of the X-ray source 110 may also be simultaneously adjusted.

In both of the examples, the X-ray detector 200 is moved to a position corresponding to each of the divided regions. To move the X-ray detector 200, the mounting unit 24 on which the X-ray detector 200 is mounted may be moved in the vertical direction. The controller 140 may transmit a control signal to a motor driving the mounting unit 24 to move the X-ray detector 200 mounted on the mounting unit 24 to a position corresponding to each of the divided regions.

When each of the divided regions is designated, the controller 140 may calculate an actual position of the X-ray detector 200 to match the center of the designated divided region and the center of the X-ray detector 200. Also, as described regarding FIGS. 11-15, aligning the X-ray source 110 and the X-ray detector 200 may be performed.

The controller 140 may generate the divided X-ray images $X_1$, $X_2$, and $X_3$ respectively corresponding to the divided regions $S_1$, $S_2$, and $S_3$ after processing electrical signals due to detection, by the X-ray detector 200, of X-rays that have passed through the object and may stitch the divided X-ray images $X_1$, $X_2$, and $X_3$ to generate one stitched-together image $X_{123}$.

The display 150 may display the generated stitched-together image or may also display the divided X-ray images.

For example, the controller 140 may combine electrical signals output from the X-ray detector 200 to generate an X-ray image or perform various types of image processing of the generated X-ray image. The controller 140 may use a high pass filter to add a sharpening effect to the whole image or a part of the image or may use a low pass filter to add a blurring effect to the whole image or a part of the image.

To perform the image processing described above, the controller 140 may include a graphics processing unit (GPU).

Hereinafter, a method for controlling an X-ray imaging apparatus according to an exemplary embodiment will be described.

The X-ray imaging apparatus 100 described above may be used in the method for controlling an X-ray imaging apparatus according to an exemplary embodiment. Consequently, the descriptions given above with reference to FIGS. 1 to 26C may also be identically applied to the method for controlling an X-ray imaging apparatus.

FIG. 27 is a flowchart related to a method for controlling an X-ray imaging apparatus according to an exemplary embodiment.

Referring to FIG. 27, the imaging device 120 is used to capture a camera image (operation 301). An object may be disposed in front of the X-ray detector 200 that will be used in X-ray imaging, and the X-ray detector 200 may be mounted on the stand 20 or the table 10 or may also be portably used. The camera image may be a video or a still image captured at predetermined intervals.

The display 150 displays graphical objects displaying various types of information together with the camera image (operation 302). The graphical objects may include size displaying graphical objects 152e and 152f showing a size of the collimation region, a length displaying graphical object 152g showing the length of the object, and a distance displaying graphical object 152h showing an SID or SOD.

The description related to a method for displaying each of the graphical objects is the same as in the exemplary embodiment of the X-ray imaging apparatus 100 described above.

The irradiation window W may be displayed by being overlaid on the camera image 152 to display the size displaying graphical objects 152e and 152f, and the size displaying graphical objects 152e and 152f may be displayed at an upper end portion and a side portion of the irradiation window W to show a width and height of the collimation region.

The user may adjust the size of the irradiation window W with reference to the displayed size displaying graphical objects 152e and 152f to adjust the size of the collimation region and may adjust the stitching region with reference to the length displaying graphical object 152g (operation 303). Alternatively, the user may adjust the distance between the X-ray source 110 and the X-ray detector 200 with reference to the distance displaying graphical object 152h, input or change various types of settings, input an exposure command to begin X-ray imaging, or input a cancel command for setting or an operation.

According to this example, setting by the user may be guided by the displaying the graphical objects showing the size of the collimation region, the length of the object, and information on the SOD or the SID. For example, when a captured X-ray image does not include the whole portion desired to be imaged and thus imaging needs to be performed again, the size displaying graphical objects 152e and 152f or the length displaying graphical object 152h may be displayed to guide the user on how much the size of the collimation region or the stitching region has to be increased.

When all required settings are determined and an X-ray exposure command is input, the adjusted collimation region or stitching region is irradiated with X-rays (operation 304).

The X-ray detector 200 receives X-rays that have passed through the object 1 and stores and outputs electrical signals corresponding to the received X-rays. The controller 140 may acquire an X-ray image based on the output electrical signal (operation 305), and the acquired X-ray image may be provided to the user through the display 150 provided at the work station 180 or the sub-display device 80.

FIG. 28 is a flowchart related to an example of performing divided imaging in the method for controlling an X-ray imaging apparatus according to an exemplary embodiment.

Referring to FIG. 28, the imaging device 120 is used to capture a camera image (operation 310). The object may be disposed in front of an X-ray detector to be used in X-ray imaging, and the X-ray detector may be mounted on the stand 20 or the table 10.

The captured camera image is displayed on the display 150 (operation 311). The camera image 152 may be displayed on the display 150 in real time. The display 150 may be the display 182 provided at the work station 180 or may also be the sub-display 81 included in the sub-display device 80 mounted on the X-ray source 110. Alternatively, the display 150 may also be a display provided at a mobile device such as a smartphone or a tablet PC.

A designation related to a stitching region is received from the user (operation 312). As it has been described in the exemplary embodiment of the X-ray imaging apparatus 100 described above, the user may designate a start point and an end point of the stitching region on the camera image. For example, the start point of the stitching region may be designated using the top line $L_T$, and the end point of the stitching region may be designated using the bottom line $L_B$. Meanwhile, a position of the stitching region may also be designated according to a selected imaging protocol instead of being directly designated by the user. For example, when a protocol related to imaging a chest is selected, a stitching region including the chest may be automatically designated.

When the stitching region is designated, the stitching region S may be divided (operation 313). For example, the controller 140 may divide the stitching region S into a plurality of divided regions having the same size through uniform division. A size of one divided region is not larger than a size of a detection region of the X-ray detector 200. Here, the size of a divided region signifies a size in the vertical direction based on the ground. In another example, the stitching region S may also be divided so that the divided regions thereof have different sizes and may also be divided by the user directly designating a position and shape of each of the divided regions instead of being automatically divided by the controller 140. In an example in which the stitching region S is directly divided by the user, the boundary lines forming the divided windows W1, W2, and W3 displayed by being overlaid on the camera image 152 of the display 150 may be moved to adjust a position and size of each of the divided windows.

An X-ray irradiation condition is set for each of the divided regions (operation 314). Setting the X-ray irradiation condition may be performed by the user's input. As it has been described in the exemplary embodiment of the X-ray imaging apparatus 100 above, the display 150 may display the divided windows W1, W2, and W3 respectively corresponding to the divided regions on the camera image 152 and may display the setting window 151 for setting an X-ray irradiation condition for each of the divided regions together. A GUI through which an X-ray irradiation condition may be set for each of the divided regions may be displayed on the setting window 151, and the GUI may be formed of a plurality of graphical objects each having a specific function. The setting window 151 and the divided windows W1, W2, and W3 may interoperate with each other such that, when a divided region is selected within the setting window 151, a divided window corresponding to the selected divided region is highlighted and displayed, and, when a divided region is selected using a divided window, a settings menu corresponding to the selected divided region may be activated. For example, the setting button 152d for receiving a setting of X-ray irradiation conditions such as a tube voltage, a tube current, and an X-ray exposure time may be displayed together with the divided windows W1, W2, and W3, and settings input through the setting button 152d and a numerical value displayed on the setting window 151 may be synchronized with each other.

For example, identification tags displayed to distinguish a divided region currently targeted for setting an X-ray irradiation condition on the setting window 151 may be matched with the identification tags 152c-1, 152c-2, and 152c-3 displayed on the divided windows W1, W2, and W3.

In this way, the user may accurately recognize a position at which a divided region whose X-ray irradiation condition is currently being set is disposed, and this allows an X-ray irradiation condition to be accurately set for each of the divided regions.

Figure 29:
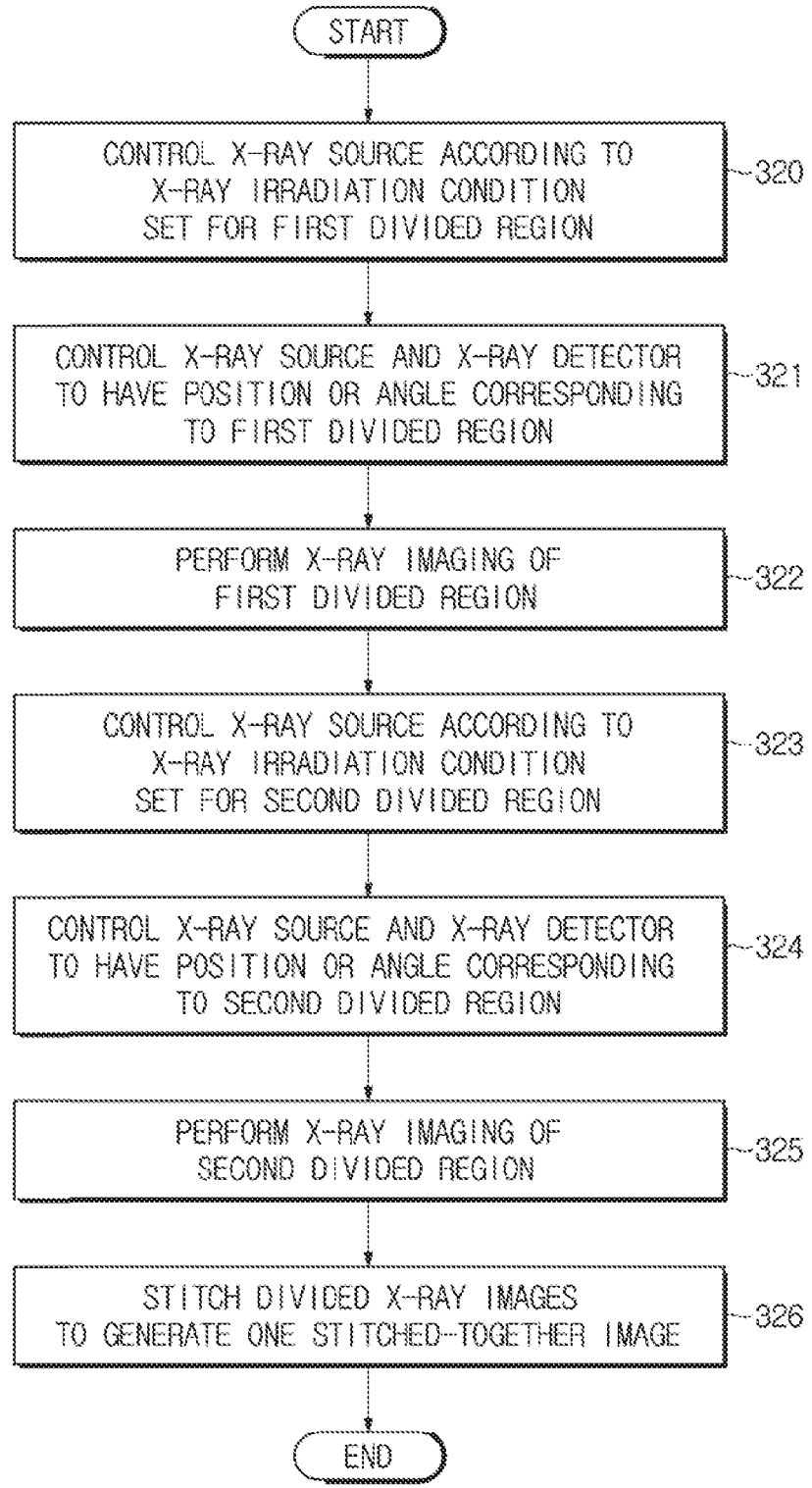
FIG. 29 is a flowchart illustrating an example of performing stitching imaging according to an exemplary embodiment.

FIG. 29 is a flowchart illustrating an example of performing stitching imaging by controlling an X-ray irradiation condition to be different for every divided region in the method for controlling an X-ray imaging apparatus according to an exemplary embodiment.

Referring to FIG. 29, an X-ray source is controlled according to an X-ray irradiation condition set for a first divided region (operation 320). The X-ray irradiation condition may include a tube voltage, a tube current, and an exposure time and may further include other conditions such as an AEC sensor, sensitivity, density, grid, and filter as in the example described above. For example, the X-ray detector 200 may also be controlled according to the type of the X-ray irradiation condition.

The X-ray source and the X-ray detector are controlled to have a position or angle corresponding to the first divided region (operation 321). Since the X-ray detector 200 may move in a direction in which a stitching region is divided, the controller 140 may control the mounting units 14 and 24 on which the X-ray detector 200 is mounted to control a position of the X-ray detector 200. The X-ray source 110 may be moved in the direction in which the stitching region is divided while a tilt angle thereof is fixed, and the tilt angle may be controlled to correspond to the first divided region while the height of the X-ray source 110 from the ground is fixed.

When the X-ray source 110 and the X-ray detector 200 are controlled to be disposed at positions corresponding to the first divided region, X-rays are radiated to perform X-ray imaging of the first divided region (operation 322). When the X-ray imaging of the first divided region is performed, a first divided X-ray image is acquired.

The X-ray source is controlled according to an X-ray irradiation condition set for a second divided region (operation 323). The X-ray irradiation condition set for the second divided region may be different from or the same as that set for the first divided region.

The X-ray source and the X-ray detector are controlled to have a position or angle corresponding to the second divided region (operation 324). The X-ray detector 200 may move in the direction in which the stitching region is divided. The X-ray source 110 may be moved in the direction in which the stitching region is divided while a tilt angle thereof is fixed, and the tilt angle may be controlled to correspond to the second divided region while the height of the X-ray source 110 from the ground is fixed.

When the X-ray source 110 and the X-ray detector 200 are controlled to be disposed at positions corresponding to the second divided region, X-rays are radiated to perform X-ray imaging of the second divided region (operation 325). When the X-ray imaging of the second divided region is performed, a second divided X-ray image is acquired.

When the stitching region includes three or more divided regions, divided imaging up to a third divided region or a fourth divided region may also be performed like the process described above. For example, when the stitching region includes three divided regions, the X-ray source may be controlled according to an X-ray irradiation condition set for the third divided region. The X-ray irradiation condition set for the third divided region may be the same as or different from that set for the first divided region or the second divided region. When the X-ray source and the X-ray detector are controlled to have a position or angle corresponding to the third divided region, and the X-ray source 110 and the X-ray detector 200 are controlled to be disposed at positions corresponding to the third divided region, X-rays are irradiated to perform X-ray imaging of the third divided region. When the X-ray imaging of the third divided region is performed, a third divided X-ray image is acquired. When the stitching imaging is completed, the acquired divided X-ray images are stitched to generate one stitched-together image (operation 326). The generated stitched-together image may be displayed on the display 150.

Although it has been described in the above embodiment that positions of the X-ray source and the X-ray detector are controlled after controlling based on the X-ray irradiation condition is performed, an order of controlling may change, or the controlling based on the X-ray irradiation condition and the controlling of the position may also be simultaneously performed.

Some of the operations of the X-ray imaging apparatus and the method for controlling the same described above may be stored as programs in a computer-readable recording medium. The recording medium may be a magnetic recording medium such as a read-only memory (ROM), a floppy disk, and a hard disk, or an optical recording medium such as a compact disk (CD)-ROM and a digital versatile disk (DVD). However, types of the recording medium are not limited to the examples above.

The recording medium may be included in a server that provides applications or programs, and a work station, a sub-display device, or a mobile device may access the server via a communication protocol such as the internet to download a corresponding program.

For example, when the display 150 and the input unit 160 described above are included in a mobile device, the screen described above may be displayed on the display 150 after the mobile device downloads, installs, and executes a program.

Steps of executing some of the operations of the controller 140 described above may be included in the program. In this case, the mobile device may generate a control command and transmit the control command to the X-ray imaging apparatus 100.

Alternatively, the mobile device may transmit information related to a control command input by the user to the X-ray imaging apparatus 100, and the controller 140 may control the X-ray imaging apparatus 100 according to the control command input by the user.

According to an X-ray imaging apparatus and a method for controlling the same according to an aspect, a plurality of divided regions in which stitching imaging will be performed is displayed in a camera image, and the divided regions displayed on the camera image interoperate with an X-ray irradiation condition setting screen for each of the divided regions to allow a user to intuitively and easily recognize the divided region for which an X-ray irradiation condition is being set.

The foregoing exemplary embodiments and advantages are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An X-ray imaging apparatus comprising:
   an X-ray source configured to radiate X-rays;
   a collimator configured to perform collimation of the radiated X-rays,
   an imaging device configured to capture a camera image; and
   a display configured to display the camera image and at least one graphical object from among a size displaying graphical object showing a size of a collimation region, a length displaying graphical object showing a length of an object captured in the camera image, and a distance displaying graphical object showing a distance between the X-ray source and the object or a distance between the X-ray source and an X-ray detector of the X-ray imaging apparatus, the at least one graphical object being displayed overlaid on the camera image before an X-ray imaging of the object is performed,
   wherein the display is further configured to display an irradiation window corresponding to the collimation region, and the irradiation window is displayed to overlay the camera image and is a graphical object different from the at least one graphical object.

2. The X-ray imaging apparatus of claim 1, wherein the display is further configured to display the size displaying graphical object showing a width of the collimation region at an upper portion of the irradiation window and a height of the collimation region at a side portion of the irradiation window.

3. The X-ray imaging apparatus of claim 1, further comprising:
a controller configured to, based on a size of the irradiation window being adjusted, control the collimator to change the size of the collimation region to correspond to the adjusted size of the irradiation window.

4. The X-ray imaging apparatus of claim 1, wherein the X-ray imaging comprises a first X-ray imaging and a second X-ray imaging, and
wherein, when the second X-ray imaging of the object is to be performed after the first X-ray imaging of the object was performed, the display is further configured to display the irradiation window applied in the first X-ray imaging and an irradiation window to be applied in the second X-ray imaging.

5. The X-ray imaging apparatus of claim 1, wherein the display is further configured to display the length displaying graphical object as a tool that measures a length using a plurality of scales.

6. The X-ray imaging, apparatus of claim 5, wherein the display is further configured to display the length displaying graphical object showing an absolute length of the object.

7. The X-ray imaging apparatus of claim 5, wherein the display is further configured to:
display, on the camera image, a top line for designating an upper boundary of an imaging region in which a first X-ray imaging of the object is to be performed and a bottom line for designating a lower boundary of the imaging region, and
when a second X-ray imaging of the object is to be performed after the first X-ray imaging was performed, display the top line and the bottom line that have been applied in the first X-ray imaging and a top line and a bottom line to be applied in the second X-ray imaging.

8. A method for controlling an X-ray imaging apparatus, the method comprising:
capturing a camera image;
displaying the camera image; and
displaying at least one graphical object from among a size displaying graphical object showing a size of a collimation region, a length displaying graphical object showing a length of an object captured in the camera image, and a distance displaying graphical object showing a distance between an X-ray source of the X-ray imaging apparatus and the object or a distance between the X-ray source and an X-ray detector of the X-ray imaging apparatus, the at least one graphical object being displayed overlaid on the camera image before an X-ray imaging of the object is performed,
wherein the displaying comprises displaying an irradiation window corresponding to the collimation region by overlaying the irradiation window on the camera image, and
the irradiation window is a graphical object different from the at least one graphical object.

9. The method of claim 8, wherein the displaying further comprises:
displaying the size displaying graphical object showing a width of the collimation region at an upper portion of the irradiation window and a height of the collimation region at a side portion of the irradiation window.

10. The method of claim 8, further comprising:
based on a size of the irradiation window being adjusted, controlling a collimator of the X-ray imaging apparatus to change the size of the collimation region to correspond to the adjusted size of the irradiation window.

11. The method of claim 8, further comprising:
when a second X-ray imaging of the object is to be performed after a first X-ray imaging of the object was performed, displaying the irradiation window applied in the first X-ray imaging and an irradiation window to be applied in the second X-ray imaging, the X-ray imaging comprising the first X-ray imaging and the second X-ray imaging.

12. The method of claim 8, wherein the displaying comprises:
displaying the length displaying graphical object being configured as a tool that measures a length using a plurality of scales and showing an absolute length of the object.

13. The method of claim 8, wherein the displaying comprises:
displaying, on the camera image, a top line for designating an upper boundary of an imaging region in which a first X-ray imaging of the object is to be performed and a bottom line for designating a lower boundary of the imaging region; and
when a second X-ray imaging is to be performed after the first imaging was performed, displaying the top line and the bottom line that, have been applied in the first X-ray imaging and a top line and a bottom line to be applied in the second X-ray imaging.

* * * * *